(12) United States Patent
Newell

(10) Patent No.: US 7,381,413 B1
(45) Date of Patent: Jun. 3, 2008

(54) METHODS AND PRODUCTS RELATED TO METABOLIC INTERACTIONS IN DISEASE

(75) Inventor: Martha Karen Newell, Colorado Springs, CO (US)

(73) Assignee: University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 09/277,575

(22) Filed: Mar. 27, 1999

Related U.S. Application Data

(60) Provisional application No. 60/082,250, filed on Apr. 17, 1998, provisional application No. 60/101,580, filed on Sep. 24, 1998, provisional application No. 60/094,519, filed on Jul. 29, 1998.

(51) Int. Cl.
*A61K 39/00* (2006.01)
*A61K 39/395* (2006.01)
*C12N 15/00* (2006.01)
*A01N 43/04* (2006.01)

(52) U.S. Cl. .............. 424/143.1; 424/152.1; 424/155.1; 424/184.1; 514/2; 514/44; 435/320.1

(58) Field of Classification Search .......... 424/34, 424/130.1, 144.1, 154.1, 155.1; 514/21; 524/44; 435/320.1; 530/388.8, 389.7
See application file for complete search history.

(56) References Cited

U.S. PATENT DOCUMENTS

| | | | |
|---|---|---|---|
| 4,724,234 A | 2/1988 | Cone, Jr. | |
| 4,935,450 A | 6/1990 | Cone, Jr. | |
| 4,971,951 A | 11/1990 | Garcia y Bellon et al. | |
| 5,286,653 A | 2/1994 | Brenner et al. | |
| 5,556,754 A | 9/1996 | Singer et al. | |
| 5,585,363 A | 12/1996 | Scanlon et al. | |
| 6,133,946 A | 10/2000 | Cavallaro et al. | |
| 6,416,958 B2 | 7/2002 | Vidovic et al. | |
| 2003/0150022 A1 | 8/2003 | Newell et al. | |
| 2004/0005291 A1 | 1/2004 | Rogers et al. | |
| 2005/0042224 A1 | 2/2005 | Newell | |
| 2005/0074882 A1 | 4/2005 | Newel | |
| 2005/0158333 A1 | 7/2005 | Newell | |

FOREIGN PATENT DOCUMENTS

| | | |
|---|---|---|
| EP | 0524796 | 1/1993 |
| WO | WO-9716188 | 5/1997 |
| WO | WO98/02579 | 1/1998 |
| WO | WO 98/31396 A1 | 7/1998 |
| WO | WO 98/45313 A1 | 10/1998 |
| WO | WO 98/45438 A1 | 10/1998 |
| WO | PCT/US99/06874 | 3/1999 |
| WO | WO 00/47617 | 8/2000 |
| WO | WO 00/78941 A2 | 12/2000 |
| WO | WO 03/031643 A2 | 4/2003 |

OTHER PUBLICATIONS

Burrows et al. Cancer Research 52:2954 Abstract.*
Arsenijevic, D. et al., "Disruption of the uncoupling protein-2 gene in mice reveals a role in immunity and reactive oxygen species production", *Nature Genetics*, Dec. 2000, pp. 435-439, vol. 26, No. 4.
Larrouy, D. et al., "Kupffer Cells are a Dominant Site of Uncoupling Protein 2 Expression in Rat Liver", *Biochemical and Biophysical Research Communications*, 1997, pp. 760-764, vol. 235.
Pecqueur, C. et al., "Upcoupling Protein 2: in vivo distribution, induction upon oxidative stress and evidence for transitional regulation", *JBL Papers in Press Manuscript M006938200*, Nov. 29, 2000, pp. 1-41, The American Society of Biochemistry and Molecular Biology, Inc.
Vidal-Puig, A.J., "Uncoupling expectations", *Nature Genetics*, Dec. 2000, pp. 387-388, vol. 26, No. 4.
Street, D., et al., "Interferon-γ Enhances Susceptibility of Cervical Cancer ells to Lysis by Tumor-Specific Cytotoxic T Cells", *Gynecological Oncology*, (1997), 65:265-272.
Scaffidi, et al., "Two CD95 (APO-1/Fas) Signaling Pathways", The EMBO J., (1998), 1675-87.
Summerfield, et al., "Lymphocyte Apoptosis during Classical Swine Fever Implication of Activation-Induced Cell Death", *J Virology*, (1998), 1853-1861.
Lee, J., et al., "HLA-DR-Mediated Signals for Hematopoiesis and Induction of -Apoptosis Involve But Are Not Limited to a Nitric Oxide Pathway", *Blood*, (1997), 1:217-225.
Genestier, L., et al., "Caspase-dependent Ceramide Production in Fas- and HLA Class I-mediated Peripheral T Cell Apoptosis" J. Bio Chem , (1998) 5060-6.
Satoh, T., et al., "Changes in Mitochondrial Membrane Potential During Oxidative Stress-Induced Apoptosis in PC12 Cells", J. Neuroscience Rese., (1997), 413-420.
Hermesh, O., et al., Mitochondria Uncoupling by a Long Chain Fatty Acyl Analogue, *J. Bio Chem.*, (1998), 273:7-3937-42.
Asoh, Sadamitsu et al., "Expression of the Apoptosis-Mediator Fas. . . ", J. Biochem., vol. 120, pp. 600-607, 1996.
Babu, P.G. et al., "Genetic Control of Multisystem Autoimmune . . . ", Current Topics in Microbiology and Immunology, vol. 122, pp. 154-161, 1985.
Bach, Jean-Francois, "Insulin-Dependent Diabetes Mellitus as an Autoimmune Disease", Endocrine Society, vol. 15, No. 4, pp. 516-542, Aug. 1994.
Baggetto, LG, "Deviant Energetic Metabolism of Glycolytic Cancer Cells", Biochimie, vol. 74, pp. 959-974, 1992.

(Continued)

*Primary Examiner*—Christina Chan
*Assistant Examiner*—F. Pierre VanderVegt
(74) *Attorney, Agent, or Firm*—Wolf Greenfield & Sacks

(57) ABSTRACT

The invention involves methods of regulating cell growth and division to control disease processes by manipulating mitochondrial metabolism and the expression of cell surface immune proteins. The invention also involves related compositions and screening assays.

10 Claims, 27 Drawing Sheets

OTHER PUBLICATIONS

Bhushan, A. et al., "Drug Resistance Results In Alterations . . . ", Immunology and Cell Biology 76, pp. 350-356, 1998.
Billingham, Dr. R. E. et al., "'Actively Acquired Tolerance' of Foreign Cells", Nature, vol. 172, No. 4379, pp. 603-606, Oct. 3, 1953.
Birnboim, H. Chaim and Jagdeep K. Sandhu, "Levels of DNA Strand Breaks . . . ", Journal of Cellular Biochemistry, vol. 66, pp. 219-228, 1997.
Böhme, J. et al., "Transgenic Mice with I-A on Islet Cells . . . ", Science, vol. 244, pp. 1179-1183, Jun. 9, 1989.
Bonfoco, Emanuela et al., "Inducible Nonlymphoid Expression of Fas . . . ", Immunity, vol. 9, pp. 711-720, Nov. 1998.
Caldwell, Kevin K. et al., "Evaluation of Methods for the Isolation . . . ", Analytical Biochemistry, vol. 175, pp. 177-190, 1988.
Cambier, John C. et al., "Ia Binding Ligands and cAMP Stimulate Nuclear Translocation of PKC in B Lymphocytes", Nature, vol. 327, pp. 629-632, Jun. 18, 1987.
Chien, Millie M., et al., "Fas-induced B Cell Apoptosis Requires . . . ", Journal of Biological Chemistry, vol. 274, pp. 1-8, 1999.
Chisari, Francis V. et al., "Molecular Pathogenesis of Hepatocellular Carcinoma . . . ", Cell, vol. 59, pp. 1145-1156, Dec. 22, 1989.
Clément, Marie-Véonique and Ivan Stamenkovic, "Superoxide Anion Is A Natural . . . ", EMBO Journal, vol. 15, No. 2, pp. 216-225, 1996.
Conceicão-Silva, Fatima et al., "The Resolution of Lesions Induced . . . ", Eur. J. Immunol., vol. 28, pp. 237-245, 1998.
Cosgrove, Dominic et al., "Evaluation of the Functional Equivalence of . . . ", J. Exp. Med., vol. 176, pp. 629-634, Aug. 1992.
Cosgrove, Dominic et al., "Mice Lacking MHC Class II Molecules", Cell, vol. 66, pp. 1051-1066, Sep. 6, 1991.
Cossarizza, Andrea et al., "Mitochondrial Modification During Rat . . . ", Experimental Cell Research, vol. 214, pp. 323-330, 1994.
Craighead, John E. et al., "Diverse Patterns of Immune and Non-Immune . . . ", Journal of Autoimmunity, vol. 3, (Supplement), pp. 27-29, 1990.
Creech, Elizabeth A. et al., "MHC Genes Modify Systemic Autoimmune Disease; The Role of the I-E Locus", Journal of Immunology, vol. 156, pp. 812-817, 1996.
Dang, Chi V. and Gregg L. Semenza, "Oncogenic Alterations of Metabolism", TIBS, vol. 24, 1999.
del Carmen Ruiz-Ruiz, Maria et al., "Activation of Protein Kinase C . . . ", Eur. J. Immunol., vol. 27, pp. 1442-1450, 1997.
Denis-Pouxviel, Colette et al., "Regulation of Mitochondrial Hexokinase In Cultured . . . ", Biochimica et Biophysica Acta, vol. 902, pp. 335-348, 1987.
Desbarats, Julie et al., "Fas (CD95) Expression and Death-Mediating . . . ", Proc. Natl. Acad. Sci. USA, vol. 93, pp. 11014-11018, Oct. 1996.
Desbarats, Julie et al., "Newly Discovered Role for Fas Ligand . . . ", Nature Medicine, vol. 4, No. 12, pp. 1377-1382, Dec. 1998.
Fleury, Christophe et al., "Uncoupling Protein-2: A Novel Gene Linked . . . ", Nature Genetics, vol. 15, pp. 269-272, Mar. 1997.
Freedman, M., et al., vδ T-cell-human glial cell interactions . . . susceptibility to cytolysis, J. Neuroimmunology, 74:143-148, 1997.
Fujihashi, Kohtaro et al., "v/δ T Cell-deficient Mice Have Impaired Mucosal Immunoglobulin A Responses," J. Exp. Med., vol. 183, pp. 1929-1935, Apr. 1996.
Garban, Frédéric et al., "Signal Transduction Via Human Leucocyte . . . ", Experimental Hematology, vol. 26, pp. 874-884, 1998.
Garlid, Kieth D. et al., "The Mechanism of Proton Transport . . . ", FEBS Letters, vol. 438, pp. 10-14, 1998.
Golshani-Hebroni, Shiva G. and Samuel P. Bessman, "Hexokinase Binding to Mitochondria: A Basis . . . ", Journal of Bioenergetics and Biomembranes, vol. 29, No. 4, pp. 331-338, 1997.
González-Barroso, M. Mar et al., "The Uncoupling Protein UCP1 Does Not . . . ", Journal of Biological Chemistry, vol. 273, No. 25, pp. 15528-15532, Jun. 19, 1998.

Gorer, P.A., "The Genetic and Antigenic Basis of Tumour Transplantation", Journal of Pathology, vol. XLIV, pp. 691-697.
Gray, Michael W. et al., "Mitochondrial Evolution", Science, vol. 283, pp. 1476-1481, Mar. 5, 1999.
Greiner, Erich F., et al., "Glucose Is Essential for Proliferation and . . . ", Journal of Biological Chemistry, vol. 269, No. 50, pp. 31484-31490, Dec. 16, 1994.
Harper, Mary-Ellen and Martin D. Brand, "Use of Top-Down Elasticity Analysis . . . ", P.S.E.B.M., vol. 208, pp. 228-237, 1995.
Hatefi, Youssef and Mutsuo Yamaguchi, "Nicotinamide Nucleotide Transhydrogenase A Model . . . ", FASEB J., vol. 10, pp. 444-452, Mar. 1996.
Haynes, Mark K., "Helper-Inducer T-Lymphocytes Mediate Diabetes . . . ", Diabetes, vol. 36, pp. 877-881, Jul. 1987.
Hermesh, Orit et al., "Mitochondria Uncoupling by a Long Chain . . . ", Journal of Biological Chemistry, vol. 273, No. 7, pp. 3937-3942, Feb. 13, 1998.
Hess, B. et al., "Cooperation of Glycolytic Enzymes", pp. 149-167.
Himms-Hagen, Jean, "Brown Adipose Tissue Metabolism",Chp. 2, Obesity, Eds. Per Björntorp and Bernard N. Brodoff, J.B. Lippincott Company, Philadelphia, PA, 1992, pp. 15-34.
Hosokawa, H. et al., "Beta-Cell Hypersensitivity to Glucose . . . ", Diabetologia, vol. 40, pp. 392-397, 1997.
Huber, Sally A. and Barbara Pfaeffle, "Differential $TH_1$ and $TH_2$ Cell Responses . . . ", Journal of Virology, vol. 68, No. 8, pp. 5126-5132, Aug. 1994.
Huber, Sally A. et al., "Modulation of Cytokine Expression by CD4 + . . . ", Journal of Virology, vol. 70, No. 5, pp. 3039-3044, May 1996.
Kang, Sang-Mo et al., "Fas Ligand Expression in Islets of . . . ", Nature Medicine, vol. 3, No. 7, pp. 738-743, Jul. 1997.
Kennedy, Eleanor D. et al., "Effects of Depletion of Mitochondrial . . . ", Diabetes, vol. 47, pp. 374-380, Mar. 1998.
Kiberstis, Paula A., "Mitochondria Make A Comeback", Science, vol. 283, p. 1475, Mar. 5, 1999.
Korshunov, Sergey S. et al., "Fatty Acids As Natural Uncouplers . . . ", FEBS Letters, vol. 435, pp. 215-218, 1998.
Lefrancois, Leo et al., "Extrathymic Selection of TCR vδ+ T Cells . . . ", vol. 63, pp. 333-340, Oct. 19, 1990.
Le Meur, Marianne et al., "Correcting An Immune-Response Deficiency by . . . ", Nature, vol. 316, pp. 38-42, Jul. 4, 1985.
Le Meur, Marianne et al., "Restricted Assembly of MHC Class II . . . ", Journal of Immunology, vol. 142, No. 1, pp. 323-327, Jan. 1, 1989.
Logan, Derek T., "A Glycyl Radical Site In . . . ", Science, vol. 283, pp. 1499-1504, Mar. 5, 1999.
Loudon, Robert P. et al., "An Attenuated Variant of Coxsackievirus . . . ", Journal of Virology, vol. 65, No. 11, pp. 5813-5819, Nov. 1991.
Luft, R. and B.R. Landau, "Mitochondrial Medicine", Journal of Internal Medicine, vol. 238, pp. 405-421, 1995.
Lühder, Fred et al., "Major Histocompatibility Complex Class II Molecules . . . ", J. Exp. Med., vol. 187, No. 3, pp. 379-387, Feb. 2, 1998.
Mackaness, George B., "The J. Burns Amberson Lecture—The Induction and Expression of Cell-Mediated Hypersensitivity in the Lung", American Review of Respiratory Disease, vol. 104, pp. 813-828, 1971.
Marzo, Isabel et al., "Bax and Adenine Nucleotide Translocator . . . ", Science, vol. 281, pp. 2027-2031, Sep. 25, 1998.
Mauricio, Didac and Thomas Mandrup-Poulsen, "Apoptosis and the Pathogenesis of IDDM: A Question of Life and Death", Diabetes, vol. 47, pp. 1537-1543, Oct. 1998.
Meuer, Stefan and Klaus Resch, "Cellular Signalling in T Lymphocytes", Immunology Today, vol. 10, No. 8, pp. S23-S25, 1989 Supplement.
Meyer, T., et al., "Giant Cell Myocarditis due to Coxsackie B2 Virus Infection", Cardiology, 88:296-299 1997.
Mieza, M., et al., "Selective Reduction of . . . Disease Development in Autoimmune-Prone Mice", The American Association of Immunologists, 4035-4040, 1996.

Nakamoto, Yasunari et al., "Immune Pathogenesis of Hepatocellular Carcinoma", J. Exp. Med., vol. 188, No. 2, pp. 341-350, Jul. 20, 1998.
Nègre-Salvare, Anne et al., "A Role for Uncoupling Protein-2 . . . ", FASEB J., vol. 11, pp. 809-815, 1997.
Newell, M. Karen et al., "Biochemical Characterization of Proteins that Co-purify . . . ", The Journal of Immunology, vol. 140, No. 6, pp. 1930-1938, Mar. 15, 1988.
Newell, M. Karen et al., "Death of Mature T Cells by Separate . . . ", Nature, vol. 347, pp. 286-289, Sep. 20, 1990.
Newell, M. Karen et al., "Ligation of Major Histocompatibility Complex . . . ", Proc. Natl. Acad. Sci. USA, vol. 90, pp. 10459-10463, Nov. 1993.
Posselt, Andrew M. et al., "Induction of Donor-Specific Unresponsiveness . . . ", Science, vol. 249, pp. 1293-1295, Sep. 4, 1990.
Reyes, Teresa M. and Christopher L. Coe, "The Proinflammatory Cytokine Network: Interactions . . . ", Am. J. Physiol. 274, pp. R139-R144, 1998.
Rustenbeck, Ingo et al., "Energetic Requirement of Insulin Secretion Distal to Calcium Influx", Diabetes, vol. 46, pp. 1305-1311, Aug. 1997.
Saraste, Matti, "Oxidative Phosphorylation at the Fin de Siéle", Science, vol. 283, pp. 1488-1493, Mar. 5, 1999.
Schattner, Elaine J. et al., "CD40 Ligation Induces Apo-1/Fas . . . ", J. Exp. Med., vol. 182, pp. 1557-1565, Nov. 1995.
Schild, Hansjörg et al., "The Nature of Major Histocompatibility Complex Recognition by võ T Cells", Cell, vol. 76, pp. 29-37, Jan. 14, 1994.
Schrezenmeier, Hubert et al., "Inactivation of a T Cell Receptor-Associated GTP-Binding . . . ", J. Exp. Med., vol. 168, pp. 817-822, Aug. 1988.
Sciorati, Clara et al., "Autocrine Nitric Oxide Modulates . . . ", Journal of Biological Chemistry, vol. 272, No. 37, pp. 23211-23215, Sep. 12, 1997.
Skerett, P.J., "New Transplant Method Evades Immune Attack", Science, vol. 249, p. 1248, Sep. 1990.
Snell, George D., "Some Recollections of Peter Gorer and His Work on This Fiftieth Anniversary of His Discovery of H-2", Immunogenetics 24, pp. 339-340, 1986.
Snell, George D., "Studies in Histocompatibility", The Nobel Lectures in Immunology of Dec. 8, 1980, Scandinavian Journal of Immunology 36, pp. 513-526, 1992.
Suzuki, Ivy and Pamela J. Fink, "Maximal Proliferation of Cytotoxic T Lymphocytes . . . ", J. Exp. Med., vol. 187, No. 1, pp. 123-128, Jan. 5, 1998.
Taneja, Veena et al., "Expression of the H2-E Molecule . . . ", International Immunology, vol. 9, No. 8, pp. 1213-1219, 1997.
Teruya, Masanori et al., "Pancreatic Islet Function in Nondiabetic and Diabetic BB Rats", Diabetes, vol. 42, pp. 1310-1317, Sep. 1993.
Tian, Jide and Daniel L. Kaufman, "Attenuation of Inducible Th2 Immunity . . . ", Journal of Immunology, vol. 161, pp. 5399-5403, 1998.
Truman, Jean-Philip et al., "HLA Class II—Mediated Death Is Induced . . . ", Blood, vol. 89, No. 6, pp. 1996-2007, Mar. 15, 1997.
Truman, Jean-Philip et al., "HLA Class II Signaling Mediates . . . ", Experimental Hematology, vol. 24, pp. 1409-1415, 1996.
Wallace, Douglas C., "Mitochondrial Diseases in Man and Mouse", Science, vol. 283, pp. 1482-1488, Mar. 5, 1999.
Wilkens, Stephan and Roderick A. Capaldi, "ATP Synthase's Second Stalk Comes Into Focus", Nature, vol. 393, p. 29, May 7, 1998.
Yaffe, Michael P., "The Machinery of Mitochondrial Inheritance and Behavior", Science, vol. 283, pp. 1493-1497, Mar. 5, 1999.
Zhang, Weiguo et al., "LAT: The ZAP-70 Tyrosine Kinase . . . ", Cell, vol. 92, pp. 83-92, Jan. 9, 1998.
Zinkernagel, Rolf M. and Peter C. Doherty, "The Discovery of MHC Restriction", Immunology Today, vol. 18, No. 1, pp. 14-17, Jan. 1997.
Palu, G. et al. "In pursuit of new developments for gene therapy of human diseases", Journal of Biotech, vol. 68, pp. 1-13, 1999.
Stayton, P. et al. "Molecular engineering of proteins and polymers for targeting and intracellular delivery of therapeutics", Journal of Controlled Releases, vol. 65, pp. 203-220, 2000.

[No Author Listed] Taxol Product Literature. Bristol Myers Squibb. 2003: 1-6.
Berg et al., Pharmacokinetics of taxol and doxorubicin administered alone and in combination by continuous 72-hour infusion. J Natl Cancer Inst. Jan. 19, 1994; 86(2):143-5.
Bodmer et al., Identification of HLA-DP polymorphism with DP alpha and DP beta probes and monoclonal antibodies: correlation with primed lymphocyte typing. Proc Natl Acad Sci U S A Jul. 1987; 84(13):4596-600.
Carrel et al., Recombinant interferon-gamma can induce the expression of HLA-DR and—DC on DR-negative melanoma cells and enhance the expression of HLA-ABC and tumor-associated antigens. Eur J Immunol. Feb. 1985; 15(2):118-23.
Crump et al., Gemcitabine, dexamethasone, and cisplatin in patients with recurrent or refractory aggressive histology B-cell non-Hodgkin lymphoma: a Phase II study by the National Cancer Institute of Canada Clinical Trials Group (NCIC-CTG). Cancer. Oct. 15, 2004; 101(8):1835-42.
Deen et al., A soluble form of CD4 (T4) protein inhibits AIDS virus infection. Nature, Jan. 7, 1988; 331(6151):82-4.
Fanciulli et al., Effect of the antitumor drug lonidamine on glucose metabolism of adriamycin-sensitive and -resistant human breast cancer cells. Oncol Res. 1996; 8(3):111-20.
Hedley et al., Assembly and peptide binding of major histocompatibility complex class II heterodimers in an in vitro translation system. Proc Natl Acad Sci U S A. Oct. 25, 1994; 91(22):10479-83.
Hess et al., A novel function of CD40: induction of cell death in transformed cells. J Exp Med. Jan. 1, 1996; 183(1):159-67.
Hoon et al., Modulation of human melanoma cells by interleukin-4 and in combination with gamma-interferon or alpha-tumor necrosis factor. Cancer Res. Apr. 15, 1991; 51(8):2002-8.
Ianniello et al., Cisplatin, epirubicin, and vindesine with or without Ionidamine in the treatment of inoperable nonsmall cell lung carcinoma: a multicenter randomized clinical trial. Cancer. Jul. 1, 1996; 78(1):63-9.
Khoury et al., Ex vivo treatment of antigen-presenting cells with CTLA4lg and encephalitogenic peptide prevents experimental autoimmune encephalomyelitis in the Lewis rat J Immunol. Oct. 15, 1996; 157(8):3700-5.
Kuchroo et al., B7-1 and B7-2 costimulatory molecules activate differentially the Th1/Th2 developmental pathways: application to autoimmune disease therapy. Cell. Mar. 10, 1995; 80(5):707-18.
LaMarre et al., Class II MHC molecules and the HIV gp 120 envelope protein interact with functionally distinct regions of the CD4 molecule. EMBO J. Nov. 1989; 8(11):3271-7.
Mizuno et al., The proteolytic cleavage of protein kinase C isotypes, which generates kinase and regulatory fragments, correlates with Fas-mediated and 12-O-tetradecanoyl-phorbol-13-acetate-induced apoptosis. Eur J Biochem. Nov. 15, 1997; 250(1):7-18.
Newell et al., The effects of chemotherapeutics on cellular metabolism and consequent immune recognition. J Immune Based Ther Vaccines. Feb. 2, 2004; 2(1):3.
Posada et al., Human multidrug resistant KB cells overexpress protein kinase C: involvement in drug resistance. Cancer Commun. 1989;1(5):285-92.
Stassi et al., Nitric oxide primes pancreatic beta cells for Fas-mediated destruction in insulin-dependent diabetes mellitus. J Exp Med. Oct. 20, 1997; 186(8):1193-200.
Suzuki et al., Activation of target-tissue immune-recognition molecules by double-stranded polynucleotides. Proc Natl Acad Sci U S A. Mar. 2, 1999; 96(5):2285-90.
Tansan et al., Augmentation of vincristine cytotoxicity by megestrol acetate. Cancer Chemother Pharmacol. 1997; 39(4):333-40.
Utz et al., The protein kinase C inhibitor CGP 41251, a staurosporine derivative with antitumor activity, reverses multidrug resistance. Int J Cancer. Apr. 1, 1994; 57(1):104-10.
Wang et al., Effects of cisplatin and taxol on inducible nitric oxide synthase, gastrin and somatostatin in gastrointestinal toxicity. Anti-cancer Drugs. Oct. 1997; 8(9):853-8.
Bryder et al., Hematopoietic Stem Cells The Paradigmatic Tissue-Specific Stem Cell, Am J of Pathology. Aug. 2006; 169(2): 338-346.

Roll et al., Regeneration of B Cell Subsets After Transient B Cell Depletion Using Anti-CD20 Antibodies in Rheumatoid Arthritis. Arthritis & Rheumatism, Aug. 2006; 54(8): 2377-2386.

Wang et al., Purified hematopoietic stem cells without facilitating cells can repopulate fully allogeneic recipients across entire major histocompatibility complex transplantation barrier in mice. Proc. Natl. Acad. Sci. Dec. 1997; vol. 94: 14632-14636.

Agrawal S. et al. "Antisense therapeutics: is it as simple as complementary base recognition?" *Molecular Med. Today*, vol. 6. pp. 72-81, 2000.

Bouillaud, F. et al. "A sequence related to a DNA recognition element is essential for the inhibition by nucleotides of proton transport through the mitchondrial uncoupling protein," *The EMBO Journal*, vol. 13, No. 8, pp. 1990-1997, 1994.

Branch, A. "A good antisense molecule is hard to find," *Trends in Biochem. Sci.*, vol. 23, pp. 45-50, 1998.

Chirla, T. et al. "The use of synthetic polymers for delivery of therapeutic antisense oligodeoxynucleotides," *Biomaterials*, vol. 23, pp. 321-342, 2002.

Crooke, S. *Antisense Research and Application*, (Ed. by S. Crooke), pp. 1-50, Springer-Verlag, 1999.

Eliopoulos, AG et al. "CD40 Stimulation Augments Apoptosis In Carcinoma Cell Lines," *J. Cellular Biochem*, (supplemental 19B), Abstract B8-123, p. 271, 1995.

Lobato, M. et al. "Intracellular antibodies and challenges facing their use as therapeutic agents," *Trends in Molecular Medicine*, vol. 9, No. 9, pp. 390-396, 2003.

Morimoto, H. et al. "Overcoming Tumor Necrosis Factor and Drug Resistance of Humor Tumor Cell Lines by Combination Treatment with Anti-Fas Antibody and Drugs or Toxins," *Cancer Research*, 53(11), pp. 2591-2596, 1993.

Pihl-Carey, K. "Disease Drug Fails in Phase III," *BioWorld Today*, vol. 10, pp. 1-2, 1999.

\* cited by examiner

MHC class II mediated increases in cAMP are isotype and dimerization/oligomerization state dependent MHC class II induces apoptotic cell death

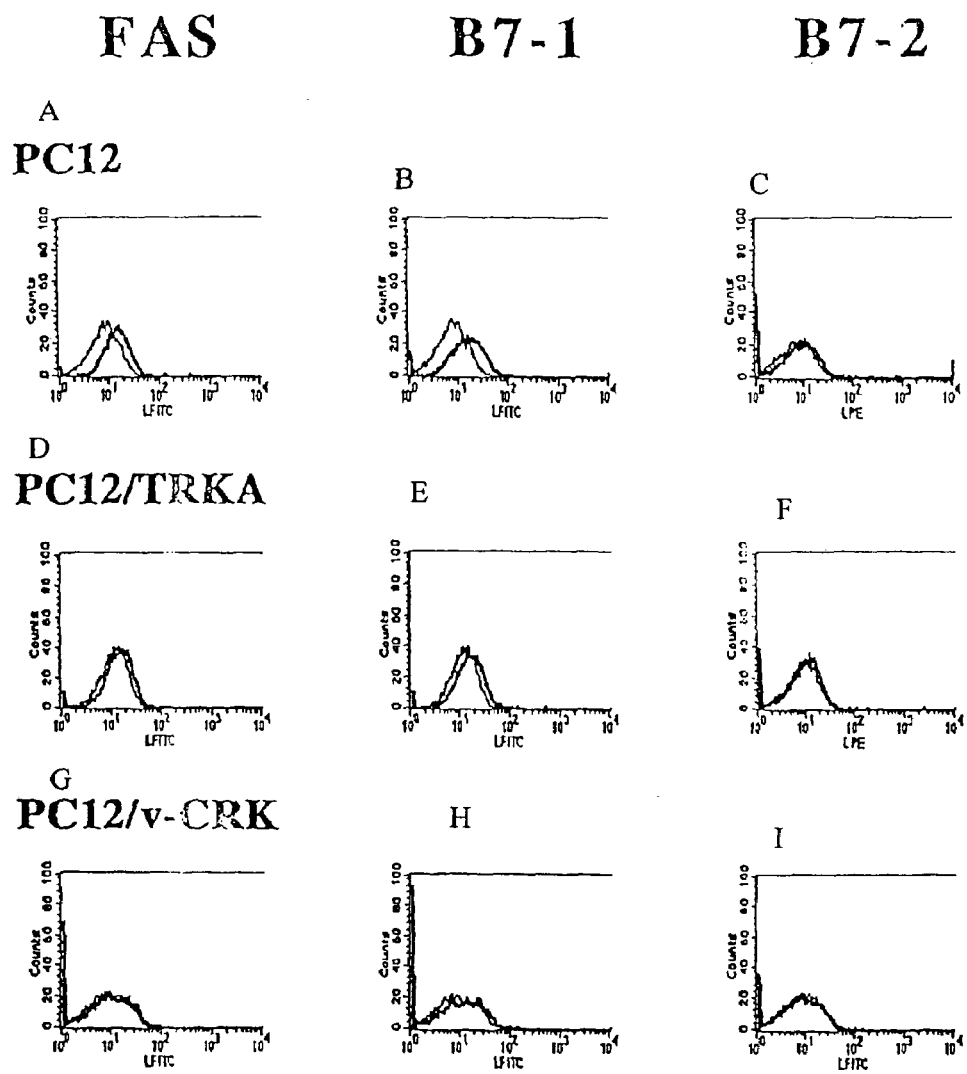
Figure 25: Histograms depicting the constitutive expression or lack thereof of the cell surface molecules Fas, B7.1, and B7.2 on PC12 cells and their variants Trk and v-Crk.

SEQUENCE LISTING

<160> NUMBER OF SEQ ID NOS: 13

<210> SEQ ID NO 1
<211> LENGTH: 1491
<212> TYPE: DNA
<213> ORGANISM: Homo Sapiens

<400> SEQUENCE: 1

```
ccaaagaaaa agtgatttgt cattgcttta tagactgtaa gaagagaaca tctcagaagt      60
ggagtcttac cctgaaatca aaggatttaa agaaaaagtg gaattttct tcagcaagct      120
gtgaaactaa atccacaacc tttggagacc caggaacacc ctccaatctc tgtgtgtttt     180
gtaaacatca ctggagggtc ttctacgtga gcaattggat tgtcatcagc cctgcctgtt     240
ttgcacctgg gaagtgccct ggtcttactt gggtccaaat tgttggcttt cacttttgac     300
cctaagcatc tgaagccatg gccacacac ggaggcaggg aacatcacca tccaagtgtc      360
catacctcaa tttctttcag ctcttggtgc tggctggtct ttctcacttc tgttcaggtg     420
ttatccacgt gaccaaggaa gtgaaagaag tggcaacgct gtcctgtggt cacaatgttt     480
ctgttgaaga gctggcacaa actcgcatct actggcaaaa ggagaagaaa atggtgctga     540
ctatgatgtc tggggacatg aatatatggc ccgagtacaa gaaccggacc atctttgata     600
tcactaataa cctctccatt gtgatcctgg ctctgcgccc atctgacgag ggcacatacg     660
agtgtgttgt tctgaagtat gaaaaagacg cttttcaagcg ggaacacctg gctgaagtga     720
cgttatcagt caaagctgac ttccctacac ctagtatatc tgactttgaa attccaactt     780
ctaatattag aaggataatt tgctcaacct ctggaggttt tccagagcct cacctctcct     840
ggttggaaaa tggagaagaa ttaaatgcca tcaacacaac agtttcccaa gatcctgaaa     900
ctgagctcta tgctgttagc agcaaactgg atttcaatat gacaaccaac cacagcttca     960
tgtgtctcat caagtatgga catttaagag tgaatcagac cttcaactgg aatacaacca    1020
agcaagagca ttttcctgat aacctgctcc catcctgggc cattacctta atctcagtaa    1080
atggaatttt tgtgatatgc tgcctgacct actgctttgc cccaagatgc agagagaaa     1140
ggaggaatga gagattgaga agggaaagtg tacgccctgt ataacagtgt ccgcagaagc    1200
aagggctga aaagatctga aggtagcctc cgtcatctct tctgggatac atggatcgtg    1260
gggatcatga ggcattcttc ccttaacaaa tttaagctgt tttacccact acctcacctt    1320
cttaaaaacc tctttcagat taagctgaac agttacaaga tggctggcat ccctctcctt    1380
tctccccata tgcaatttgc ttaatgtaac ctcttctttt gccatgtttc cattctgcca    1440
tcttgaattg tcttgtcagc caattcatta tctattaaac actaatttga g             1491
```

<210> SEQ ID NO 2
<211> LENGTH: 288
<212> TYPE: PRT
<213> ORGANISM: Homo Sapiens

<400> SEQUENCE: 2

```
Met Gly His Thr Arg Arg Gln Gly Thr Ser Pro Ser Lys Cys Pro Tyr
 1               5                  10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45
```

```
Ser Cys Gly His Asn Val Ser Val Glu Glu Leu Ala Gln Thr Arg Ile
 50                  55                  60

Tyr Trp Gln Lys Glu Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285

<210> SEQ ID NO 3
<211> LENGTH: 1424
<212> TYPE: DNA
<213> ORGANISM: Homo Sapiens

<400> SEQUENCE: 3
aggagcctta ggaggtacgg ggagctcgca aatactcctt ttggtttatt cttaccacct      60
tgcttctgtg ttccttggga atgctgctgt gcttatgcat ctggtctctt tttggagcta    120
cagtggacag gcatttgtga cagcactatg ggactgagta acattctctt tgtgatggcc    180
ttcctgctct ctggtgctgc tcctctgaag attcaagctt atttcaatga gactgcagac    240
ctgccatgcc aatttgcaaa ctctcaaaac aaagcctga gtgagctagt agtattttgg    300
caggaccagg aaaacttggt tctgaatgag gtatacttag caaagagaa atttgacagt    360 gttcattcca gtatatgggg ccgcacaagt tttgattcgg acagttggac cctgagactt    420
cacaatcttc agatcaagga caagggcttg tatcaatgta tcatccatca caaaaagccc    480
acaggaatga ttcgcatcca ccagatgaat tctgaactgt cagtgcttgc taacttcagt    540
caacctgaaa tagtaccaat ttctaatata acagaaaatg tgtacataaa tttgacctgc    600
tcatctatac acggttaccc agaacctaag aagatgagtg ttttgctaag aaccaagaat    660
tcaactatcg agtatgatgg tattatgcag aaatctcaag ataatgtcac agaactgtac    720
gacgtttcca tcagcttgtc tgtttcattc cctgatgtta cgagcaatat gaccatcttc    780
```

-continued

```
tgtattctgg aaactgacaa gacgcggctt ttatcttcac ctttctctat agagcttgag   840
gaccctcagc ctcccccaga ccacattcct tggattacag ctgtacttcc aacagttatt   900
atatgtgtga tggttttctg tctaattcta tggaaatgga agaagaagaa gcggcctcgc   960
aactcttata aatgtggaac caacacaatg gagagggaag agagtgaaca gaccaagaaa  1020
agagaaaaaa tccatatacc tgaaagatct gatgaagccc agcgtgtttt taaaagttcg  1080
aagacatctt catgcgacaa aagtgataca tgttttttaat taaagagtaa agcccataca  1140
agtattcatt tttctaccc tttcctttgt aagttcctgg gcaaccttt tgatttcttc    1200 cagaaggcaa aaagacatta ccatgagtaa taagggggct ccaggactcc ctctaagtgg  1260
aatagcctcc ctgtaactcc agctctgctc cgtatgccaa gaggagactt taattctctt  1320
actgcttctt ttcacttcag agcacactta tgggccaagc ccagcttaat ggctcatgac  1380
ctggaaataa aatttaggac aataaaaaaa aaaaaaaaaa aaaa                   1424
```

<210> SEQ ID NO 4
<211> LENGTH: 323
<212> TYPE: PRT
<213> ORGANISM: Homo Sapiens

<400> SEQUENCE: 4

```
Met Gly Leu Ser Asn Ile Leu Phe Val Met Ala Phe Leu Leu Ser Gly
 1               5                   10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
    130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                165                 170                 175

Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Ile Leu Glu Thr Asp Lys Thr Arg Leu Leu Ser Ser
    210                 215                 220

Pro Phe Ser Ile Glu Leu Glu Asp Pro Gln Pro Pro Asp His Ile
225                 230                 235                 240

Pro Trp Ile Thr Ala Val Leu Pro Thr Val Ile Ile Cys Val Met Val
                245                 250                 255

Phe Cys Leu Ile Leu Trp Lys Trp Lys Lys Lys Lys Arg Pro Arg Asn
```

```
                    260                 265                 270
Ser Tyr Lys Cys Gly Thr Asn Thr Met Glu Arg Glu Ser Glu Gln
            275                 280                 285

Thr Lys Lys Arg Glu Lys Ile His Ile Pro Glu Arg Ser Asp Glu Ala
    290                 295                 300

Gln Arg Val Phe Lys Ser Ser Lys Thr Ser Ser Cys Asp Lys Ser Asp
305                 310                 315                 320

Thr Cys Phe

<210> SEQ ID NO 5
<211> LENGTH: 924
<212> TYPE: DNA
<213> ORGANISM: Homo Sapiens

<400> SEQUENCE: 5 atgggggggcc tgacagcctc ggacgtacac ccgaccctgg gggtccagct cttctcagct    60
ggaatagcgg cgtgcttggc ggacgtgatc accttcccgc tggacacggc caaagtccgg   120
ctccaggtcc aaggtgaatg cccgacgtcc agtgttatta ggtataaagg tgtcctggga   180
acaatcaccg ctgtggtaaa aacagaaggg cggatgaaac tctacagcgg gctgcctgcg   240
gggcttcagc ggcaaatcag ctccgcctct ctcaggatcg gcctctacga cacggtccag   300
gagttcctca ccgcagggaa agaaacagca cctagtttag aagcaagat tttagctggt   360 ctaacgactg gaggagtggc agtattcatt gggcaaccca cagaggtcgt gaaagtcaga   420
cttcaagcac agagccatct ccacggaatc aaacctcgct acacggggac ttataatgcg   480
tacagaataa tagcaacaac cgaaggcttg acgggtcttt ggaaagggac tactcccaat   540
ctgatgagaa gtgtcatcat caattgtaca gagctagtaa catatgatct aatgaaggag   600
gcctttgtga aaacaacat attagcagat gacgtcccct gccacttggt gtcggctctt   660
atcgctggat tttgcgcaac agctatgtcc tccccggtgg atgtagtaaa accagatttt   720
attaattctc caccaggaca gtacaaaagt gtgcccaact gtgcaatgaa agtgttcact   780
aacgaaggac caacgcttt cttcaagggg ttggtacctt ccttcttgcg acttggatcc   840
tggaacgtca ttatgttttgt gtgctttgaa caactgaaac gagaactgtc aaagtcaagg   900
cagactatgg actgtgccac ataa                                           924

<210> SEQ ID NO 6
<211> LENGTH: 307
<212> TYPE: PRT
<213> ORGANISM: Homo Sapiens

<400> SEQUENCE: 6

Met Gly Gly Leu Thr Ala Ser Asp Val His Pro Thr Leu Gly Val Gln
1               5                   10                  15

Leu Phe Ser Ala Gly Ile Ala Ala Cys Leu Ala Asp Val Ile Thr Phe
            20                  25                  30

Pro Leu Asp Thr Ala Lys Val Arg Leu Gln Val Gln Gly Glu Cys Pro
        35                  40                  45

Thr Ser Ser Val Ile Arg Tyr Lys Gly Val Leu Gly Thr Ile Thr Ala
    50                  55                  60

Val Val Lys Thr Glu Gly Arg Met Lys Leu Tyr Ser Gly Leu Pro Ala
65                  70                  75                  80

Gly Leu Gln Arg Gln Ile Ser Ser Ala Ser Leu Arg Ile Gly Leu Tyr
            85                  90                  95
```

-continued

```
Asp Thr Val Gln Glu Phe Leu Thr Ala Gly Lys Glu Thr Ala Pro Ser
                100                 105                 110
Leu Gly Ser Lys Ile Leu Ala Gly Leu Thr Thr Gly Val Ala Val
            115                 120                 125
Phe Ile Gly Gln Pro Thr Glu Val Val Lys Val Arg Leu Gln Ala Gln
        130                 135                 140
Ser His Leu His Gly Ile Lys Pro Arg Tyr Thr Gly Thr Tyr Asn Ala
145                 150                 155                 160
Tyr Arg Ile Ile Ala Thr Thr Glu Gly Leu Thr Gly Leu Trp Lys Gly
                165                 170                 175
Thr Thr Pro Asn Leu Met Arg Ser Val Ile Ile Asn Cys Thr Glu Leu
            180                 185                 190
Val Thr Tyr Asp Leu Met Lys Glu Ala Phe Val Lys Asn Asn Ile Leu
        195                 200                 205
Ala Asp Asp Val Pro Cys His Leu Val Ser Ala Leu Ile Ala Gly Phe
    210                 215                 220
Cys Ala Thr Ala Met Ser Ser Pro Val Asp Val Val Lys Thr Arg Phe
225                 230                 235                 240
Ile Asn Ser Pro Pro Gly Gln Tyr Lys Ser Val Pro Asn Cys Ala Met
                245                 250                 255
Lys Val Phe Thr Asn Glu Gly Pro Thr Ala Phe Phe Lys Gly Leu Val
            260                 265                 270
Pro Ser Phe Leu Arg Leu Gly Ser Trp Asn Val Ile Met Phe Val Cys
        275                 280                 285
Phe Glu Gln Leu Lys Arg Glu Leu Ser Lys Ser Arg Gln Thr Met Asp
    290                 295                 300
Cys Ala Thr
305

<210> SEQ ID NO 7
<211> LENGTH: 1105
<212> TYPE: DNA
<213> ORGANISM: Homo Sapiens

<400> SEQUENCE: 7
gttcctctat ctcgtcttgt tgctgattaa aggtgcccct gtctccagtt tttctccatc        60
tcctgggacg tagcaggaaa tcagcatcat ggttgggttc aaggccacag atgtgccccc       120
tactgccact gtgaagtttc ttggggctgg cacagctgcc tgcatcgcag atctcatcac       180
ctttcctctg gatactgcta aagtccggtt acagatccaa ggagaaagtc aggggccagt       240
gcgcgctaca gccagcgccc agtaccgcgg tgtgatgggc accattctga ccatggtgcg       300
tactgagggc ccccgaagcc tctacaatgg gctggttgcc ggcctgcagc gccaaatgag       360
ctttgcctct gtccgcatcg gcctgtatga ttctgtcaaa cagttctaca ccaagggctc       420
tgagcatgcc agcattggga gccgcctcct agcaggcagc accacaggtg ccctggctgt       480
ggctgtggcc cagcccacgg atgtggtaaa ggtccgattc caagctcagg cccgggctgg       540
aggtggtcgg agataccaaa gcaccgtcaa tgcctacaag accattgccc gagaggaagg       600
gttccggggc ctctggaaag ggaccctctcc caatgttgct cgtaatgcca ttgtcaactg       660
tgctgagctg gtgaccctatg acctcatcaa ggatgccctc ctgaaagcca acctcatgac       720
agatgacctc ccttgccact tcacttctgc ctttggggca ggcttctgca ccactgtcat       780
cgcctcccct gtagacgtgg tcaagacgag atacatgaac tctgccctgg ccagtacagg       840
tagcgctggc cactgtgccc ttaccatgct ccagaaggag gggccccgag ccttctacaa       900
```

```
agggttcatg ccctcctttc tccgcttggg ttcctggaac gtggtgatgt tcgtcaccta    960
tgagcagctg aaacgagccc tcatggctgc ctgcacttcc cgagaggctc ccttctgagc   1020
ctctcctgct gctgacctga tcacctctgg ctttgtctct agccgggcca tgctttcctt   1080
ttcttccttc tttctcttcc ctccg                                         1105
```

<210> SEQ ID NO 8
<211> LENGTH: 309
<212> TYPE: PRT
<213> ORGANISM: Homo Sapiens

<400> SEQUENCE: 8

```
Met Val Gly Phe Lys Ala Thr Asp Val Pro Thr Ala Thr Val Lys
 1               5                  10                  15

Phe Leu Gly Ala Gly Thr Ala Ala Cys Ile Ala Asp Leu Ile Thr Phe
             20                  25                  30

Pro Leu Asp Thr Ala Lys Val Arg Leu Gln Ile Gln Gly Glu Ser Gln
         35                  40                  45

Gly Pro Val Arg Ala Thr Ala Ser Ala Gln Tyr Arg Gly Val Met Gly
     50                  55                  60

Thr Ile Leu Thr Met Val Arg Thr Glu Gly Pro Arg Ser Leu Tyr Asn
 65                  70                  75                  80

Gly Leu Val Ala Gly Leu Gln Arg Gln Met Ser Phe Ala Ser Val Arg
                 85                  90                  95

Ile Gly Leu Tyr Asp Ser Val Lys Gln Phe Tyr Thr Lys Gly Ser Glu
            100                 105                 110

His Ala Ser Ile Gly Ser Arg Leu Leu Ala Gly Ser Thr Thr Gly Ala
        115                 120                 125

Leu Ala Val Ala Val Ala Gln Pro Thr Asp Val Val Lys Val Arg Phe
    130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
            180                 185                 190

Glu Leu Val Thr Tyr Asp Leu Ile Lys Asp Ala Leu Leu Lys Ala Asn
        195                 200                 205

Leu Met Thr Asp Asp Leu Pro Cys His Phe Thr Ser Ala Phe Gly Ala
    210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
            260                 265                 270

Phe Met Pro Ser Phe Leu Arg Leu Gly Ser Trp Asn Val Val Met Phe
        275                 280                 285

Val Thr Tyr Glu Gln Leu Lys Arg Ala Leu Met Ala Ala Cys Thr Ser
    290                 295                 300

Arg Glu Ala Pro Phe
305
```

<210> SEQ ID NO 9

<211> LENGTH: 1132
<212> TYPE: DNA
<213> ORGANISM: Homo Sapiens

<400> SEQUENCE: 9

```
tcctgggatg gagccctagg gagcccctgt gctgccccctg ccgtggcagg actcacagcc      60
ccaccgctgc actgaagccc agggctgtgg agcagcctct ctccttggac ctcctctcgg     120
ccctaaaggg actgggcaga gccttccagg actatggttg gactgaagcc ttcagacgtg     180
cctcccacca tggctgtgaa gttcctgggg gcaggcacag cagcctgttt tgctgacctc     240
gttacctttc cactggacac agccaaggtc cgcctgcaga tccagggggga gaaccaggcg     300
gtccagacgg cccggctcgt gcagtaccgt ggcgtgctgg gcaccatcct gaccatggtg     360
cggactgagg gtccctgcag ccctacaat gggctggtgg ccggcctgca gcgccagatg     420
agcttcgcct ccatccgcat cggcctctat gactccgtca gcaggtgta caccccccaaa    480
ggcgcggaca ctccagcct cactacccgg attttggccg gctgcaccac aggagccatg     540
gcggtgacct gtgcccagcc cacagatgtg gtgaaggtcc gatttcaggc cagcatacac     600
ctcgggccat ccaggagcga cagaaaatac agcgggacta tggacgccta cagaaccatc     660
gccagggagg aaggagtcag gggcctgtgg aaaggaactt tgcccaacat catgaggaat     720
gctatcgtca actgtgctga ggtggtgacc tacgacatcc tcaaggagaa gctgctggac     780
taccacctgc tcactgacaa cttcccctgc cactttgtct ctgcctttgg agccggcttc     840
tgtgccacag tggtggcctc cccggtggac gtggtgaaga cccggtatat gaactcacct     900
ccaggccagt acttcagccc cctcgactgt atgataaaga tggtggccca ggagggcccc     960
acagccttct acaaggggtg agcctcctcc tgcctccagc actccctccc agagaacagg    1020
ggcttctttc ttttcgaatg tggctaccgt gggtcaacct gggatgtagc ggtgaagagt    1080
acagatgtaa atgccacaaa gaagaagttt aaaaaaccat gcaaaaaaaa aa             1132
```

<210> SEQ ID NO 10
<211> LENGTH: 275
<212> TYPE: PRT
<213> ORGANISM: Homo Sapiens

<400> SEQUENCE: 10

```
Met Val Gly Leu Lys Pro Ser Asp Val Pro Thr Met Ala Val Lys
  1               5                  10                  15

Phe Leu Gly Ala Gly Thr Ala Ala Cys Phe Ala Asp Leu Val Thr Phe
                 20                  25                  30

Pro Leu Asp Thr Ala Lys Val Arg Leu Gln Ile Gln Gly Glu Asn Gln
             35                  40                  45

Ala Val Gln Thr Ala Arg Leu Val Gln Tyr Arg Gly Val Leu Gly Thr
         50                  55                  60

Ile Leu Thr Met Val Arg Thr Glu Gly Pro Cys Ser Pro Tyr Asn Gly
 65                  70                  75                  80

Leu Val Ala Gly Leu Gln Arg Gln Met Ser Phe Ala Ser Ile Arg Ile
                 85                  90                  95

Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
        115                 120                 125

Met Ala Val Thr Cys Ala Gln Pro Thr Asp Val Val Lys Val Arg Phe
    130                 135                 140
```

-continued

```
Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
            180                 185                 190

Asn Cys Ala Glu Val Val Thr Tyr Asp Ile Leu Lys Glu Lys Leu Leu
        195                 200                 205

Asp Tyr His Leu Leu Thr Asp Asn Phe Pro Cys His Phe Val Ser Ala
    210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
            260                 265                 270

Tyr Lys Gly
        275
```

<210> SEQ ID NO 11
<211> LENGTH: 1514
<212> TYPE: DNA
<213> ORGANISM: Homo Sapiens

<400> SEQUENCE: 11

```
agactctcag gccttggcag gtgcgtcttt cagttcccct cacacttcgg gttcctcggg      60
gaggagggc tggaacccta gcccatcgtc aggacaaaga tgctcaggct gctcttggct     120
ctcaacttat tcccttcaat tcaagtaaca ggaaacaaga ttttggtgaa gcagtcgccc     180
atgcttgtag cgtacgacaa tgcggtcaac cttagctgca agtattccta caatctcttc     240
tcaagggagt tccgggcatc ccttcacaaa ggactggata tgctgtgga agtctgtgtt     300
gtatatggga attactccca gcagcttcag gtttactcaa aaacgggtt caactgtgat     360
gggaaattgg gcaatgaatc agtgacattc tacctccaga atttgtatgt taaccaaaca     420
gatatttact tctgcaaaat tgaagttatg tatcctcctc cttacctaga caatgagaag     480
agcaatggaa ccattatcca tgtgaaaggg aaacaccttt gtccaagtcc cctatttccc     540
ggaccttcta gcccttttg ggtgctggtg gtggttggtg gagtcctggc ttgctatagc     600
ttgctagtaa cagtggcctt tattattttc tgggtgagga gtaagaggag caggctcctg     660
cacagtgact acatgaacat gactccccgc cgccccgggc ccacccgcaa gcattaccag     720
ccctatgccc caccacgcga cttcgcagcc tatcgctcct gacacggacg cctatccaga     780
agccagccgg ctggcagccc ccatctgctc aatatcactg ctctggatag gaaatgaccg     840
ccatctccag ccggccacct cagccccctgt tgggccacca atgccaattt ttctcgagtg     900
actagaccaa atatcaagat catttttgaga ctctgaaatg aagtaaaaga gatttcctgt     960
gacaggccaa gtcttacagt gccatggccc acattccaac ttaccatgta cttagtgact    1020
tgactgagaa gttagggtag aaaacaaaaa gggagtggat tctgggagcc tcttcccttt    1080
ctcactcacc tgcacatctc agtcaagcaa agtgtggtat ccacagacat tttagttgca    1140
gaagaaaggc taggaaatca ttccttttgg ttaaatgggt gtttaatctt ttggttagtg    1200
ggttaaacgg ggtaagttag agtaggggga gggataggaa gacatattta aaaaccatta    1260
aaacactgtc tcccactcat gaaatgagcc acgtagttcc tatttaatgc tgttttcctt    1320
```

```
tagtttagaa atacatagac attgtctttt atgaattctg atcatattta gtcattttga   1380
ccaaatgagg gatttggtca aatgagggat tccctcaaag caatatcagg taaaccaagt   1440
tgctttcctc actccctgtc atgagacttc agtgttaatg ttcacaatat actttcgaaa   1500
gaataaaata gttc                                                     1514
```

<210> SEQ ID NO 12
<211> LENGTH: 220
<212> TYPE: PRT
<213> ORGANISM: Homo Sapiens

<400> SEQUENCE: 12

```
Met Leu Arg Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 13
<211> LENGTH: 8
<212> TYPE: PRT
<213> ORGANISM: Homo Sapiens

<400> SEQUENCE: 13

```
Arg His Arg Ser Gln Lys Gly Pro
 1               5
```

METHODS AND PRODUCTS RELATED TO METABOLIC INTERACTIONS IN DISEASE

This application claims priority under 35 USC §119(e) from U.S. Provisional Application Ser. No. 60/082,250 filed Apr. 17, 1998, U.S. Provisional Application Ser. No. 60/101,580 filed Sep. 24, 1998 and U.S. Provisional Application Ser. No. 60/094,519 filed Jul. 29, 1998.

GOVERNMENT SUPPORT

This invention was made with Government support under Grant/Contract No. AI 33470 awarded by the National Institute of Health. The Government may retain certain rights in this invention.

FIELD OF THE INVENTION

This invention relates to methods of regulating cell growth and division to control disease processes by manipulating mitochondrial metabolism and the expression of cell surface immune proteins. The invention also relates to compositions and screening assays.

BACKGROUND OF THE INVENTION

Normal tissue develops and is maintained by normal processes of cell division and cell death. In many diseases, such as cancer, diabetes mellitus Type I, and autoimmune disease, the normal balance between cell division and cell death is disrupted causing either a rapid growth of unwanted and potentially dangerous cells or a loss of cells which are essential to maintaining the functions of tissue.

Cell division occurs by a process known as mitosis. During mitosis dividing cells use glucose cytolytically at an increased rate as the primary source for energy (ATP) production in a process referred to as glycolysis (Brand, K. A., and U. Hermfisse. 1997. Aerobic glycolysis by proliferating cells: a protective strategy against reactive oxygen species. *Faseb J* 11, no. 5:388-95). Glycolysis occurs in the cytosol and is required for mitochondrial energy production. An increased rate of glycolysis occurs when cells divide, providing more of the ATP from cytosolic glycolysis. Mitochondrial synthesis of ATP proceeds through coupling of electron transport-dependent oxido-reductive reactions to ATP synthetase (oxidative phosphorylation) (Harper, M. E. 1997. Obesity research continues to spring leaks. *Clinical Investigations in Medicine* 20, no. 4:239-244). During this process, a proton gradient is generated by the pumping of protons out of the mitochondria (Himms-Hagen, J. 1992. Brown Adipose Tissue. Obesity, eds. P. Bjorntorp and B. N. Brodoff. 1 vols. J. B. Lippincott, Philadelphia. 1 pp), increasing mitochondrial membrane potential. Uncoupling proteins (UCPs) reversibly uncouple oxidative phosphorylation from electron transport and thereby can decrease mitochondrial membrane potential (Harper, M. E. 1997. Obesity research continues to spring leaks. *Clinical Investigations in Medicine* 20, no. 4:239-244). Elevating glucose concentrations can increase mitochondrial membrane potential (Harper, M. E. 1997. Obesity research continues to spring leaks. *Clinical Investigations in Medicine* 20, no. 4:239-244).

Cell death is a physiologic process that ensures homeostasis is maintained between cell production and cell turnover in self-renewing tissues and is essential to the proper functioning of the immune system. Physiological cell death occurs through the processes of apoptosis and necrosis. The boundaries between these processes, once thought to be distinct, have blurred with the explosion of information on the role of cell death in development, tissue modeling, regenerative processes, and in the immune system. However, it is widely accepted that necrotic cell death (sometimes called oncosis) typically results in the osmotic rupture of a cell, followed by an inflammatory response, while apoptotic death involves cell shrinkage, fragmentation of the cell, and phagocytosis of the fragments often without inflammation. Most cells die in a form of suicide characteristically apoptotic and tightly regulated by complex signals (Zakeri, Z., W. Bursch, M. Tenniswood, and R. A. Lockshin. 1995. Cell Death: Programmed, apoptosis, necrosis, or other. *Cell Death and Differentiation* 2:87-96). Apoptotic cell death is particularly important in the reticulo-endothelial system where the balance between mitosis and cell death may determine the effectiveness and the nature of an immune response (Zakeri, Z., W. Bursch, M. Tenniswood, and R. A. Lockshin. 1995. Cell Death: Programmed, apoptosis, necrosis, or other. *Cell Death and Differentiation* 2:87-96). Failure results in autoimmune disease or in a lack of immune surveillance.

Inappropriate cell division or cell death results in serious life-threatening diseases. Diseases associated with increased cell division include cancer and atherosclerosis. Disease resulting from increased cell death include AIDS, neurodegenerative diseases (e.g., Alzheimer's disease, Parkinson's disease, amyotrophic lateral sclerosis, retinitis pigmentosa), aplastic anemia, atherosclerosis (e.g., myocardial infarction, stroke, reperfusion injury), and toxin induced liver disease. Many methods for treating these disorders have been proposed Although these diseases share the common physiological trait of either excess cell division or premature cell death, strategies for identifying potential therapeutic treatments have been individualized rather than searching for a common mechanism. It would be desirable to identify a common mechanism by which cell division could be interrupted or cell death could be promoted to treat all of these diseases.

PC12 cells, a cell line derived from rat pheochromocytoma (Greene and Tischler, 1976) have been extensively used as a model for the study of nerve growth factor used (NGF)-induced neuronal differentiation and dependency (Mills et al., 1997), and of neuronal cell apoptosis resulting from serum and/or trophic factor withdrawal (Mesner et al., 1995, Fulle et al., 1997), oxidative stress (Vinard et al., 1996) and, the addition of calcium ionophores (Fulle et al, 1997). NGF promotes differentiation, neurite outgrowth and the acquisition of a mature sympathetic neuronal morphology on PC12 cells. Withdrawal of NGF, however, results in apoptosis of the PC12 cells which is characterized by prototypic changes, i.e., chromatin degradation, nuclear fragmentation, acidification, alterations of surface lipids, cell fragmentation, blebbing and nucleosome formation (Gottlieb et al, 1997).

PC12 transfected variants such as TrkA have been developed to elucidate the role of NGF and signal transduction in neuronal function. Nerve growth factor (NGF) binds to two synergistic receptors, tyrosine kinase A (TrkA) and p75NGRF (Canossa et al., 1996). The PC12 TrkA cell line overexpresses TrkA, a 140 kDa protein with intrinsic tyrosine kinase activity (Kaplan et al., 1991) and responds more vigorously than native PC12 cells to NGF stimulation. It is believed that the NGF-TrkA complex acts as a messenger that delivers the growth signal from axon terminals to sympathetic neuronal cell bodies (Riccio et al., 1997).

Epidermal growth factor (EGF) has different effects on PC12 cells than NGF. When tenative PC12 cells are treated with EGF they are induced to undergo proliferation rather than differentiation. In contrast, EGF stimulation of the v-Crk and TrkA cell lines induce neuronal differentiation (Teng et al., 1995).

Fas, a member of the tumor necrosis receptor family that includes the nerve growth factor receptor, mediates apoptotic cell death in several instances, including TCR (T cell receptor)/CD3-induced T cell activation (Nagata et. Al., Science). When the Fas molecule interacts with Fas ligand or an appropriate anti-Fas antibody, cellular death can ensue (Gottlieb et al., 1997). Fas was originally described on the membrane surface of hematopoietic lineage cells (Itoh et al., 1991), but its presence has been documented on endothelial cells (Richardson et al., 1994), hepatocytes (Tanaka et al., 1998) and oligodendrocytes in multiple sclerosis lesions (Bonetti and Raine, 1997).

The B7 molecules, B7.1 (CD80) and B7.2 (CD86) are known for their ability to co-stimulate T cell proliferation (Linsley et al., 1991), the production of interleukin-2 (Freeman et al., 1992) and the expression of interleukin-2 receptors (Razi-Wolf et al., 1996). Expression of these co-stimulatory molecules on immune cells also may play an important role in the pathogenesis and response to several bacterial, parasitic and viral infections as well as autoimmune disease (Reiser and Stadecker, 1996) such as systemic lupus erythematosus (Folzenlogen et al., 1997), experimental allergic encephalomyelitis (Perrin et al., 1996) and in the rejection phase of alloimmune responses (Akalin et al., 1997).

B7.1 and B7.2 are members of the immunoglobulin gene superfamily and include a V-like and a C2-like extracellular domain. Although originally described on B cells, B7.1 and B7.2 have also been described on monocytes, dendritic cells and activated T cells (June et al., 1994). B7.1 (CD80) and particularly B7.2 (CD86) are upregulated on the B lymphocyte surface of patients with systemic lupus erythematosus (SLE) (Folzenlogen at al., 1997).

SUMMARY OF THE INVENTION

The invention involves the finding that mitochondrial metabolism plays an essential role in regulating cellular division and cell death occurring in various diseases. It was found according to the invention that the status of the cellular proton motor force which can be assessed by the coupling relationship between electron transport and oxidative phosphorylation plays an important role in the signal which determines whether a cell will undergo cellular division, cellular differentiation or cellular death. This finding has important implications for treating diseases associated with excessive cellular division, aberrant differentiation, and premature cellular death, e.g., for the treatment of cancers, autoimmune disease, neurodegenerative diseases, etc.

It was also found according to the invention that the expression of immune recognition molecules on the surface of cells is important in regulating the processes of cell division, differentiation and apoptosis occurring in various diseases. It was discovered, for instance, according to the invention that the expression of immune recognition molecules on the surface of a cell correlates with the ability of the cell to undergo differentiation. For instance, upon removal of NGF from a nerve cell, the surface expression of B7 molecules is down regulated and the nerve cell undergoes apoptosis. The induction kinetics and expression of Fas, B7.1 and B7.2 molecules on the membrane surface of differentiated PC12 cells and its mutants, and TrkA cells have been examined and are described in the Examples below.

The invention includes the discovery that neural differentiation and apoptosis are regulated through interaction of the immune recognition molecules on the nerve cell surface with an NGF producing cell that expresses the counterpart surface immune recognition molecule, likely CD28 or CTLA4. The interaction between the nerve cell and the NGF producing cell causes the NGF producing cell to release NGF into the local environment. This NGF then stimulates the nerve cell to undergo nerve cell differentiation and innervation.

Several cell surface proteins have previously been identified as cell death proteins. These proteins are believed to be involved in initiating a signal which instructs the cell to die. Cell death proteins include for example Fas/CD95 (Trauth et al., Science 245:301, 1989), tumor necrosis factor receptors, immune cell receptors such as CD40, OX40, CD27 and 4-1BB (Smith et al., Cell 76:959, 1994), and RIP (U.S. Pat. No. 5,674,734). These proteins are believed to be important mediators of cell death. These mediators, however, do not always instruct a cell to die. In some cases these mediators actually instruct a cell to undergo cell division. Prior to the instant invention the mechanism causing the dual functionality of these cell death proteins was not understood. It was discovered according to the invention, that the intracellular environment and particularly the status of the proton motor force and source of fuel for mitochondrial metabolism determines whether stimulation of the cell death protein will lead to a signal for death or cell division.

It was also discovered according to the invention that the regulation of cell surface expression of major histocompatibility complex (MHC) class II and co-stimulatory molecules B7-1 and B7-2 can be manipulated by regulating the intracellular dissipation of proton motor force which can be assessed in terms of mitochondrial membrane potential. Under conditions of low mitochondrial membrane potential (electron transport and oxidative phosphorylation are uncoupled), cells use non-glucose carbon sources for mitochondrial oxygen consumption (e.g., fatty acids or amino acids) and the surface expression of MHC class II and co-stimulatory molecules B7-1 and B7-2 is increased. Under conditions of high mitochondrial membrane potential (electron transport and oxidative phosphorylation are relatively more coupled and glucose is being used as a mitochondrial carbon source) the surface expression of MHC class II and co-stimulatory molecules B7-1 and B7-2 is decreased.

In one aspect the invention is a method for decreasing mitochondrial membrane potential in a mammalian cell. The method involves the step of administering an MHC class II HLA-DR ligand to the mammalian cell to selectively engage MHC class II HLA-DR on the surface of the cell in an amount effective to decrease mitochondrial membrane potential in the mammalian cell, wherein the mammalian cell is not an antigen presenting cell. In one embodiment MHC class II HLA-DR is expressed on the surface of the mammalian cell. In another embodiment the method involves the step of contacting the mammalian cell with an amount of an MHC class II HLA-DR inducing agent effective to induce the expression of MHC class II HLA-DR on the surface of the mammalian cell.

The mammalian cell may be any type of cell other than an antigen presenting cell. In one embodiment the mammalian cell is a tumor cell. Preferable the MHC class II HLA-DR ligand is administered to the tumor cell in vivo in an amount effective for causing cell lysis of the tumor cell. When the mammalian cell is a tumor cell, however, in some embodiments the MHC class II HLA-DR inducing agent does not include adriamycin and gamma interferon. In other embodiments when the mammalian cell is a tumor cell the MHC class II HLA-DR inducing agent does not include adriamycin and gamma interferon.

According to another aspect of the invention a method for decreasing mitochondrial membrane potential in a mammalian cell is provided. The method involves the step of contacting the mammalian cell with an amount of an MHC class II HLA-DR inducing agent effective to induce the expression of MHC class II HLA-DR on the surface of the mammalian cell, wherein the mammalian cell is not an antigen presenting cell.

The invention in another aspect is a method for increasing mitochondrial membrane potential in a mammalian cell. The method involves the step of administering an MHC class II HLA-DP/DQ ligand to the mammalian cell to selectively engage MHC class II HLA-DP/DQ on the surface of the cell in an amount effective to increase mitochondrial membrane potential in the mammalian cell. In this aspect of the invention the mammalian cell is not an antigen presenting cell.

In one embodiment MHC class II HLA-DP/DQ is expressed on the surface of the mammalian cell. In another embodiment the invention includes the step of contacting the mammalian cell with an amount of an MHC class II HLA-DP/DQ inducing agent effective to induce the expression of MHC class II HLA-DP/DQ on the surface of the mammalian cell.

According to another embodiment the mammalian cell is a pancreatic β cell of a type I diabetic and wherein the MHC class II HLA-DP/DQ ligand is administered to the pancreatic β cell in vivo.

The methods of the invention are useful for inducing cell division, cell lysis, cell differentiation and cell apoptosis, depending on the metabolic condition of the cell. In one aspect the invention is a method for inducing lysis of a mammalian cell. The method includes the steps of contacting the mammalian cell with an amount of an MHC class II HLA-DR inducing agent effective to induce the expression of MHC class II HLA-DR on the surface of the mammalian cell, and contacting the MHC class II HLA-DR on the surface of the mammalian cell with an amount of an MHC class II HLA-DR ligand effective for causing lysis of the mammalian cell.

In one embodiment the MHC class II HLA-DR ligand is an endogenous MHC class II HLA-DR ligand and the step of contacting the mammalian cell with the MHC class II HLA-DR ligand is a passive step. In another embodiment the step of contacting the mammalian cell with the MHC class II HLA-DR ligand is an active step.

The mammalian cell may be any type of cell other than an antigen presenting cell. The mammalian cell is a tumor cell in another embodiment. Preferably the MHC class II HLA-DR ligand is administered to the tumor cell in vivo in an amount effective for causing cell lysis of the tumor cell. When the mammalian cell is a tumor cell, however, the MHC class II HLA-DR inducing agent does not include adriamycin and gamma interferon.

In one aspect the invention is a method for inducing cell lysis in a tumor cell. The method involves the steps of contacting a tumor cell with an amount of an MHC class II HLA-DR inducing agent effective to induce the expression of MHC class II HLA-DR on the surface of the tumor cell, and contacting the MHC class II HLA-DR on the surface of the tumor cell with an amount of an MHC class II HLA-DR ligand effective for causing cell lysis of the tumor cell.

The MHC class II HLA-DR inducing agent is any agent which induces expression of MHC class II HLA-DR on a cell surface. Preferably the inducing agent is selected from the group consisting of adriamycin, gamma interferon, bacterial byproducts such as lipopolysaccharides, mycobacterial antigens such as BCG, a UCP expression vector, a TCRαβ engagement molecule and a fatty acid. Once the MHC class II HLA-DR is expressed on the surface of the cell an MHC class II HLA-DR ligand can interact with the MHC class II HLA-DR and initiate cell lysis. Preferably the MHC class II HLA-DR ligand is selected from the group consisting of an anti-MHC class II HLA-DR antibody, CD4 molecules, αβ T cell receptor molecules, γδ T cell receptor molecules and a MHC class II HLA-DR binding peptide.

In one embodiment the MHC class II HLA-DR inducing agent and the MHC class II HLA-DR ligand are administered simultaneously. In another embodiment the MHC class II HLA-DR inducing agent and the MHC class II HLA-DR ligand are administered orally. In yet another embodiment the MHC class II HLA-DR inducing agent and the MHC class II HLA-DR ligand are administered locally.

In another aspect the invention is a method for inducing cell lysis in a tumor cell by contacting a tumor cell with an amount of an MHC class II HLA-DR inducing agent effective to induce the expression of MHC class II HLA-DR on the surface of the tumor cell in the presence of an MHC class II HLA-DR ligand. Preferably the MHC class II HLA-DR ligand is an MHC class II HLA-DR expressing cell. In one embodiment the inducing agent is selected from the group consisting of adriamycin, gamma interferon, bacterial byproducts such as lipopolysaccharides, mycobacterial antigens such as BCG, a UCP expression vector, a TCRαβ engagement molecule and a fatty acid.

In another embodiment the MHC class II HLA-DR inducing agent and the MHC class II HLA-DR ligand are administered orally. In yet another embodiment the MHC class II HLA-DR inducing agent and the MHC class II HLA-DR ligand are administered locally.

According to another aspect of the invention a method for inducing apoptosis in a tumor cell is provided. The method involves the steps of contacting a tumor cell with an amount of a metabolic modifying agent, which when exposed to a cell causes coupling of electron transport and oxidative phosphorylation, effective to increase the mitochondrial membrane potential in the tumor cell, and contacting the tumor cell with an amount of an apoptotic chemotherapeutic agent effective for inducing apoptosis in the tumor cell.

The metabolic modifying agent is added to the tumor cell to induce coupling of electron transport and oxidative phosphorylation. Preferably the metabolic modifying agent is selected from the group consisting of glucose, phorbol myristate acetate in combination with ionomycin, MHC class II HLA-DP/DQ ligand, GDP, CD40 binding peptide, UCP antisense, dominant negative UCP, sodium acetate, and staurosporine. Once electron transport is coupled to oxidative phosphorylation, Fas expression is induced on the cell surface and a apoptotic chemotherapeutic agent can be added to induce apoptosis of the tumor cell. In one embodiment the apoptotic chemotherapeutic agent is selected from the group consisting of adriamycin, cytarabine, doxorubicin, and methotrexate.

In one embodiment the metabolic modifying agent and the apoptotic chemotherapeutic agent are administered simultaneously. In another embodiment the metabolic modifying agent and the apoptotic chemotherapeutic agent are administered orally. In yet another embodiment the metabolic modifying agent and the apoptotic chemotherapeutic agent are administered locally.

In one embodiment the tumor cell is resistant to the apoptotic chemotherapeutic agent. In another embodiment the tumor cell is sensitive to the apoptotic chemotherapeutic agent, and wherein the amount of metabolic modifying agent is effective to increase mitochondrial membrane potential and the amount of apoptotic chemotherapeutic agent is effective to inhibit the proliferation of the tumor cell when the mitochondrial membrane potential is increased.

According to yet another aspect of the invention a method for decreasing mitochondrial membrane potential in a cell of a subject is provided. The method includes the step of administering an MHC class II HLA-DR ligand to the subject to selectively engage MHC class II HLA-DR on the surface of the cell in an amount effective to decrease mitochondrial membrane potential in the mammalian cell. In one embodiment the method is performed in vivo. In another embodiment the method is performed ex vivo. In this aspect of the invention mammalian cells include but are not limited to antigen presenting cells, T cells, and tumor cells.

In yet another aspect the invention is a method for increasing mitochondrial membrane potential in a mammalian cell expressing MHC class II HLA-DP/DQ. The method includes the steps of administering an MHC class II HLA-DP/DQ ligand to the mammalian cell to selectively engage MHC class II HLA-DP/DQ on the surface of the cell in an amount effective to increase mitochondrial membrane potential in the mammalian cell.

In one embodiment the mammalian cell is a pancreatic β cell of a type II diabetic and wherein the MHC class II HLA-DP/DQ ligand is administered to the pancreatic β cell in vivo.

According to another aspect the invention is a method for decreasing mitochondrial membrane potential in a mammalian cell expressing MHC class II HLA-DR. The method involves the steps of administering an MHC class II HLA-DR ligand to the mammalian cell to selectively engage MHC class II HLA-DR on the surface of the cell in an amount effective to decrease mitochondrial membrane potential in the mammalian cell. Preferably the mammalian cell is a pancreatic β cell of a type I diabetic and wherein the MHC class II HLA-DR ligand is administered to the pancreatic β cell in vivo. In one embodiment the mammalian cell is a tumor cell and wherein the MHC class II HLA-DR ligand is administered to the tumor cell in vivo.

The invention in another aspect is a method for treating a subject having a tumor sensitive to treatment with a combination of an apoptotic chemotherapeutic agent and a metabolic modifying agent. The method includes the steps of administering to a subject in need of such treatment an apoptotic chemotherapeutic agent and a metabolic modifying agent in a combined amount effective to inhibit growth of the tumor, said combined amount being an amount of apoptotic chemotherapeutic agent and an amount of metabolic modifying agent, wherein the amount of metabolic modifying agent is effective to increase mitochondrial membrane potential and the amount of apoptotic chemotherapeutic agent is effective to inhibit the proliferation of the tumor cell when the mitochondrial membrane potential is increased.

According to another aspect the invention is a method for treating a subject having a tumor that is resistant to chemotherapy. The method includes the steps of administering to the subject an amount of an apoptotic chemotherapeutic agent, and administering substantially simultaneously therewith an amount of a metabolic modifying agent, wherein said amounts when administered are effective for inhibiting growth of the tumor.

According to another aspect the invention is a method for inducing the expression of immune recognition molecules on a cell surface. The method involves the step of contacting a cell with an amount of a metabolic inhibition agent effective to decrease mitochondrial membrane potential, wherein a decrease in mitochondrial membrane potential causes induction of the expression of immune recognition molecules on the cell surface. Preferably the immune recognition molecule is selected from the group consisting of MHC class II, B7-1, B7-2, and CD-40. Preferably the metabolic inhibition agent is selected from the group consisting of apoptotic chemotherapeutic agents, bacterial byproducts, mycobacterial antigens, UCP expression vectors, and fatty acids.

The invention in another aspect is a method for inhibiting pancreatic β cell death in a Type I diabetic. The progression of pancreatic β cell death in type I diabetes involves two steps. The first phase of type I diabetes is the insulitis phase which results when membrane potential is increased, the β cells become cell surface Fas positive, but Fas-death insensitive. During this stage it is desirable to decrease the membrane potential and cause the cells to use fatty acids for fuel and become cell surface Fas negative. If the diabetes is not treated during the first phase then it progresses to a second phase. During the second phase the membrane potential is decreased and the β cell is induced to die if it remains cell surface Fas positive. Thus the invention contemplates a two phase approach to the treatment of type I diabetes. In the first phase a subject is treated to decrease the membrane potential of the pancreatic β cells to prevent or reduce the chance that the disease will progress from the insulitis phase to the cell death phase. In the case when the disease has already progressed to the cell death phase a subject is treated to increase the membrane potential of their pancreatic β cells. This method involves the steps of contacting a pancreatic β cell of a Type I diabetic with an amount of a metabolic modifying agent effective to increase mitochondrial membrane potential in the pancreatic β cell. Preferably the metabolic modifying agent is selected from the group consisting of glucose, phorbol myristate acetate in combination with ionomycin, MHC class II HLA-DP/DQ ligand, GDP, CD40 binding peptide, sodium acetate, UCP antisense, dominant negative UCP, and staurosporine. The method is also useful for promoting wound healing in a diabetic. In one embodiment the metabolic modifying agent is infused with an antagonist of glucose, 2 deoxyglucose.

According to another aspect of the invention a method for inhibiting pancreatic β cell death in a Type I diabetic is provided. The method involves the step of contacting a pancreatic β cell of a Type I diabetic with an amount of a Fas binding agent effective to inhibit selective engagement of Fas on the surface of the pancreatic β cell.

According to yet another aspect of the invention a method for inducing pancreatic β cell death in a Type II diabetic is provided. The method includes the steps of contacting a pancreatic β cell of a Type II diabetic with an amount of an MHC class II HLA-DR inducing agent effective to induce the expression of the MHC class II HLA-DR on the surface of the pancreatic β cell, and selectively engaging the MHC class II HLA-DR by contacting the cell with an MHC class II HLA-DR ligand effective to induce pancreatic β cell death. The MHC class II HLA-DR inducing agent is selected from the group consisting of adriamycin, gamma interferon, bacterial byproducts such as lipopolysaccharides, mycobacterial antigens such as BCG, a UCP expression vector, a TCRαβ engagement molecule and a fatty acid in one embodiment.

In another aspect the invention is a method for treating a subject having autoimmune disease to reduce associated cell death. The method includes the step of administering an amount of a γδ binding peptide effective to specifically bind to and inactivate γδ cells in the subject, wherein the inactivation of the γδ cells inhibits cell death associated with autoimmune disease. Preferably the γδ binding peptide is an anti-γδ antibody.

According to another aspect of the invention a method for treating a subject having autoimmune disease to reduce associated cell death is provided. The method includes the steps of providing an extracellular environment having a high concentration of glucose to stimulate induction of MHC class II HLA-DP/DQ and a low concentration of fatty acids to inhibit induction of MHC class II HLA-DR, wherein surface expression of MHC class II HLA-DP/DQ is indicative of reduced cell death associated with autoimmune disease.

A method for screening a subject for susceptibility to atherosclerosis is provide according to another aspect of the invention. The method includes the steps of isolating a cell selected from the group consisting of peripheral blood lymphocyte and skin from a subject and detecting the presence of an MHC marker selected from the group consisting of an MHC class II HLA-DP/DQ and MHC class II HLA-DR on the surface of the cell selected from the group consisting of peripheral blood lymphocyte and skin, wherein the presence of MHC class II HLA-DP/DQ is indicative of susceptibility to atherosclerosis and the presence of MHC class II HLA-DR is indicative of resistance to atherosclerosis.

The invention in another aspect is a method for selectively killing a Fas ligand bearing tumor cell. The method includes the step of contacting the a Fas ligand bearing tumor cell with acetate in an amount effective to induce Fas associated cell death. In one embodiment the a Fas ligand bearing tumor cell is contacted with the acetate in an amount effective to sensitize the cell to a chemotherapeutic agent and further comprising the step of contacting the cell with a chemotherapeutic agent. A preferred chemotherapeutic agent is methotrexate. The method may also involve the step of administering a Fas ligand to the a Fas ligand bearing tumor cell. In a preferred embodiment the Fas ligand bearing tumor cell is selected from the group consisting of a melanoma cell and a colon carcinoma cell.

In another aspect the invention is a method for promoting a Th1 immune response. The method involves the step of administering to a subject who has been exposed to an antigen an effective amount for inducing a Th1 immune response of a MHC class II HLA-DR inducing agent to induce DR on a T cell. In one embodiment the MHC class II HLA-DR inducing agent is fatty acid.

The invention also includes screening assays. A method for screening a tumor cell of a subject for susceptibility to treatment with a chemotherapeutic agent, is one aspect of the invention. The assay includes at least the following steps: isolating a tumor cell from a subject; exposing the tumor cell to a chemotherapeutic agent; and, detecting the presence of a cell death marker selected from the group consisting of a Fas molecule on the surface of the tumor cell, a B7 molecule on the surface of the tumor cell, an MHC class II HLA-DR on the surface of the tumor cell, and a mitochondrial membrane potential indicative of cellular coupling wherein the presence of the cell death marker indicates that the cell is susceptible to treatment with a chemotherapeutic agent.

In one embodiment the cell death marker is a Fas molecule on the surface of the tumor cell and wherein the method comprises the step of contacting the Fas molecule with a detection reagent that selectively binds to the Fas molecule to detect the presence of the Fas molecule. In another embodiment the cell death marker is a MHC class II HLA-DR molecule on the surface of the tumor cell and wherein the method comprises the step of contacting the MHC class II HLA-DR molecule with a detection reagent that selectively binds to the MHC class II HLA-DR molecule to detect the presence of the MHC class II HLA-DR molecule.

Another screening assay of the invention is a method for identifying an anti-tumor drug for killing a tumor cell of a subject and includes the steps of isolating a tumor cell from a subject; detecting the presence of a cell death marker selected from the group consisting of a Fas molecule on the surface of the tumor cell, a B7 molecule on the surface of the tumor cell, an MHC class II HLA-DR on the surface of the tumor cell, and a mitochondrial membrane potential indicative of cellular coupling; exposing the tumor cell to a putative drug; and, detecting any change in the presence of the cell death marker to determine whether the putative drug is an anti-tumor drug capable of killing the tumor cell of the subject.

a plurality of tumor cells is isolated from the subject and the plurality of tumor cells is screened with a panel of putative drugs in one embodiment of the assay. In another embodiment the change in the presence of the cell death marker is detected by contacting the tumor cell with a cell death ligand attached to a solid support. Preferably the cell death ligand is a Fas ligand.

Yet another assay of the invention is a method for screening a subject for susceptibility to disease. This method involves the steps of isolating a cell selected from the group consisting of peripheral blood lymphocyte and skin from a subject; and, detecting the presence of an MHC marker selected from the group consisting of an MHC class II HLA-DP/DQ, B7-2, B7-1 and MHC class II HLA-DR on the surface of the cell, wherein the presence of MHC class II HLA-DP/DQ is indicative of susceptibility to atherosclerosis and resistance to autoimmune disease and the presence of MHC class II HLA-DR, B7-2, or B7-1 is indicative of resistance to atherosclerosis and susceptibility to autoimmune disease.

The invention also encompasses kits. One kit of the invention is a kit for screening a subject for susceptibility to disease. The kit includes a container housing a first binding compound that selectively binds to a protein selected from the group consisting of B7-2, B7-1 and MHC class II HLA-DR; a container housing a second binding compound that selectively binds to a MHC class II HLA-DP/DQ protein; and instructions for determining whether an isolated cell of a subject selectively interacts with the first or second binding compound, wherein the presence of MHC class II HLA-DP/DQ on the cell surface which interacts with the second compound is indicative of susceptibility to atherosclerosis and resistance to autoimmune disease and the presence of MHC class II HLA-DR on the cell surface which interacts with the first compound is indicative of resistance to atherosclerosis and susceptibility to autoimmune disease.

Another kit of the invention is a kit for screening a tumor cell of a subject for susceptibility to treatment with a chemotherapeutic agent. The kit includes a container housing a cell death marker detection reagent; and instructions for using the cell death marker detection reagent for detecting the presence of a cell death marker selected from the group consisting of a Fas molecule on the surface of the tumor cell, an MHC class II HLA-DR on the surface of the tumor cell, and a mitochondrial membrane potential indicative of cellular coupling wherein the presence of the cell death marker indicates that the cell is susceptible to treatment with a chemotherapeutic agent.

In some embodiments the kit also includes a container housing a chemotherapeutic agent or a panel of chemotherapeutic agents, housed in separate compartments. In other embodiments the kit also includes a cell death ligand. Preferably the cell death ligan is coated on a solid surface. In another preferred embodiment the cell death ligand is a Fas ligand.

The invention in another aspect is a method for selectively killing a cell. The method involves the step of contacting the cell with a nucleic acid selected form the group consisting of a UCP anti-sense nucleic acid and a UCP dominant-negative nucleic acid in an amount effect to inhibit UCP function.

In one embodiment the cell death marker is a Fas molecule on the surface of the tumor cell and wherein the method comprises the step of contacting the Fas molecule with a detection reagent that selectively binds to the Fas molecule to detect the presence of the Fas molecule. In another embodiment the cell death marker is a MHC class II HLA-DR molecule on the surface of the tumor cell and wherein the method comprises the step of contacting the MHC class II HLA-DR molecule with a detection reagent that selectively binds to the MHC class II HLA-DR molecule to detect the presence of the MHC class II HLA-DR molecule.

In another aspect the invention is a composition of a metabolic modifying agent and an apoptotic chemotherapeutic agent. Preferably the metabolic modifying agent is selected from the group consisting of glucose, phorbol myristate acetate in combination with ionomycin, MHC class II HLA-DP/DQ ligand, GDP, CD40 binding peptide, sodium acetate, UCP antisense, dominant negative UCP, and staurosporine. In a preferred embodiment the apoptotic chemotherapeutic agent is selected from the group consisting of adriamycin, cytarabine, doxorubicin, and methotrexate.

In one embodiment the metabolic modifying agent and the apoptotic chemotherapeutic agent are present in an amount effective to inhibit the proliferation of a tumor cell. In another embodiment the composition includes a pharmaceutically acceptable carrier.

The invention according to another aspect is a composition of an MHC class II HLA-DR inducing agent and an MHC class II HLA-DR ligand. In one embodiment the MHC class II HLA-DR inducing agent is selected from the group consisting of adriamycin, gamma interferon, bacterial byproducts such as lipopolysaccharides, mycobacterial antigens such as BCG, a UCP expression vector, a TCR$\alpha\beta$ engagement molecule and a fatty acid. In another embodiment the MHC class II HLA-DR ligand is selected from the group consisting of an anti-MHC class II HLA-DR antibody, CD4 molecules, $\alpha\beta$ T cell receptor molecules, $\gamma\delta$ T cell receptor molecules and a MHC class II HLA-DR binding peptide. According to yet another embodiment the MHC class II HLA-DR inducing agent and the MHC class II HLA-DR ligand are present in an amount effective to lyse a tumor cell. The composition may be formulated in a pharmaceutically acceptable carrier.

The invention also includes the discovery that neural differentiation and apoptosis are regulated through interaction of the immune recognition molecules on the nerve cell surface with an NGF producing cell that expresses the counterpart surface immune recognition molecule, likely CD28 or CTLA4. The interaction between the nerve cell and the NGF producing cell causes the NGF producing cell to release NGF into the local environment. This NGF then stimulates the nerve cell to undergo nerve cell differentiation and innervation.

The invention in other aspects relates to methods and products for regulating nerve cell growth, differentiation, and apoptosis. In one aspect the invention is a method for inducing nerve cell differentiation. The method includes the steps of contacting a nerve cell with an amount of a B7 inducing agent effective to induce the expression of B7 on the surface of the nerve cell, and exposing the nerve cell to a neural activating cell to cause differentiation of the nerve cell.

In another aspect the invention is a method for inducing nerve cell differentiation. The method involves the step of contacting a nerve cell with an amount of a B7 inducing agent effective to induce the expression of B7 on the surface of the nerve cell in the presence of an endogenous neural activating cell.

In some embodiments the B7 inducing agent is adriamycin, gamma interferon, a fatty acid, a lipoprotein, an anti-MHC class II HLA-DR antibody, a MHC class II HLA-DR binding peptide, a B7 expression vector, or a UCP expression vector.

In another embodiment the method also includes the step of contacting the nerve cell with an amount of a metabolic modifying agent, which when exposed to a cell causes increased coupling of electron transport and oxidative phosphorylation, effective to prevent dissipation of proton motor force in the nerve cell prior to contacting the nerve cell with the B7 inducing agent. In some embodiments the metabolic modifying agent is glucose, phorbol myristate acetate in combination with ionomycin, MHC class II HLA-DP/DQ ligand, GDP, CD40 binding peptide, sodium acetate, UCP antisense, dominant negative UCP, and staurosporine. In other embodiments the neural activating cell is a T cell, a macrophage, or a dendritic cell.

In yet another embodiment the method includes the step of administering a fatty acid to the nerve cell to stop cell division.

In yet another embodiment the method includes the step of inducing the expression of a receptor for nerve growth factor.

According to another aspect the invention is a method for inducing apoptosis in a nerve cell. The method includes the steps of contacting a nerve cell with an amount of a metabolic modifying agent, which when exposed to a nerve cell causes an increase in coupling of electron transport and oxidative phosphorylation, effective to prevent dissipation of proton motor force in the nerve cell, and contacting a neural activating cell with an amount of a B7 receptor blocking agent effective for inducing apoptosis in the nerve cell.

The metabolic modifying agent, in various embodiments, is glucose, phorbol myristate acetate in combination with ionomycin, MHC class II HLA-DP/DQ ligand, GDP, CD40 binding peptide, sodium acetate, UCP antisense, dominant negative UCP, or staurosporine. In various other embodiments the B7 receptor blocking agent is an anti-CD28 antibody, CD28 binding peptide, CTLA4 analog, anti-CTLA4 antibody, or CTLA4 binding peptide.

The invention also includes compositions related to the above methods. In one aspect the invention is a composition of a metabolic modifying agent and a B7 receptor blocking agent.

The metabolic modifying agent, in various embodiments, is glucose, phorbol myristate acetate in combination with ionomycin, MHC class II HLA-DP/DQ ligand, GDP, CD40 binding peptide, sodium acetate, UCP antisense, dominant negative UCP, or staurosporine. In various other embodiments the B7 receptor blocking agent is an anti-CD28 antibody, CD28 binding peptide, CTLA4 analog, anti-CTLA4 antibody, or CTLA4 binding peptide.

In another embodiment the metabolic modifying agent and the B7 receptor blocking agent are present in an amount effective to induce apoptosis of a nerve cell. In yet another embodiment the composition also includes a pharmaceutically acceptable carrier.

A composition of a B7 inducing agent and a CD28 inducing agent is provided in another aspect of the invention.

In some embodiments the B7 inducing agent is adriamycin, gamma interferon, bacterial byproducts such as lipopolysaccharides and lipoproteins, mycobacterial antigens such as BCG, and fatty acids, an anti-MHC class II HLA-DR antibody, a MHC class II HLA-DR binding peptide, a B7 expression vector, or a UCP expression vector. In other embodiments the CD28 inducing agent is a T cell receptor engagement molecule, CD3 engagement molecule, IL4, or a CD28 expression vector. In yet another embodiment the composition also includes a pharmaceutically acceptable carrier.

According to another aspect of the invention a method for re-innervating an injured tissue is provided. The method includes the step of implanting a B7 expressing nerve cell in the injured tissue, wherein the implanted B7 expressing nerve cell will undergo neuronal differentiation in the presence of a neural activating cell in the injured tissue to re-innervate the injured tissue.

In one embodiment the B7 expressing nerve cell constitutively expresses B7. In another embodiment the B7 expressing nerve cell is a nerve cell which constitutively expresses a UCP gene. In yet another embodiment the B7 expressing nerve cell is a nerve cell which constitutively expresses a B7 gene.

The method in another embodiment includes the step of administering a B7 inducing agent effective to induce endogenous B7 expression on the surface of the nerve cell.

The injured tissue may be any tissue in which a nerve is damaged. In one embodiment the injured tissue is a spinal chord. In another embodiment the injured tissue is a severed limb.

A method for treating a neurodegenerative disorder is provided according to another aspect of the invention. The method includes the step of administering an amount of a B7 inducing agent effective to induce the expression of B7 on the surface of a nerve cell.

In some embodiments the B7 inducing agent is adriamycin, gamma interferon, bacterial byproducts such as lipopolysaccharides and lipoproteins, mycobacterial antigens such as BCG, and fatty acids, an anti-MHC class II HLA-DR antibody, a MHC class II HLA-DR binding peptide, a B7 expression vector, or a UCP expression vector.

The method may also include the step of inducing expression of CD28 on the surface of a neural activating cell. Preferably the neural activating cell is a T cell. In other preferred embodiments the neural activating cell is a macrophage, a B cell or a dendritic cell.

In yet another embodiment the neurodegenerative disorder is selected from the group consisting of paralysis, Parkinson's disease, Alzheimer's disease, amyotrophic lateral sclerosis, and multiple sclerosis.

According to another aspect the invention is a method for selectively killing a cell. The method includes the step of contacting the cell with a nucleic acid selected form the group consisting of a UCP anti-sense nucleic acid and a UCP dominant-negative nucleic acid in an amount effect to inhibit UCP function.

In other aspects the invention is a method for selectively killing a tumor cell. The method includes the steps of contacting the tumor cell with acetate in an amount effective to induce cell surface Fas expression, and administering a Fas ligand to the tumor cell in an amount effective to induce Fas associated cell death. In one embodiment the tumor cell is contacted with the acetate in an amount effective to sensitize the cell to a chemotherapeutic agent and further comprising the step of contacting the cell with an apoptopic chemotherapeutic agent.

A method for selectively killing a tumor cell is provided according to another aspect of the invention. The method includes the step of contacting the tumor cell with a compound selected from the group consisting of acetate, GDP and an apoptopic chemotherapeutic agent in an amount effective to kill the tumor cell.

Each of the limitations of the invention can encompass various embodiments of the invention. It is, therefore, anticipated that each of the limitations of the invention involving any one element or combinations of elements can be included in each method and product.

These and other aspects of the invention are described in greater detail below.

BRIEF DESCRIPTION OF THE FIGURES

The present invention may be more easily and completely understood when taken in conjunction with the accompanying figures.

FIG. 25 is a histogram depicting the constitutive expression or lack thereof of cell surface molecules Fas (panels A, D, G), B7.1 (panels B, E H) and B7.2 (panels C, F, I) in PC12 cells (panels A, B, C), PC12/TrkA cells (Panels D, E, F) and PC12/v-Crk Cells (panels G, H, I).

BRIEF DESCRIPTION OF THE SEQUENCES

Figure 1A:
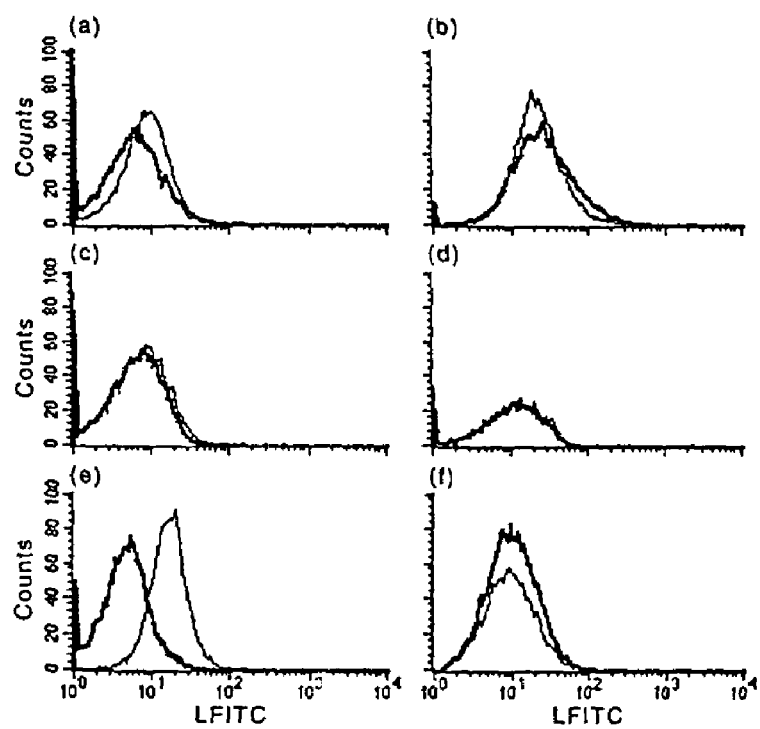
FIG. 1 shows a flow cytometric analysis of Fas expression.

SEQ ID NO:1 is the nucleotide sequence of the human B7 (B7.1) cDNA with GenBank Acc. no.:M27533.

SEQ ID NO:2 is the predicted amino acid sequence of the translation product of human B7 (B7.1) cDNA (SEQ ID NO:1).

SEQ ID NO:3 is the nucleotide sequence of the human B7.2 cDNA with GenBank Acc. no.U04343.

SEQ ID NO:4 is the predicted amino acid sequence of the translation product of human B7.2 cDNA (SEQ ID NO:3).

SEQ ID NO:5 is the nucleotide sequence of the human uncoupling (UCP-1) cDNA with GenBank Acc. no.U28480.

SEQ ID NO:6 is the predicted amino acid sequence of the translation product of human uncoupling cDNA (UCP-1) (SEQ ID NO:5).

SEQ ID NO:7 is the nucleotide sequence of the human uncoupling (UCP-2) cDNA with GenBank Acc. no.U82819.

SEQ ID NO:8 is the predicted amino acid sequence of the translation product of human uncoupling cDNA (UCP-2) (SEQ ID NO:7).

SEQ ID NO:9 is the nucleotide sequence of the human uncoupling (UCP-3S) cDNA with GenBank Acc. no.U82818.

SEQ ID NO:10 is the predicted amino acid sequence of the translation product of human uncoupling cDNA (UCP-3S) (SEQ ID NO:9).

SEQ ID NO:11 is the nucleotide sequence of the human CD28 cDNA with GenBank Acc. no.J02988.

SEQ ID NO:12 is the predicted amino acid sequence of the translation product of the human CD28 cDNA (SEQ ID NO:11).

SEQ ID NO:13 is the amino acid sequence of a peptide.

DETAILED DESCRIPTION OF THE INVENTION

The invention relates to methods and products involving the control of cell division, differentiation, death, and apoptosis by the regulation of cell surface immune recognition molecules. It was discovered according to one aspect of the invention that proton motor force (assessed as mitochondrial metabolism) is integrally related to the regulation of cellular division and cellular apoptosis. The ability to manipulate mitochondrial metabolic processes has led to the development of methods for treating diseases associated with excessive cellular proliferation or premature cellular death. Additionally, the ability to manipulate the expression of cell surface immune recognition molecules such that a nerve cell can stimulate local NGF production from an NGF producing cell has led to the development of methods for treating neurodegenerative diseases associated with premature cellular death. It was also discovered according to the invention that the regulation of proton motor force (mitochondrial metabolism) is directly related to the expression of these cell surface immune recognition molecules involved in the signaling process of cell death and in immune response signaling, and thus can be manipulated as one method for regulating the expression of the immune recognition molecules. The ability to control the expression of these cell surface molecules is a useful and powerful technique for therapeutically manipulating the processes of cellular death, apoptosis, differentiation and proliferation. Monitoring the expression of these proteins is also useful for screening assays to assess disease states as well as the mitochondrial metabolic status of cells.

Based on all these discoveries the invention includes in some aspects methods for increasing or decreasing the mitochondrial membrane potential in a mammalian cell. The ability to manipulate the mitochondrial membrane potential of a cell provides the ability to control the fate of the cell. When the membrane potential of a cell is decreased and the cell is caused to use fatty acids for fuel the cell can interpret a signal as a signal for cell death. If the membrane potential of a cell is increased, however, and the cell is using glucose for fuel, the same signal can be interpreted as a signal to divide rather than for cell death. The invention encompasses mechanisms for controlling these complex interactions to regulate the processes of cellular death and division.

One method for causing a decrease in mitochondrial membrane potential and a switch to the use of fatty acids as fuel is by inducing the expression of MHC class II HLA-DR on the surface of the cell. If low amounts of MHC class II HLA-DR are already expressed on the surface the cell can be contacted with an MHC class II HLA-DR ligand to cause a further decrease in the mitochondrial membrane potential. When a cell has been induced to express MHC class II HLA-DR on the cell surface such that the electron transport is uncoupled and the cell is using fatty acids for fuel and the cell is contacted with a MHC class II HLA-DR ligand, then the cell generally will interpret that signal as a cell death signal, and cause cell lysis.

The invention also encompasses methods for causing an increase in mitochondrial membrane potential. This increase, accompanied by the use of glucose as fuel is accomplished in some aspects by inducing the expression of MHC class II HLA-DPDQ on the surface of the cell. If low amounts of MHC class II HLA-DPDQ are already expressed on the surface the cell can be contacted with an MHC class II HLA-DPDQ ligand to cause a further increase in the mitochondrial membrane potential and an increase in coupling of electron transport and oxidative phosphorylation. When a cell has been induced to express MHC class II HLA-DPDQ on the cell surface such that the electron transport is relatively coupled and the cell is using glucose for fuel and the cell is contacted with a MHC class II HLA-DPDQ ligand, then the cell generally will interpret that signal as a cell division signal, and cause cellular division.

The methods of the invention have broad utility in regulating mammalian cell growth and death in vitro, in vivo and ex vivo. Because mammalian cells utilize the basic process of mitochondrial metabolism in regulating their own growth and differentiation, any type of mammalian cell can be manipulated according to the methods of the invention. When the methods for increasing or decreasing mitochondrial metabolism are performed in vitro by contacting an MHC class II HLA-DPDQ or -DR expressing cell with an MHC class II HLA-DPDQ or -D ligand, respectively, the methods are not performed on antigen presenting cells. When the same methods are performed ex vivo or in vivo they may however, be performed on antigen presenting cells as well as any other type of mammalian cell. An "antigen presenting cell" is used herein consistently with its well known meaning in the art and includes, for instance, dendritic cells, macrophage, etc. The in vitro methods of the invention are useful for a variety of purposes. For instance, the methods of the invention may be useful for identifying drugs which have an effect, such as a preventative effect, on cellular division or death by contacting cells which are caused by the manipulations of the invention to undergo cellular division or death.

In addition to the in vitro methods, the methods of the invention may be performed in vivo or ex vivo in a subject to manipulate one or more cell types within the subject. An "ex vivo" method as used herein is a method which involves isolation of a cell from a subject, manipulation of the cell outside of the body, and reimplantation of the manipulated cell into the subject. The ex vivo procedure may be used on autologous or heterologous cells, but is preferably used on autologous cells. In preferred embodiments, the ex vivo method is performed on cells that are isolated from bodily fluids such as peripheral blood or bone marrow, but may be isolated from any source of cells. When returned to the subject, the manipulated cell will be programmed for cell death or division, depending on the treatment to which it was exposed. Ex vivo manipulation of cells has been described in several references in the art, including Engleman, E. G., 1997, *Cytotechnology*, 25:1; Van Schooten, W., et al., 1997, *Molecular Medicine Today*, June, 255; Steinman, R. M., 1996, *Experimental Hematology*, 24, 849; and Gluckman, J. C., 1997, *Cytokines, Cellular and Molecular Therapy*, 3:187. The ex vivo activation of cells of the invention may be performed by routine ex vivo manipulation steps known in the art. In vivo methods are also well known in the art. A subject as used herein means humans, primates, horses, cows, pigs, sheep, goats, dogs, cats and rodents. The invention thus is useful for therapeutic purposes and also is useful for research purposes such as testing in animal or in vitro models of medical, physiological or metabolic pathways or conditions.

In preferred embodiments of the invention the mammalian cell is a tumor cell The method is useful for inducing cell lysis in many types of mammalian cells but is particularly useful for inducing cell lysis in a tumor cell. A "tumor cell" as used herein is a cell which is undergoing unwanted mitotic proliferation. A tumor cell when used in the in vitro aspects of the invention can be isolated from a tumor within a subject or may be part of an established cell line. A tumor cell in a subject may be part of any type of cancer. Cancers include but are not limited to biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor.

In the aspects of the invention that the mammalian cell is a tumor cell and the cell is only treated with an MHC class II HLA-DR inducing agent but not an MHC class II HLA-DR ligand the MHC class II HLA-DR inducing agent does not include adriamycin and gamma interferon. When the MHC class II HLA-DR inducing agent is adriamycin or gamma interferon the method of lysing the tumor cell requires the additional step of contacting the tumor cell with an MHC class II HLA-DR ligand to cause cell lysis.

Cell lysis is the necrotic death of a cell which occurs by osmotic rupture.

As used herein an "MHC class II HLA-DR inducing agent" is an agent which causes MHC class II HLA-DR to be expressed on the cell surface. Preferably the MHC class II HLA-DR inducing agent is a pharmacological agent that causes uncoupling of electron transport and oxidative phosphorylation, resulting in reduced mitochondrial membrane potential within the cell. MHC class II HLA-DR inducing agents include but are not limited to adriamycin, gamma interferon, bacterial byproducts such as lipopolysaccharides, mycobacterial antigens such as BCG, a UCP expression vector, a TCRαβ engagement molecule and a fatty acid. Although gamma interferon induces expression of both MHC class II HLA-DR and MHC class II HLA-DP/DQ it can still be used in combination with an MHC class II HLA-DR ligand which selectively binds to MHC class II HLA-DR and not MHC class II HLA-DP/DQ. The MHC class II HLA-DR inducing agent is an isolated molecule. An isolated molecule is one which has been removed from its natural surroundings and formulated for administration to an organism. Adriamycin, gamma interferon, bacterial byproducts such as lipopolysaccharides, mycobacterial antigens such as BCG are all well known compounds which can be purchased from a variety of commercial sources. UCP expression vector can be prepared by methods well known in the art, such methods are described in detail below. Fatty acids are also well known compounds that can be purchased commercially from many sources. Preferred fatty acids include but are not limited to oleic acid, palmitate, and myristic acid. A "TCRαβ engagement molecule" as used herein refers to any compound that can bind to and cause cell surface crosslinking of CD4 and the αβT cell receptor (αβTCR). Such compounds are known in the art. For instance heterobifunctional antibodies are capable of crosslinking CD4 and αβTCR by interacting with both molecules on the surface of the cell. Other CD4/αβTCR binding molecules can be identified with routine experimentation and are also encompassed by the term TCRαβ engagement molecule. Routine screening methods for identifying such binding molecules are set forth below.

MHC class II HLA-DR refers to a subregion of the human major histocompatibility class II genetic locus. As used herein the "MHC class II HLA-DR" is the protein expressed on the surface of a cell which corresponds to the MHC class II HLA-DR genetic locus. Although the term HLA-DR refers to the human subclass of MHC, the invention is intended to encompass the corresponding subclass of MHC in other species, which have different nomenclature, such as the IE region in the corresponding subclass in the mouse.

As used herein an "MHC class II HLA-DR ligand" is a molecule which binds to MHC class II HLA-DR and stimulates an MHC class II HLA-DR specific intracellular signal stimulating cell lysis. MHC class II HLA-DR ligands are MHC class II HLA-DR binding peptides which cause cell surface crosslinking of MHC class II HLA-DR molecules. Such ligands are well known in the art and include but are not limited to anti-MHC class II HLA-DR antibodies such as those commercially available from Becton Dickinson and many other sources, CD4 peptides, γδ T cell receptor (TCR) peptides, αβ TCR peptides, and other binding peptides, optionally bound to a delivery vehicle such as a liposome. CD4 peptides, γδTCR peptides, and αβTCR peptides are well known cell surface molecules. These peptides can be used as a ligand in a soluble form or may be attached or conjugated to a carrier such as a liposome or particle (other chemical/physical vectors useful for this purpose are discussed below). In addition to these known binding peptides other MHC class II HLA-DR binding peptides can be identified with routine experimentation and are also encompassed by the term MHC class II HLA-DR ligand. Routine screening methods for identifying such binding molecules are set forth below.

Cell lysis can be assessed by any method known in the art for making such measurements. For example cell lysis can be determined by direct histological analysis, comparison of intact cell numbers using a coulter counter, and flow cytometry. These methods are well known in the art and some are described in more detail in the examples section below.

The "MHC class II HLA-DR ligand" as used herein is an isolated molecule. An isolated molecule is one which has been removed from its natural surroundings and formulated for administration to an organism.

The methods of the invention in some aspects may also be performed using endogenous MHC class II HLA-DR ligand. An "endogenous MHC class II HLA-DR ligand" is different than an "MHC class II HLA-DR ligand" used above which is an isolated composition. For instance the endogenous MHC class II HLA-DR ligand may be a cell having a cell surface MHC class II HLA-DR binding peptide. In this case the method would only include the step of contacting a tumor cell with an amount of an MHC class II HLA-DR inducing agent effective to induce the expression of MHC class II HLA-DR on the surface of the tumor cell in the presence of an endogenous MHC class II HLA-DR ligand.

When the endogenous MHC class II HLA-DR ligand is a cell having a cell surface MHC class II HLA-DR binding peptide which is already present in interactive proximity to the MHC class II HLA-DR, the cell does not have to be manually brought into contact with the MHC class II HLA-DR.

Another aspect of the invention involves the induction of apoptosis in a tumor cell rather than cell lysis. In both apoptosis and cell lysis the cell dies but the processes occur through different mechanisms and when the cell is in a different metabolic state. As described above, when the methods of the invention are performed to induce cell lysis in a tumor cell the cell is in an uncoupled state. When the methods of the invention are performed to induce apoptosis the cell is caused to assume a coupled state. The method for inducing apoptosis in a tumor cell involves the steps of contacting a tumor cell with an amount of a metabolic modifying agent, which when exposed to a cell causes coupling of electron transport and oxidative phosphorylation, effective to increase the mitochondrial membrane potential in the tumor cell, and contacting the tumor cell with an amount of a chemotherapeutic agent effective for inducing apoptosis in the tumor cell.

Apoptosis is a process of cell death in which the cell undergoes shrinkage and fragmentation, followed by phagocytosis of the cell fragments. Apoptosis is well known in the art and can be assessed by any art recognized method. For example apoptosis is easily determined using flow cytometry, which distinguishes between live and dead cells. Flow cytometry is described in more detail in the Examples below.

As used herein a "metabolic modifying agent" is an agent which when exposed to a cell causes coupling of electron transport and oxidative phosphorylation, resulting in increased mitochondrial membrane potential within the cell. Metabolic modifying agents include but are not limited to glucose, sodium acetate, phorbol myristate acetate in combination with ionomycin, MHC class II HLA-DP/DQ ligand, guanosine diphosphate (GDP), CD40 binding peptide, sodium acetate, UCP antisense, dominant negative UCP, and staurosporine. Glucose, phorbol myristate acetate, ionomycin, GDP, and staurosporine are all well known commercially available compounds which can be obtained form many sources. CD40 binding peptides are any peptide molecules which interact with CD40, causing CD40 crosslinking on a cell surface. These molecules include, for example, CD40 ligand, which is a well known molecule. CD40 binding peptides are not limited to CD40 ligand, however, but include other molecules which can be identified with routine experimentation. Routine screening methods for identifying such binding molecules are set forth below. UCP antisense molecules and dominant negative UCP molecules are also known in the art and are described in more detail below.

MHC class II HLA-DP/DQ refers to another subregion of the human major histocompatibility class II genetic locus. As used herein the "MHC class II HLA-DP/DQ" is the protein expressed on the surface of a cell which corresponds to the MHC class II HLA-DP/DQ genetic locus. Although the term HLA-DP/DQ refers to the human subclass of MHC, the invention is intended to encompass the corresponding subclass of MHC in other species, which have different nomenclature, such as the IA region in the subclass in the mouse.

As used herein an "MHC class II HLA-DP/DQ ligand" is a molecule which binds to MHC class II HLA-DP/DQ and stimulates an MHC class II HLA-DP/DQ specific intracellular signal stimulating coupling of electron transport and oxidative phosphorylation resulting in increased mitochondrial membrane potential. MHC class II HLA-DP/DQ ligands include but are not limited to anti-MHC class II HLA-DP/DQ ligand antibodies, other binding peptides, and cells having a cell surface MHC class II HLA-DP/DQ binding antigen. When the MHC class II HLA-DP/DQ ligand is a cell having a cell surface MHC class II HLA-DP/DQ binding antigen which is already present in interactive proximity to the MHC class II HLA-DP/DQ, the cell does not have to be manually brought into contact with the MHC class II HLA-DP/DQ.

As used herein, the term "dissipation of proton motor force" refers to the relative amount of protons in the mitochondria. It can be assessed by measuring mitochondrial membrane potential. As used herein "mitochondrial membrane potential" is the pressure on the inside of the mitochondrial cell membrane measured relative to the extracellular fluid which is created by the generation and dissipation of charge within the mitochondria. The mitochondrial membrane potential is maintained by the energy generating system of the mitochondria. In most tissues electron transport is coupled to oxidative phosphorylation resulting in the production of ATP from glucose. Uncoupling proteins (UCPs) can cause the reversible uncoupling of electron transport and oxidative phosphorylation, which leads to a decrease in the mitochondrial membrane potential. Other tissue, often referred to as the immuno-privileged tissue such as the brain, testis, ovary, eye, and pancreatic β cells, express UCPs which cause electron transport to be uncoupled to oxidative phosphorylation under normal conditions. In these tissues glucose cannot be converted to ATP while the UCP is active because of the uncoupling and the energy produced is converted into other energy forms such as heat and released. If the metabolic processing systems in these tissues are caused to undergo coupling the membrane potential would increase.

The absolute levels of the mitochondrial membrane potential vary depending on the cell or tissue type. As used herein an "increase in mitochondrial membrane potential" is an increase relative to the normal status of the cell being examined and results from the prevention of dissipation of proton motor force. "Prevention" as used herein refers to a decrease or reduction in the amount of dissipation that would ordinarily occur in the absence of the stimulus applied according to the methods of the invention to cause coupling. If electron transport and oxidative phosphorylation are normally uncoupled within the cell then the baseline potential will be relatively low and when the ATP generating systems are coupled an increase in mitochondrial membrane potential from that baseline level is observed. Likewise, a "decrease in mitochondrial membrane potential" is a decrease relative to the normal status of the cell being examined and results from the dissipation of proton motor force. If electron transport and oxidative phosphorylation are normally coupled within the cell then the baseline potential will be relatively high and when the ATP generating systems are uncoupled a decrease in mitochondrial membrane potential from that baseline level is observed.

Changes in mitochondrial membrane potential can be assessed by any method known in the art for making such measurements. For example the mitochondrial membrane potential may be measured cytometrically by incubating cells for 20 minutes at room temperature with 5 mg/ml JC-1$^{39}$ a fluorescent probe able to bind mitochondria. The aggregation state and consequently the fluorescence emission of JC-1 changes as the mitochondrial membrane potential is altered. Valinomycin, which collapses the mitochondrial membrane potential can be used as a positive control treatment. Flow cytometry permits the examination of up to four fluorescent markers concurrently. This method is described in more detail in the Examples section below In addition to examining the mitochondrial membrane potential, studies can be performed to determine the rate of glucose utilization and oxidation and measurements of proton leak can be assessed by a top-down elasticity analysis, each of which is described in more detail in the Examples below.

The relationship between mitochondrial metabolism and cell surface Fas expression is important to the methods of the invention. When a cell is coupled Fas is expressed on the cell surface and when a cell is uncoupled Fas generally is transported to intracellular stores. When a cell is coupled and Fas is on the surface engagement of Fas sends a signal to the cell instructing the cell to undergo cellular division. If a chemotherapeutic agent is added then the signal is changed to a signal which instructs the cell to undergo apoptosis. When a cell is uncoupled and ordinarily Fas is not expressed on the cell surface. Under certain disease conditions such as Type I diabetes (discussed in more detail below), or when the cell has been irradiated Fas can be expressed on the surface of uncoupled cells. When this occurs engagement of Fas sends a signal to the cell to die.

An "apoptotic chemotherapeutic agent" as used herein is a group of molecules which function by a variety of mechanisms to induce apoptosis in rapidly dividing cells. Apoptotic chemotherapeutic agents are a class of chemotherapeutic agents which are well known to those of skill in the art. Chemotherapeutic agents include those agents disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc (Health Professions Division), incorporated herein by reference. Suitable chemotherapeutic agents may have various mechanisms of action. The classes of suitable chemotherapeutic agents include (a) Alkylating Agents such as nitrogen mustard (e.g. mechlorethamine, cylophosphamide, ifosfamide, melphalan, chlorambucil), ethylenimines and methylmelamines (e.g. hexamethylmelamine, thiotepa), alkyl sulfonates (e.g. busulfan), nitrosoureas (e.g. carmustine which is also known as BCNU, lomustine which is also known as CCNU semustine which is also known as methyl-CCNU, chlorozoticin, streptozocin), and triazines (e.g. dicarbazine which is also known as DTIC); (b) Antimetabolites such as folic acid analogs (e.g. methotrexate), pyrimidine analogs (e.g. 5-fluorouracil floxuridine, cytarabine, and azauridine and its prodrug form azaribine), and purine analogs and related materials (e.g. 6-mercaptopurine, 6-thioguanine, pentostatin); (c) Natural Products such as the vinca alkaloids (e.g. vinblastine, Vincristine), epipodophyllotoxins (e.g. etoposide, teniposide), antibiotics (e.g dactinomycin which is also known as actinomycin-D, daunorubicin, doxorubicin, bleomycin, plicamycin, mitomycin, epirubicin, which is 4-epidoxorubicin, idarubicin which is 4-dimethoxydaunorubicin, and mitoxanthrone), enzymes (e.g L-asparaginase), and biological response modifiers (e.g. Interferon alfa); (d) Miscellaneous Agents such as the platinum coordination complexes (e.g. cisplatin, carboplatin), substituted ureas (e.g. hydroxyurea), methylhydrazine derivatives (e.g. procarbazine), adrenocortical suppressants (e.g. mitotane, aminoglutethimide) taxol; (e) Hormones and Antagonists such as adrenocorticosteroids (e.g. prednisone or the like), progestins (e.g. hydroxyprogesterone caproate, medroxyprogesterone acetate, megestrol acetate), estrogens (e.g. diethylstilbestrol, ethinyl estradiol, and the like), antiestrogens (e.g. tamoxifen), androgens (e.g. testosterone propionate, fluoxymesterone, and the like), antiandrogens (e.g. flutamide), and gonadotropin-releasing hormone analogs (e.g. leuprolide) and (F) DNA damaging compounds such as adriamycin.

In addition to the methods of manipulating cells, the invention is also useful for screening cells such as tumor cells to determine if those cells are susceptible to cellular division or cellular death, alone or in conjunction with treatment with a chemotherapeutic agent or other cell signal and kits for performing these screening assays. The screening method can be accomplished by isolating a tumor cell from a subject and exposing the tumor cell to a chemotherapeutic agent (preferably several different doses of several different chemotherapeutic agents can be screened at a time). Then the presence of a cell death marker can be detected. The level of the cell death marker indicates that the cell is susceptible to treatment with a chemotherapeutic agent.

As used herein a "cell death marker" is a cell surface molecule which indicates that the cell is susceptible to cell death. A variety of cell death markers exist but the preferred cell death markers useful according to the invention include a Fas molecule on the surface of the tumor cell, an MHC class II HLA-DR on the surface of the tumor cell, and a mitochondrial membrane potential indicative of cellular coupling. The Fas and MHC molecules can be detected by using a detection reagent that bind to the protein, such as an antibody.

The screening methods are particularly useful for determining if a tumor is sensitive to a chemotherapeutic agent. A tumor, however, may initially be sensitive to a particular chemotherapeutic agent and then as the therapy progresses the tumor may become resistant to that chemotherapeutic agent. The methods of the invention can be used to prevent the tumor from becoming sensitive to a chemotherapeutic agent during therapy. The method involves the steps of administering to a subject in need of such treatment a chemotherapeutic agent and a metabolic modifying agent in a combined amount effective to inhibit growth of the tumor. The metabolic modifying agent causes the electron transport and oxidative phosphorylation processes to be coupled and therefore effects an increased mitochondrial membrane potential in the cell. As the cell is held in this coupled state Fas is expressed on the surface and the chemotherapeutic agent can stimulate Fas mediated apoptosis. The cells will be prevented from becoming resistant.

The combined amount of metabolic modifying agent and apoptotic chemotherapeutic agent effective to inhibit growth of the tumor cell is that amount is effective to inhibit the proliferation of the tumor cell when the mitochondrial membrane potential is increased. An effective amount means that amount necessary to delay the onset of, inhibit the progression of, halt altogether the onset or progression of or diagnose the particular condition being treated. In general, an effective amount for treating a tumor cell is that amount necessary to halt the proliferation of the cell. In one embodiment, the effective amount is that amount necessary to kill the cell. In general, an effective amount for treating cancer will be that amount necessary to favorably affect mammalian cancer cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

In some cases the screening assay may indicate that the tumor is mostly resistant to a chemotherapeutic agent. Resistant tumors may also be treated by the methods of the invention. One aspect of the invention involves the discovery that resistant tumors cells have a mitochondrial metabolic state in which electron transport is uncoupled from oxidative phosphorylation. It was discovered according to the invention that by altering the metabolic state of the tumor cell and thereby causing electron transport to be coupled to oxidative phosphorylation it is possible to cause the resistant cell to revert such that it becomes sensitive to chemotherapy. The method is performed by administering to the subject an amount of a chemotherapeutic agent, and substantially simultaneously therewith an amount of a metabolic modifying agent which together are effective for inhibiting growth of the tumor. The metabolic modifying agent causes electron transport in the cell to be coupled to oxidative phosphorylation. As discussed above once these processes are coupled Fas is expressed on the surface and the cell becomes susceptible to apoptosis induced by the chemotherapeutic agent.

Other screening assays can be performed according to the invention to identify an anti-tumor drug for killing a tumor cell of a subject. These assays are accomplished by isolating a tumor cell from a subject; detecting the presence of a cell death marker selected from the group consisting of a Fas molecule on the surface of the tumor cell, a B7 molecule on the surface of the tumor cell, an MHC class II HLA-DR on the surface of the tumor cell, and a mitochondrial membrane potential indicative of cellular coupling; exposing the tumor cell to a putative drug; and, detecting any change in the presence of the cell death marker to determine whether the putative drug is an anti-tumor drug capable of killing the tumor cell of the subject. This assay may be performed on one or a plurality of tumor cells and with a single drug or with a panel of drugs.

The assay can be performed using routine equipment known in the art. For instance the change in the presence of the cell death marker can be detected by contacting the tumor cell with a cell death ligand attached to a solid support.

The invention also encompasses kits for screening a subject for susceptibility to disease. This kit includes at least a container housing a first binding compound that selectively binds to a protein selected from the group consisting of B7-2, B7-1 and MHC class II HLA-DR; a container housing a second binding compound that selectively binds to a MHC class II HLA-DP/DQ protein; and instructions for determining whether an isolated cell of a subject selectively interacts with the first or second binding compound, wherein the presence of MHC class II HLA-DP/DQ on the cell surface which interacts with the second compound is indicative of susceptibility to atherosclerosis and resistance to autoimmune disease and the presence of MHC class II HLA-DR on the cell surface which interacts with the first compound is indicative of resistance to atherosclerosis and susceptibility to autoimmune disease.

Other kits include kits for screening a tumor cell of a subject for susceptibility to treatment with a chemotherapeutic agent. These kits include a container housing a cell death marker detection reagent; and instructions for using the cell death marker detection reagent for detecting the presence of a cell death marker selected from the group consisting of a Fas molecule on the surface of the tumor cell, an MHC class II HLA-DR on the surface of the tumor cell, and a mitochondrial membrane potential indicative of cellular coupling wherein the presence of the cell death marker indicates that the cell is susceptible to treatment with a chemotherapeutic agent. The kit may also include a container housing a chemotherapeutic agent. Optionally, the kit may include a panel of chemotherapeutic agents, housed in separate compartments.

The invention also involves the discovery that mitochondrial metabolic regulation is directly related to the expression of immune recognition molecules on a cell surface. As used herein "immune recognition molecules" are cell surface proteins which mark a cell for identification by immune cells. Immune recognition molecules include but are not limited to MHC, and in particular MHC class II HLA-DR, B7-1, B7-2 and CD-40. When the mitochondrial metabolic status of the cell is such that the electron transport is uncoupled to oxidative phosphorylation the cell surface expression of the immune recognition molecules is increased. When the mitochondrial metabolic status of the cell is such that the electron transport is coupled to oxidative phosphorylation the cell surface expression of the immune recognition molecules is decreased. Under these conditions, however, the expression of MHC class II HLA-DP/DQ is actually increased. For purposes of this patent application MHC class II HLA-DP/DQ is not defined as an immune recognition molecule.

Based on these findings the invention encompasses a method for inducing the expression of immune recognition molecules on a cell surface. The method involves contacting the cell with an amount of a metabolic inhibition agent effective to decrease mitochondrial membrane potential, wherein a decrease in mitochondrial membrane potential causes induction of the expression of immune recognition molecules on the cell surface.

A "metabolic inhibition agent" as used herein is an agent that causes electron transport to become uncoupled from oxidative phosphorylation, and includes for example apoptotic chemotherapeutic agents, bacterial byproducts, mycobacterial antigens, UCP expression vectors, and fatty acids.

Diabetes mellitus, which encompasses both Type I (i.e., Insulin Dependent Diabetes Mellitus (IDDM)) and Type II (i.e., Non-Insulin Dependent Diabetes Mellitus (NIDDM)), is known to affect more than one hundred million individuals worldwide. Although the exact cause of diabetes is unclear it is believed that diabetes may arise from any of a variety of physiological conditions such as genetic syndromes, viral infections, age related deterioration of structures responsible for maintaining the glycemic response, pancreatic disease, hormonal abnormalities, certain drugs or chemicals, insulin receptor abnormalities, etc. A "type I diabetic" is a subject who has diabetes mellitus caused by a destruction of beta cells in the pancreas. Type I diabetics require daily insulin administration which may be reduced but not altogether eliminated by careful restriction of diet.

Neither the genetic/environmental influences nor the inherent β cell characteristics that trigger immune-mediated destruction are completely understood. However, two features that are pivotal in susceptibility to β cell destruction are the expression of the cell surface molecule Fas and the metabolic state of the β cells. Fas can induce mitosis or apoptosis depending on the cell and the experimental circumstances. During the prediabetic stage of Type 1 diabetes, a β cell compensatory hypersecretion of insulin occurs and this process is accompanied by cell surface expression of the molecule Fas. When NOD mice, an animal model for Type 1 diabetes, are crossed with mice having the lpr mutation (Fas deficient), the animals are resistant to disease. In addition, destruction of β cells in the NOD accelerates when Fas Ligand is placed on the insulin promotor.

It has been discovered according to the invention that changes in mitochondrial metabolic processes that alter mitochondrial membrane potential and Fas expression contribute to Fas-induced β cell destruction. β cell glucose-induced insulin secretion depends on increased intracellular ATP. The mitochondrial synthesis of ATP occurs through coupling of electron transport-dependent oxido-reductive reactions to ATP synthetase (oxidative phosphorylation). During this process, a proton gradient is generated by the pumping of protons out of the mitochondria increasing mitochondrial membrane potential. Uncoupling proteins (UCPs) reversibly uncouple oxidative phosphorylation from electron transport decreasing mitochondrial membrane potential. Normal pancreatic β cell are in an uncoupled state and do not express Fas on their cell surface. As diabetes progresses to a first stage in which the patient is sick but before the pancreatic β cell are destroyed, the patients pancreatic β cells become coupled and express Fas on the cell surface. The disease then progresses to the stage when pancreatic β cell begin to be killed. Before the cells are killed the metabolic state changes again to uncoupled and Fas is still expressed on the surface. When the cell is in an uncoupled state and Fas is expressed on the cell surface the cell is killed as soon as Fas is engaged without the need for any other agents.

The methods of the invention include a method for inhibiting pancreatic β cell death in a Type I diabetic by altering the mitochondrial metabolic state. The method is performed by contacting a pancreatic β cell of a Type I diabetic with an amount of a metabolic modifying agent effective to increase mitochondrial membrane potential in the pancreatic β cell. The metabolic modifying agent causes the pancreatic β cell to revert to or remain in a coupled state. Although these cells are not in the normal state of a pancreatic β cell, they are not killed and the patients organ is not destroyed.

Another method for inhibiting the death of a pancreatic β cell in a Type I diabetic can be accomplished by contacting a pancreatic β cell of a Type I diabetic with an amount of a Fas binding agent effective to inhibit selective engagement of Fas on the surface of the pancreatic β cell. By inhibiting the selective engagement of Fas on the cell surface and allowing the cell to remain in the uncoupled state the cell will remain healthy and have the phenotype of a normal pancreatic β cell.

The Fas binding agents which are useful according to the invention are those molecules which bind to Fas but do not activate it. Fas binding agents can be identified by screening libraries using the extracellular regions of Fas, such as the screening methods described below. Fas binding agents then can easily be tested without undue experimentation in vitro for their ability to bind Fas but not induce cell death in uncoupled cells. Uncoupled cells can be prepared according to the methods described above. Fas can be induced to be expressed on the surface of cells using irradiation as has previously been identified in the prior art. Once uncoupled cells expressing Fas have been developed potential Fas binding agents can be incubated with these cells and cell lysis can be assayed by the methods described herein or by other methods known in the art.

The invention is also useful for treating type II diabetics. A "type II diabetic" is a subject who has diabetes mellitus caused by abnormal insulin secretion and/or resistance to insulin action in target tissues. The physiological problem which occurs in a Type II diabetic is very different than that which occurs in a type I diabetic. In type II diabetes the pancreatic β cells undergo excessive proliferation. It is desirable to inhibit proliferation of these cells.

One method for inducing pancreatic β cell death in a Type II diabetic involves the step of contacting a pancreatic β cell of a Type II diabetic with an amount of an MHC class II HLA-DR inducing agent effective to induce the expression of the MHC class II HLA-DR on the surface of the pancreatic β cell, and selectively engaging the MHC class II HLA-DR by contacting the cell with an MHC class II HLA-DR ligand effective to induce pancreatic β cell death.

Another finding according to the invention was that mitochondrial metabolism and the related expression of MHC class II on the surface of a cell is indicative of the susceptibility of the host of that cell to developing atherosclerosis, autoimmune disease or multiple sclerosis. When electron transport and oxidative phosphorylation are in a coupled state in a cell the cell expresses MHC class II HLA-DP/DQ on the surface. When electron transport and oxidative phosphorylation are in an uncoupled state in a cell the cell expresses MHC class II HLA-DR on the surface. A cell in a coupled state that has MHC class II HLA-DP/DQ on the surface will be stimulated to divide when the MHC class II HLA-DP/DQ is engaged. A cell in an uncoupled state that has MHC class II HLA-DR on the surface will be stimulated to lyse when the MHC class II HLA-DR is engaged.

These different metabolic states of the cell have been found according to the invention to be predictive of an individuals susceptibility to developing disease. When the cells of a subject are coupled and express MHC class II HLA-DP/DQ on the surface the subject is susceptible to developing atherosclerosis. When the cells of a subject are uncoupled and express MHC class II HLA-DR on the surface the subject is susceptible to developing autoimmune disease.

The invention encompasses methods for screening a subject for susceptibility to atherosclerosis. These methods involve the steps of isolating a cell which is useful for screening such as a peripheral blood lymphocyte or a skin cell from a subject and detecting the presence of an MHC marker selected from the group consisting of an MHC class II HLA-DP/DQ, B7-2, B7-1 and MHC class II HLA-DR on the surface of peripheral blood lymphocyte, wherein the presence of MHC class II HLA-DP/DQ is indicative of susceptibility to atherosclerosis and the presence of MHC class II HLA-DR is indicative of resistance to atherosclerosis.

Atherosclerosis is a group of diseases affecting the cardiovascular system and includes myocardial infarction, stroke, angina pectoris and peripheral cardiovascular disease. Despite significant advices in therapy, cardiovascular disease remains the single most common cause of morbidity and mortality in the developed world. Many individuals are susceptible to developing future cardiovascular disorders, and this susceptibility has usually been defined in terms of risk factors such as family history of premature ischemic heart disease, hyperlipidemia, cigarette smoking, hypertension, low HDL cholesterol, diabetes mellitus, hyperinsulinemia, abdominal obesity, and high lipoprotein. The invention includes a new method for determining an individuals susceptibility to developing atherosclerosis. As used herein susceptibility to atherosclerosis indicates a likelihood of 10% greater than the average of developing atherosclerosis.

The invention also encompasses methods for screening a subject for susceptibility to autoimmune disease. These methods involve the steps of isolating a peripheral blood lymphocyte from a subject and detecting the presence of an MHC marker selected from the group consisting of an MHC class II HLA-DP/DQ, B7-2, B7-1 and MHC class II HLA-DR on the surface of peripheral blood lymphocyte, wherein the presence of MHC class II HLA-DR is indicative of susceptibility to autoimmune disease and the presence of MHC class II HLA-DP/DQ is indicative of resistance to autoimmune disease.

Autoimmune disease is a class of diseases in which an individuals own antibodies react with host tissue or in which immune effector T cells are autoreactive to endogenous self peptides and cause destruction of tissue. It is well established that MHC class II alleles act as major genetic elements in susceptibility to a variety of autoimmune diseases. These include rheumatoid arthritis, celiac disease, pemphigus vulgaris, and the prototype for autoimmune disease, systemic lupus erythematosus (SLE). The invention includes a new method for determining an individuals susceptibility to developing autoimmune disease. As used herein susceptibility to Autoimmune disease indicates a likelihood of 10% greater than the average of developing autoimmune disease.

The methods of the invention also include methods for treating a subject having autoimmune disease to reduce associated cell death. One method is based on the interaction between cells expressing MHC class II HLA-DR and γδ T cells. γδ T cells specifically recognize MHC class II HLA-DR on the surface of the cell and stimulate cell death. When the γδ T cells recognize a tissue having significant amounts of MHC class II HLA-DR these T cells become activated and proliferate in order to kill more of the recognized cells. The methods of treatment are based on the concept of eliminating the activated γδ T cells from the body. These cells can be removed by isolating a sample of peripheral blood and identifying the activated γδ T cells by assessing activation markers using flow cytometry. Antibodies can then be generated to the specific activated γδ T cells and the antibodies can be used to selectively bind to and inactivate γδ cells in the subject. This inactivation of the γδ cells inhibits cell death associated with autoimmune disease.

Similarly cells expressing cell surface MHC class II HLA-DR that are ordinarily recognized and killed by γδ T cells can be used for the treatment of diseases involving excessive cell proliferation such as glioma. The cells can be induced to undergo cell death by stimulating excess activated γδ T cells in the subject. This can be accomplished using bacterial byproducts.

It has been found according to the invention that a link exists between Fas expression, mitochondrial metabolism, and susceptibility to Fas-dependent cell death. Thus by regulating mitochondrial metabolism it is possible to control susceptibility to Fas dependent cell death. This phenomenon is described below with respect to pancreatic β cells, but is applicable to all biological systems described herein.

Type I diabetes mellitus (DM) is a pancreatic β cell-selective autoimmune disease which results in insulin deficiency. Neither the genetic/environmental influences nor the inherent β cell characteristics that trigger immune-mediated destruction are completely understood. Apoptosis has been suggested as the mechanism of β cell death in mouse models of Type I diabetes. Two features that correlate with susceptibility to β cell destruction are the metabolic state of the β cells and expression of the cell surface molecule Fas (CD95), a member of the TNF family of "death inducing" receptor/ligand pairs. During the prediabetic stage of Type I DM, a β cell glucose-dependent hypersection of insulin occurs in response to high glucose concentrations and this process is coincident with the cell surface expression of Fas. When NOD mice are crossed with mice having the lpr mutation (Fas deficient), the animals are resistant to disease. In addition, destruction of β cells in the NOD accelerates when Fas ligand is placed on the insulin promoter. In the NOD model, apoptotic β cells have been observed in the islets at 15 weeks of age which coincides with the earliest onset of diabetes as determined by blood glucose, urine glucose, and pancreatic immunoreactive insulin measurements. The incidence of apoptosis decreases by week 18 at which time 50% of the animals have overt diabetes. Virtually all of the apoptotic cells have been determined immunohistochemically to be positive for insulin production. Interestingly, apoptosis of β cells precedes the appearance of T cells in islets. The ability to upregulate Fas expression on β cells is also acquired during the early stages of Type I DM.

It is believed according to the invention that the metabolic state of the β cell determines the susceptibility of β cells to Fas mediated death. β cell glucose-induced insulin secretion depends upon increased intracellular ATP. The mitochondrial synthesis of ATP results from the coupling of electron transport-dependent oxido-reductive reactions to ATP synthetase (oxidative phosphorylation). During this process, a proton gradient is generated by the pumping of protons across the mitochondrial membrane resulting in an increase in mitochondrial membrane potential. Uncoupling proteins (UCP) can reversibly dissipate the proton gradient resulting in decreased membrane potential. Mitochondrial damage, resulting from viruses, inflammation, age, or oxidative stress, can also dissipate the proton gradient and decrease the mitochondrial membrane potential. However, in the latter case, the change in mitochondrial metabolism is irreversible. For example, increased intracellular NO production in β cells is known to alter β cell mitochondrial membrane potential and sensitize β cells to Fas-induced death. Our data (provided in the Examples below) demonstrate that β cells express intracellular UCP. Furthermore, we have shown that β cell surface Fas expression and mitochondrial membrane potential increase as a function of environmental glucose concentration. Taken together, these results are consistent with the notion that mitochondrial glucose metabolism and consequent mitochondrial membrane potential play a critical regulatory role in susceptibility to Fas-induced β cell death.

Increasing environmental glucose results in increased cell surface Fas expression and functionally coupled mitochondrial ATP synthesis, suggesting a link between mitochondrial glucose metabolism and susceptibility to Fas-induced cell death. ATP is required for insulin secretion. As glucose levels decrease, levels of cell surface Fas decrease, newly synthesized Fas is stored intracellularly and mitochondrial ATP synthesis is uncoupled from respiration and less mitochondrial ATP is produced. This is demonstrated schematically in FIG. 14. The reversibility of this process may account for the pulsatility of insulin secretion in response to nutrients. In either state, coupled or uncoupled, damaging agents such as diabetogenic viruses, inflammation, ischemia, age, or oxidative stress, may damage mitochondrial metabolism, increase cell surface Fas expression, and render the cells susceptible to Fas-induced apoptosis or oncosis, respectively. One possibility is that during the insulitis phase of Type I DM, apoptosis (on the right of the panel), which is thought to occur "silently" without additional inflammation, occurs to some of the β cells and that oncosis occurs in later stages of disease resulting from T cell mediated (FasL dependent) β cell destruction.

The invention in other aspects relates to methods for selectively killing a Fas ligand bearing tumor cell. The method involves the steps of contacting the Fas ligand bearing tumor cell with acetate in an amount effective to induce Fas associated cell death. A Fas ligand bearing tumor cell is any tumor cell which inducibly or constitutively expressed a Fas ligand on the cell surface. Such cells can easily be identified by those of skill in the art since the Fas ligand is a well known molecule. These cells include but are not limited to melanoma cells and colon carcinoma cells.

Although acetate alone is sufficient to kill a Fas ligand bearing tumor cell, the cell can also be treated with a chemotherapeutic agent and/or a Fas ligand to promotes killing. The use of these secondary compounds allows the use of less of the acetate to be used to accomplish the cell killing. The combination of acetate and chemotherapeutic agents and or Fas ligands, allows less of all three reagents to be used than would otherwise be required to kill the cell.

Additionally, tumor cells that do not express cell surface Fas ligand can also be killed by the methods of the invention. This killing can be accomplished by contacting the tumor cell with acetate in an amount effective to induce cell surface Fas expression, and administering a Fas ligand to the tumor cell in an amount effective to induce Fas associated cell death. Fas ligands are expressed on the surface of NK γδ T cells, CD4 T cells, CD8 T cells, etc.

Other methods for selectively killing a cell include contacting the cell with a nucleic acid selected form the group consisting of a UCP anti-sense nucleic acid and a UCP dominant-negative nucleic acid in an amount effect to inhibit UCP function. A cell can also be killed according to the invention by contacting the cell with a compound selected from the group consisting of acetate and GDP and an apoptopic chemotherapeutic agent in an amount effective to kill the cell.

The invention also encompasses methods for promoting a Th1 immune response. The method is performed by administering to a subject who has been exposed to an antigen an effective amount for inducing a Th1 immune response of a MHC class II HLA-DR inducing agent to induce DR on a T cell. MHC class II HLA-DR inducing agents are discussed in detail above, and include, for instance, fatty acids.

The invention in another aspect is a method for inducing nerve cell differentiation by contacting a nerve cell with an amount of a B7 inducing agent effective to induce the expression of B7 on the surface of the nerve cell and exposing the nerve cell to a neural activating cell to cause differentiation of the nerve cell.

The complex process of immune cell activation and proliferation is based on diverse interactions such as antigen presentation, cell-cell contact and soluble immune mediators e.g., cytokines or lymphokines. Many of these interactions are mediated in T- and other immune cells through surface receptors. T helper cells, for example, require for activation both the presentation of an antigen by an antigen presenting cell (APC) in association with major histocompatibility complex (MHC) and a secondary signal. The secondary signal may be a soluble factor or may involve an interaction with another set of receptors on the surface of T- and other immune cells. Antigen presentation in the absence of the secondary signal, however, is not sufficient to activate T helper cells.

The CTLA-4/CD28/B7 system is a group of proteins involved in regulating T-cell proliferation through this secondary signaling pathway. The T-cell proliferative response is controlled by the interaction of the B7 family of proteins, which are expressed on the surface of APCs, with CTLA-4 (cytotoxic T lymphocyte antigen #4) and CD28.

The B7 family of proteins is composed of structurally related glycoproteins including B7-1, B7-2, and B7-3 (Galea-Lauri et al., *Cancer Gene Therapy*, v. 3, p. 202-213 (1996); Boussiotis, et al., *Proc. Nat. Acad. Sci. USA*, v. 90, p. 11059-11063 (1993)). The different B7 proteins appear to have different expression patterns on the surface of antigen presenting cells. For example B7-2 is constitutively expressed on the surface of monocytes, whereas B7-1 is not, although B7-1 expression is induced in these cells when the cells are stimulated with interferon gamma (IFN-γ). The different expression patterns may indicate a different role for each of the B7 family members. The B7 proteins are believed to be involved in the events relating to stimulation of an immune response by its ability to interact with various immune cell surface receptors. It is believed, for example, that B7 plays a role in augmenting T-cell proliferation and cytokine production through its interaction with the CD28 receptor.

CD28, a homodimeric glycoprotein having two disulfide linked 44-kd subunits, is found on 95% of $CD4^+$ and 50% of $CD8^+$ cells. Studies using monoclonal antibodies reactive with CD28 have demonstrated that CD28 is involved in a secondary signal pathway in the activation of T-cell proliferation. Antibodies which block the interaction of CD28 with its ligand have been found to inhibit T-cell proliferation in vitro resulting in antigen specific T cell energy. (Harding et al., *Nature*, v. 356, p. 607 (1991)).

Recently a T-cell surface receptor protein, CTLA-4, having approximately 20% sequence homology to CD28 was identified. Although CTLA-4 is not endogenously expressed on T-cell surfaces, its expression is induced when CD28 interacts with B7 on the surface of an APC. Once CTLA-4 is expressed on the surface of the T-cell it is capable of interacting with B7.

It was discovered according to one aspect of the invention that nerve cells can be induced to express B7 and can interact with T- and other immune cells through B7/CD28/CTLA4 molecules. The B7 on the nerve cell surface can engage the CD28/CTLA4 on the immune cell surface to co-stimulate the immune cell, leading to activation of the immune cell. The activated immune cell then releases nerve growth factor which stimulates the nerve cell.

As used herein "B7 inducing agent" is an agent which causes B7 (and other related family members retaining sequence homology with B7) to be expressed on a nerve cell surface. In one preferred embodiment the B7 inducing agent is a pharmacological agent that causes dissipation of proton motor force such as by uncoupling of electron transport and oxidative phosphorylation, resulting in reduced mitochondrial membrane potential within the cell. B7 inducing agents which cause dissipation of the proton motor force include but are not limited to adriamycin, gamma interferon, bacterial byproducts such as lipopolysaccharides, lipoproteins BCG, fatty acids, cAMP inducing agents and a UCP expression vector. A "cAMP inducing agent" as used herein is any compound which elevates intracellular levels of cAMP. Such compounds include but are not limited to isoproterenol, epinephrine, norepinephrine, phosphodiester inhibitors, theophylline, and caffeine. In another preferred embodiment the B7 inducing agent is a B7 expression vector. Such a vector can be stably expressed in the nerve cell to produce B7 which can be expressed on the cell surface. The B7 inducing agent is an isolated molecule. An isolated molecule is one which has been removed from its natural surroundings and formulated for administration to an organism.

An "amount of a B7 inducing agent effective to induce the expression of B7 on the surface of the nerve cell" as used herein, refers to an amount which is effective to cause dissipation of a proton motor force and thus to decrease the mitochondrial membrane potential in the nerve cell. Preferably the amount is that amount which is necessary to induce the expression of at least a single B7 molecule on the cell surface.

The nerve cell is contacted with the B7 inducing agent to cause expression of B7 on the surface. As used herein, the step of contacting the cell with B7 inducing agent can be performed by any means known in the art. For instance, if the B7 inducing agent is applied in vitro, it may simply be added as part of the cellular medium to a tissue culture dish of nerve cells. If the method is performed in vivo, then the step of contacting may be performed by administering the B7 inducing agent by commonly used therapeutic techniques, such as parenteral administration, oral administration, or local administration. Other methods are well known to those of ordinary skill in the art.

According to a method of the invention the B7 expressing nerve cell is exposed to a neural activating cell. A "neural activating cell" as used herein, is a cell which is capable of producing nerve growth factor when activated and which includes a cell surface B7 receptor. As mentioned above, B7 receptors include CD28 and CTLA-4. Many cells which are the neural activating cells of the invention have been described in the prior art. These cells include, for example, T cells (including both gamma, delta and alpha-beta T cells), macrophage, dendritic cells, CTLA-4 or CD-28 expressing B cells.

A "B7 receptor" as used herein is a cell surface immune molecule which interacts with B7 on a partner cell and cases activation of the cell on which it is expressed. Preferably the B7 receptor is a CD28 molecule or a CTLA4 molecule.

The nerve cell is exposed to the neural activating cell to cause differentiation of the nerve cell. The step of exposing can be performed in vitro, by simply mixing the two populations of cells, the nerve cell and the neural activating cell. It can be accomplished in vivo by causing the accumulation of the neural activating cells in the local environment of the nerve cell. For instance, the neural activating cells may be implanted, or the local environment may be manipulated to cause accumulation of the neural activating cell. For instance, stimulating an immune response in the local environment would cause the accumulation of T cells, B cells, dendritic cells and macrophage. The neural activating cell may also be a cell which produces nerve growth factor upon activation and which is engineered to express a B7 receptor on its surface, e.g. by transfection with an inducible or constitutively expressed B7 receptor gene, such as by the methods described above.

The methods of the invention in some aspects may also be performed using an endogenous neural activating cell. For instance the endogenous neural activating cell may be a cell having a cell surface B7 receptor, such as CD28 and CTLA-4. In this case the method would only include the step of contacting a nerve cell with an amount of a B7 inducing agent effective to induce the expression of B7 on the surface of the nerve cell in the presence of a neural activating cell.

When the neural activating cell is a cell having a cell surface B7 receptor which is already present in interactive proximity to the B7, the cell does not have to be manually brought into contact with the B7 on the nerve cell.

When the nerve cell is exposed to a neural activating cell the cell surface B7 can interact with the B7 receptor to activate the neural activating cell. Once activated, the neural activating cell produces and releases nerve growth factor into the local environment. This locally produced nerve growth factor is capable of causing the nerve cell to become differentiated. Although the invention is not limited to a specific mechanism of action, applicants believe that the mechanism through which neuro-differentiation occurs is that the nerve growth factor interacts with the nerve cell surface nerve growth factor receptor such as Trk. It is also believed that engagement of the B7 on the cell surface or the induction thereof causes the expression of nerve growth factor receptors on the surface of the nerve.

In one embodiment of the invention, the receptors for nerve growth factor may be induced to be expressed on the surface of the nerve cell. Two known nerve growth factors are tyrosine, kinase A (TrkA) and p75NGRF. When these receptors interact with nerve growth factor on the surface of a nerve cell, it stimulates the cell to undergo neuronal differentiation. Expression of these receptors on the surface of the nerve cell may be performed by any method known in the art. For instance, the nerve cell may be recombinantly engineered to constitutively or inducibly express the DNA for these receptors, such as by the methods described above.

Nerve growth factor (NGF), originally described by Levi-Montalcini and Hamburger in 1953 (Levi-Montalcini and Hamburger, 1953), contains two copies of three types of polypeptides designated α, β and γ and exhibits approximately 50% of homology with other neurotrophins i.e., brain-derived neurotrophic factor (BDNF), NT-3, NT-4 and NT-5 (Siegel et al., 1994). It binds to tyrosine kinase A (TrkA) and p75NGF receptors in a synergistic manner (Canossa et al., 1996). Tyro sine kinase B (TrkB) and tyro sine kinase C (TrkC) receptors preferentially bind BDNf and NT-3 respectively (Siegel et al., 1994). Intracellular signal proteins via Src homology 2 (SH20 domain interactions such as phospholipase C-γ and the p85 sub-unit of phosphatidyl-inositol 3-kinase bind to the tyrosine-phosphorylated receptors and allow multimeric protein complexes to form and lead to the activation of specific signal transduction pathways (Hempstead et al., 1994).

As shown in the Examples below, nerve cells express molecules which are requisite for T cell activation, indicating that there is a neuro-immunological intercellular interactive component that occurs during neuronal differentiation. NGF and EGF have profound effects on the differentiation process in utero and early life and on the regeneration process after pathologic damage. The data provided in the examples is relevant since it not only demonstrates the existence of inducible surface molecules on post-mitotic neurons, but their ability to be kinetically modified by the presence or absence of specific trophic factors is also highlighted. The presence of Fas on the neuronal cell surface suggests that PC12 cells and their variants are vulnerable to apoptosis or that the molecule is capable of transmitting a mitotic signal if required.

Another aspect of the invention involves a method for inducing apoptosis in a nerve cell. The method involves the step of contacting a nerve cell with an amount of a metabolic modifying agent which when exposed to a nerve cell causes coupling of electron transport and oxidative phosphorylation effective to increase the mitochondrial membrane potential in the nerve cell and contacting a neural activating cell with an amount of a B7 receptor blocking agent effective for inducing apoptosis in the nerve cell. "Metabolic modifying agents" and "Fas binding agents" are discussed above.

A "B7 receptor blocking agent" as used herein is any agent which interacts with a B7 receptor but does not cause activation of the cell and prevents that receptor from binding to B7. These agents include, for example, but are not limited to anti-CD28 antibodies, CD28 binding peptides, anti-CTLA-4 antibodies, CTLA-4 analogs and CTLA-4 binding peptides which do not cause activation of the receptor. Other B7 receptor blocking agents can be identified by those of skill in the art by routine experimentation using immune cell activation assays such as a T cell activation assay.

This method is useful whenever it is desirable to induce apoptosis of a nerve cell. For instance, it may be useful to induce apoptosis of a nerve cell in vitro in order to screen molecules for their ability to prevent apoptosis of nerve cells. Other uses will be apparent to those of ordinary skill in the art.

As discussed above, when a cell is coupled, Fas is expressed on the cell surface and when a cell is uncoupled Fas generally is transported to intracellular stores. When a cell is coupled and Fas is on the surface engagement of Fas sends a signal to the cell instructing the cell to undergo cellular division. When a cell is uncoupled ordinarily Fas is not expressed on the cell surface. In the presence of NGF, however, Fas is down regulated and is no longer expressed on the cell surface. In a damaged tissue if a nerve cell is in an uncoupled state, and expresses both Fas and B7 on the surface, then the presence or absence of NGF will determine the fate of the cell. If an NGF producing cell according to the invention is present in the local environment, the B7 of the nerve cell will stimulate production of NGF by interacting with that cell. The local NGF produced will cause the down regulation of Fas and the cell will undergo differentiation. If an NGF producing cell is not available or if B7 is not expressed on the surface of the nerve cell, then environmental factors can stimulate Fas to cause apoptosis.

Another aspect of the invention is a method for reinnervating an injured tissue. The method involves the step of implanting a B7 expressing nerve cell in the injured tissue, wherein the implanted B7 expressing nerve cell will undergo neuronal differentiation in the presence of a neural activating cell in the injured tissue to reinnervate the injured tissue. Methods are known in the art implanting nerve cells into living tissue. For example, nerves can be implanted directly into exposed tissue or may be implanted in biodegradable tubes which will guide the extension of the nerve into surrounding tissue where it can be differentiated.

A B7 expressing nerve cell can be prepared by an means known in the art. For instance, a B7 expressing nerve cell may be genetically engineered to constitutively or inducibly express B7. The gene encoding a B7 protein can be constitutively expressed in a nerve cell by transfection procedures known in the art, such as by the methods described above. B71 gene is provided herein as SEQ ID No. 1 and listed under Accession No. M27533 in Genebank and the nucleic acid sequence for B72 is provided herein as SEQ ID No. 2 and listed under Accession No. U04343 in Genebank. Alternatively the nerve cell may be engineered to inducibly or constitutively express UCP which will induce expression of endogenous B7. In another embodiment, the implanted B7 expressing nerve cell may also constitutively or inducibly express at least one of the nerve growth factor receptors, which would induce expression of endogenous B7.

An injured tissue is a tissue in which nerve damage has been sustained. An injured tissue may include for example, a spinal chord injury, a severed or severely damaged limb or any other tissue which can be innervated and in which the nerve has been damaged. Neural activating cells are generally found in skin and muscle surrounding the nerves of an injured tissue. These neural activating cells can stimulate the differentiation of the nerve cell once they are activated by interaction with the B7 on the surface of the nerve cell.

The invention also includes a method for treating a neurodegenerative disorder by administering an amount of a B7 inducing agent effective to induce the expression of B7 on the surface of a nerve cell. An amount that is effective to induce the expression on the surface is an amount which is effective to cause dissipation of a proton motor force and thus to decrease the mitochondrial membrane potential in the nerve cell.

A "neurodegenerative disorder" as used herein, is a disorder associated with the death or injury of neuronal cells. For example, the loss of dopaminergic neurons in the substantia nigra ultimately leads to Parkinson's Disease. The deposition of β-amyloid protein in the brain generally causes neural damage leading to Alzheimer's Disease. Conditions involving injuries such as brain ischemia, spinal chord damage, and severance of limbs often causes extensive neuronal cell death. When a nerve is severed, the regions of the nerve cells which are distal to the severance become separated from the nerve cell body and degenerate. After such a severance, it is possible for the nerve cell body to regenerate by re-extension of the severed axons. This process of nerve regeneration does not occur naturally in the absence of certain environmental conditions. In some cases in the prior art, various factors such as nerve growth factor have been added to the nerve to attempt to stimulate the regeneration. The methods of the invention describe a different system in which the nerve cell is manipulated to express an immune recognition molecule on its surface which can then cause the local expression of nerve growth factor leading to differentiation. This method more closely simulates the natural processes of neuronal regeneration. Other neurodegenerative diseases include for example but are not limited to epileptic seizures and amyotrophic lateral sclerosis.

The invention also includes compositions of the above described agents. One composition of the invention includes a metabolic modifying agent and an apoptotic chemotherapeutic agent. The pharmaceutical preparations of the invention are administered to subjects in effective amounts. An effective amount means that amount necessary to delay the onset of, inhibit the progression of, halt altogether the onset or progression of or diagnose the particular condition being treated. In one embodiment the metabolic modifying agent and the apoptotic chemotherapeutic agent are present in an effective dose for treating a tumor. In another embodiment the metabolic modifying agent and the apoptotic chemotherapeutic agent are present in an effective dose for treating type II diabetes. In general, an effective amount for treating cancer and type I diabetes will be that amount necessary to favorably affect mammalian cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Another composition according to the invention is an MHC class II HLA-DR inducing agent and an MHC class II HLA-DR ligand. In one embodiment the MHC class II HLA-DR inducing agent and MHC class II HLA-DR ligand are present in an effective dose for treating type II diabetes. In general, an effective amount for treating type II diabetes will be that amount necessary to favorably affect mammalian cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

One composition of the invention is a B7 inducing agent and a B7 receptor inducing agent. In one embodiment the B7 inducing agent and B7 receptor inducing agent present in an effective dose for treating neurodegenerative disease. In general, an effective amount for neurodegenerative disease will be that amount necessary to favorably affect nerve cell differentiation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Generally, doses of active compounds will be from about 0.01 mg/kg per day to 1000 mg/kg per day. It is expected that doses range of 50-500 mg/kg will be suitable, in one or several administrations per day. In the event that a response in a subject is insufficient at the initial doses applied, higher doses (or effectively higher doses by a different, more localized delivery route) may be employed to the extent that patient tolerance permits. Multiple doses per day are contemplated to achieve appropriate levels of compounds.

The invention involves the use of several different types of binding peptides or molecules, MHC class II HLA-DR binding peptides, CD4/αβTCR binding molecules, CD40 binding peptides, MHC class II HLA-DP/DQ binding peptides, CD28/CTLA4 binding peptides, and Fas biding peptides. The binding peptides of the invention can be identified using routine assays, such as the binding and activation assays described in the Examples and elsewhere throughout this patent application.

The binding peptides of the invention are isolated peptides. As used herein, with respect to peptides, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

The binding peptides also may easily be synthesized or produced by recombinant means by those of skill in the art. Methods for preparing or identifying peptides which bind to a particular target are well known in the art. Molecular imprinting, for instance, may be used for the de novo construction of macromolecular structures such as peptides which bind to a particular molecule. See for example Kenneth J. Shea, Molecular Imprinting of Synthetic Network Polymers: The De Novo synthesis of Macromolecular Binding and Catalytic Sites, *TRIP* Vol. 2, No. 5, May 1994; Klaus Mosbach, Molecular Imprinting, *Trends in Biochem. Sci.,* 19(9) January 1994; and Wulff, G., in Polymeric Reagents and Catalysts (Ford, W. T., Ed.) *ACS Symposium* Series No. 308, pp 186-230, *American Chemical Society* (1986). One method for preparing mimics of the known binding peptides involves the steps of: (i) polymerization of functional monomers around a known binding peptide or the binding region of an antibody which also binds to the targets (the template) that exhibits a desired activity; (ii) removal of the template molecule; and then (iii) polymerization of a second class of monomers in the void left by the template, to provide a new molecule which exhibits one or more desired properties which are similar to that of the template. In addition to preparing peptides in this manner other binding molecules which have the same function as the binding peptides useful according to the invention such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are typically prepared by the free radical polymerization of functional monomers, resulting in a compound with a non-biodegradable backbone. Other methods for designing such molecules include for example drug design based on structure activity relationships which require the synthesis and evaluation of a number of compounds and molecular modeling.

The binding peptides may also be identified by conventional screening methods such as phage display procedures (e.g., methods described in Hart, et al., *J. Biol. Chem.* 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands having the appropriate binding properties are obtained by selecting those phages which express on their surface a ligand that binds to the target molecule. These phages then are subjected to several cycles of reselection to identify the peptide ligand-expressing phages that have the most useful binding characteristics. Typically, phages that exhibit the best binding characteristics (e.g., highest affinity) are further characterized by nucleic acid analysis to identify the particular amino acid sequences of the peptides expressed on the phage surface and the optimum length of the expressed peptide to achieve optimum binding. Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

To determine whether a peptide binds to the appropriate target any known binding assay may be employed. For example, in the case of a peptide that binds to the MHC class II HLA-DR the peptide may be immobilized on a surface and then contacted with a labeled MHC class II HLA-DR (or vice versa). The amount of MHC class II HLA-DR which interacts with the peptide or the amount which does not bind to the peptide may then be quantitated to determine whether the peptide binds to MHC class II HLA-DR. A surface having a known peptide that binds to MHC class II HLA-DR such as a commercially available monoclonal antibody immobilized thereto may serve as a positive control.

Screening of peptides of the invention, also can be carried out utilizing a competition assay. If the peptide being tested competes with the known monoclonal antibody, as shown by a decrease in binding of the known monoclonal antibody, then it is likely that the peptide and the known monoclonal antibody bind to the same, or a closely related, epitope. Still another way to determine whether a peptide has the specificity of the known monoclonal antibody is to pre-incubate the known monoclonal antibody with the target with which it is normally reactive, and then add the peptide being tested to determine if the peptide being tested is inhibited in its ability to bind the target. If the peptide being tested is inhibited then, in all likelihood, it has the same, or a functionally equivalent, epitope and specificity as the known monoclonal antibody.

By using the known MHC class II HLA-DR (and other target) monoclonal antibodies of the invention, it is also possible to produce anti-idiotypic antibodies which can be used to screen other antibodies to identify whether the antibody has the same binding specificity as the known monoclonal antibody. Such anti-idiotypic antibodies can be produced using well-known hybridoma techniques (Kohler and Milstein, *Nature,* 256:495, 1975). An anti-idiotypic antibody is an antibody which recognizes unique determinants present on the known monoclonal antibodies. These determinants are located in the hypervariable region of the antibody. It is this region which binds to a given epitope and, thus, is responsible for the specificity of the antibody. An anti-idiotypic antibody can be prepared by immunizing an animal with the known monoclonal antibodies. The immunized animal will recognize and respond to the idiotypic determinants of the immunizing known monoclonal antibodies and produce an antibody to these idiotypic determinants. By using the anti-idiotypic antibodies of the immunized animal, which are specific for the known monoclonal antibodies of the invention, it is possible to identify other clones with the same idiotype as the known monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody.

In one embodiment the binding peptides useful according to the invention are antibodies or functionally active antibody fragments. Antibodies are well known to those of ordinary skill in the science of immunology. Many of the binding peptides described herein are available from commercial sources as intact functional antibodies. As used herein, the term "antibody" means not only intact antibody molecules but also fragments of antibody molecules retaining specific binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316-325 (1983)).

As is well-known in the art, the complementarity determining regions (CDRs) of an antibody are the portions of the antibody which are largely responsible for antibody specificity. The CDR's directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1 through CDR3). The framework regions (FRs) maintain the tertiary structure of the paratope, which is the portion of the antibody which is involved in the interaction with the antigen. The CDRs, and in particular the CDR3 regions, and more particularly the heavy chain CDR3 contribute to antibody specificity. Because these CDR regions and in particular the CDR3 region confer antigen specificity on the antibody these regions may be incorporated into other antibodies or peptides to confer the identical specificity onto that antibody or peptide.

According to one embodiment, the peptide of the invention is an intact soluble monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. As used herein the term "monoclonal antibody" refers to a homogenous population of immunoglobulins which specifically bind to an epitope (i.e. antigenic determinant), e.g., of MHC class II HLA-DR.

The peptide useful according to the methods of the present invention may be an intact humanized a monoclonal antibody. A "humanized monoclonal antibody" as used herein is a human monoclonal antibody or functionally active fragment thereof having human constant regions and a binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.). For instance, a humanized form of the Pharmingen anti-Fas antibody used in the attached Examples could be easily prepared and used according to the methods of the invention.

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, New York, 1987), and Boerner et al., *J. Immunol.*, 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA,* 90: 2551 (1993), Jakobovits et al., Nature, 362: 255-258 (1993), Bruggermann et al., *Year in Immuno.,* 7:33 (1993) and U.S. Pat. No. 5,569,825 issued to Lonberg).

The binding peptides may also be functionally active antibody fragments. Significantly, is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are used consistently with their standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

The B7 and UCP expression vectors and other relevant expression vectors described herein can be prepared and inserted into cells using routine procedures known in the art. These procedures are set forth below in more detail. The term "IRM" (immune recognition molecule) nucleic acid is used herein to refer to each of the nucleic acids encompassed by the expression vectors described herein. Although UCP is not an immune molecule the term IRM is used to encompass UCP nucleic acids to simplify the discussion. "IRM nucleic acid", as used herein, refers to a nucleic acid molecule which: (1) hybridizes under stringent conditions to a nucleic acid having the sequence of SEQ ID NO:1, 3, 5, 7, 9, and 11 and (2) codes for a IRM polypeptide (i.e., the respective immune recognition polypeptide). The preferred IRM nucleic acid has the nucleic acid sequence of SEQ ID NO:1, 3, 5, 7, 9, and 11 (the nucleic acids encoding the human B7.1, B7.2, UCP-1, UCP-2, UCP-3S, and CD28 polypeptides respectively). The IRM nucleic acids may be intact IRM nucleic acids which include the nucleic acid sequence of Sequence ID No. 1-5 as well as homologs and alleles of a nucleic acid having the sequence of SEQ ID NO:1, 3, 5, 7, 9, and 11. Intact IRM nucleic acids further embrace nucleic acid molecules which differ from the sequence of SEQ ID NO:1, 3, 5, 7, 9, and 11 in codon sequence due to the degeneracy of the genetic code. The IRM nucleic acids of the invention may also be functionally equivalent variants, analogs and fragments of the foregoing nucleic acids. "Functionally equivalent", in reference to a IRM nucleic acid variant, analog or fragment, refers to a nucleic acid that codes for a IRM polypeptide that is capable of functioning as an immune recognition molecule or an uncoupling protein. The invention further embraces complements of the foregoing nucleic acids or of unique fragments of the foregoing nucleic acids. Such complements can be used, for example, as antisense nucleic acids for inhibiting the expression of IRM in a cell in order to create an experimental model of a cell in which IRM is not expressed.

The IRM nucleic acid molecules can be identified by conventional techniques, e.g., by identifying nucleic acid sequences which code for IRM polypeptides and which hybridize to a nucleic acid molecule having the sequence of SEQ ID NO:1, 3, 5, 7, 9, and 11 under stringent conditions. The term "stringent conditions", as used herein, refers to parameters with which the art is familiar. More specifically, stringent conditions, as used herein, refer to hybridization at 65° C. in hybridization buffer (3.5×SSC, 0.02% Ficoll, 0.02% polyvinyl pyrolidone, 0.02% bovine serum albumin, 2.5 mM NaH$_2$PO$_4$ (pH 7), 0.5% SDS, 2 mM EDTA). SSC is 0.15M sodium chloride/0.15M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the IRM nucleic acid of the invention. The skilled artisan also is familiar with the methodology for screening cells and libraries for the expression of molecules, such as IRM, which can be isolated, followed by purification and sequencing of the pertinent nucleic acid molecule. In screening for IRM nucleic acid sequences, a Southern blot may be performed using the foregoing conditions, together with a radioactive probe. After washing the membrane to which the DNA is finally transferred, the membrane can be placed against x-ray film to detect the radioactive signal.

In general, homologs and alleles typically will share at least 40% nucleotide identity with SEQ ID NO:1, 3, 5, 7, 9, and 11; in some instances, will share at least 50% nucleotide identity; and in still other instances, will share at least 60% nucleotide identity. The preferred homologs have at least 70% sequence homology to SEQ ID NO:1, 3, 5, 7, 9, and 11. More preferably the preferred homologs have at least 80% and, most preferably, at least 90% sequence homology to SEQ ID NO:1, 3, 5, 7, 9, and 11-5.

The invention also includes degenerate nucleic acids which include alternative codons to those present in the naturally occurring nucleic acid that codes for the human IRM polypeptide. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the naturally occurring nucleic acids in codon sequence due to the degeneracy of the genetic code.

The IRM nucleic acid, in one embodiment, is operably linked to a gene expression sequence which directs the expression of the IRM nucleic acid within a eukaryotic cell. The "gene expression sequence" is any regulatory nucleotide sequence, such as a promoter sequence or promoter-enhancer combination, which facilitates the efficient transcription and translation of the IRM nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, and β-actin. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined IRM nucleic acid. The gene expression sequences optionally include enhancer sequences or upstream activator sequences as desired.

Preferably, the IRM nucleic acid of the invention is linked to a gene expression sequence which permits expression of the IRM nucleic acid in the local environment of a cell, e.g. a damaged nerve cell. In some embodiments the gene expression sequence permits expression of the IRM nucleic acid in a human nerve cell or a neural activating cell. A sequence which permits expression of the IRM nucleic acid in a nerve cell or a neural activating cell is one which is selectively active in nerve cell or a neural activating cell and thereby causes the expression of the IRM nucleic acid in these cells. Those of ordinary skill in the art will be able to easily identify promoters that are capable of expressing a IRM nucleic acid in a nerve cell or a neural activating cell, as well as other known cells.

The IRM nucleic acid sequence and the gene expression sequence are said to be "operably linked" when they are covalently linked in such a way as to place the transcription and/or translation of the IRM coding sequence under the influence or control of the gene expression sequence. If it is desired that the IRM sequence be translated into a functional protein, two DNA sequences are said to be operably linked if induction of a promoter in the 5' gene expression sequence results in the transcription of the IRM sequence and if the nature of the linkage between the two DNA sequences does not (1) result in the introduction of a frame-shift mutation, (2) interfere with the ability of the promoter region to direct the transcription of the IRM sequence, or (3) interfere with the ability of the corresponding RNA transcript to be translated into a protein. Thus, a gene expression sequence would be operably linked to a IRM nucleic acid sequence if the gene expression sequence were capable of effecting transcription of that IRM nucleic acid sequence such that the resulting transcript might be translated into the desired protein or polypeptide.

The IRM nucleic acid of the invention can be delivered to the cell alone or in association with a vector. In its broadest sense, a "vector" is any vehicle capable of facilitating: (1) delivery of a IRM molecule to a target cell or (2) uptake of a IRM molecule by a target cell. Preferably, the vectors transport the IRM molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing a IRM nucleic acid) can be selectively delivered to a cell in, e.g., an injured nerve tissue. In general, the vectors useful in the invention are divided into two classes: biological vectors and chemical/physical vectors. Biological vectors are useful for delivery/uptake of IRM nucleic acids to/by a target cell. Chemical/physical vectors are also useful for delivery/uptake of IRM nucleic acids to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be attached to the nucleic acid sequences of the invention. Viral vectors are a preferred type of biological vector and include, but are not limited to, nucleic acid sequences from the following viruses: retroviruses, such as: Moloney murine leukemia virus; Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Cliffton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In addition to the biological vectors, chemical/physical vectors may be used to deliver a IRM molecule to a target cell and facilitate uptake thereby. As used herein, a "chemical/physical vector" refers to a natural or synthetic molecule, other than those derived from bacteriological or viral sources, capable of delivering the IRM molecule to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 μm can encapsulate large macromolecules. RNA, DNA, and intact virions can be encapsulated within the aqueous interior and be delivered to cells in a biologically active form (Fraley, et al., *Trends Biochem. Sci.*, (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, such as the site of a tumor, by coupling the liposome to a specific ligand such as a monoclonal antibody, sugar, glycolipid, or protein. Ligands which may be useful for targeting a liposome to a tumor cell include, but are not limited to: intact or fragments of IRM which interact with tumor cell specific receptor and molecules which interact with the cell surface markers of tumor cells such as antibodies. Such ligands may easily be identified by binding assays well known to those of skill in the art. Additionally, the vector may be coupled to a nuclear targeting peptide, which will direct the IRM nucleic acid to the nucleus of the host cell.

Liposomes are commercially available from Gibco BRL, for example, as LIPOFECTIN™ and LIPOFECTACE™, which are formed of cationic lipids such as N-[1-(2,3dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, (1985) 3:235-241.

In one particular embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 08/213,668, filed Mar. 15, 1994). PCT/US/0307 describes a biocompatible, preferably biodegradable polymeric matrix for containing an exogenous gene under the control of an appropriate promotor. The polymeric matrix is used to achieve sustained release of the exogenous gene in the patient. In accordance with the instant invention, the IRM nucleic acids described herein are encapsulated or dispersed within the biocompatible, preferably biodegradable polymeric matrix disclosed in PCT/US/03307.

The polymeric matrix preferably is in the form of a microparticle such as a microsphere (wherein the IRM molecule is dispersed throughout a solid polymeric matrix) or a microcapsule (wherein the IRM molecule is stored in the core of a polymeric shell). Other forms of the polymeric matrix for containing the IRM molecule include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and IRM molecule are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time.

In another embodiment the chemical/physical vector is a biocompatible microsphere that is suitable for oral delivery. Such microspheres are disclosed in Chickering et al., *Biotech. And Bioeng.*, (1996) 52:96-101 and Mathiowitz et al., *Nature*, (1997) 386:410-414.

Both non-biodegradable and biodegradable polymeric matrices can be used to deliver the IRM nucleic acids of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the IRM nucleic acids are delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in *Macromolecules*, (1993) 26:581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Compaction agents also can be used alone, or in combination with, a biological or chemical/physical vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the IRM molecule in a form that is more efficiently taken up by the cell or, more preferably, in combination with one or more of the above-described vectors.

Other exemplary compositions that can be used to facilitate uptake by a target cell of the IRM nucleic acids include calcium phosphate and other chemical mediators of intracellular transport, microinjection compositions, electroporation and homologous recombination compositions (e.g., for integrating a IRM nucleic acid into a preselected location within the target cell chromosome).

In addition to the expression vectors, the invention also encompasses the use of antisense oligonucleotides that selectively bind to a IRM nucleic acid molecule, and dominant negative IRM to reduce the expression of IRM. Antisense oligonucleotides are useful, for example, for preparing an animal model of a subject having a neurodegenerative disorder. Such animal models can be used in screening assays for identifying therapeutic drugs for treating neurodegenerative disorders.

As used herein, the term "antisense oligonucleotide" or "antisense" describes an oligonucleotide which hybridizes under physiological conditions to DNA comprising a particular gene or to an RNA transcript of that gene and, thereby, inhibits the transcription of that gene and/or the translation of the mRNA. The antisense molecules are designed so as to hybridize with the target gene or target gene product and thereby, interfere with transcription or translation of the target mammalian cell gene. Those skilled in the art will recognize that the exact length of the antisense oligonucleotide and its degree of complementarity with its target will depend upon the specific target selected, including the sequence of the target and the particular bases which comprise that sequence. The antisense must be a unique fragment. A unique fragment is one that is a 'signature' for the larger nucleic acid. It, for example, is long enough to assure that its precise sequence is not found in molecules outside of the IRM gene. As will be recognized by those skilled in the art, the size of the unique fragment will depend upon its conservancy in the genetic code. Thus, some regions of SEQ ID NO:1, 3, 5, 7, 9, and 11, will require longer segments to be unique while others will require only short segments, typically between 12 and 32 base pairs (e.g. 12, 13, 14, 15, 16, 17, 18, 19, 20, 21, 22, 23, 24, 25, 26, 27, 28, 29, 30, 31 and 32 bases long).

It is preferred that the antisense oligonucleotide be constructed and arranged so as to bind selectively with the target under physiological conditions, i.e., to hybridize substantially more to the target sequence than to any other sequence in the target cell under physiological conditions. Based upon the known sequence of a gene that is targeted for inhibition by antisense hybridization, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 7 and, more preferably, at least 15 consecutive bases which are complementary to the target. Most preferably, the antisense oligonucleotides comprise a complementary sequence of 20-30 bases. Although oligonucleotides may be chosen which are antisense to any region of the gene or RNA (e.g., mRNA) transcripts, in preferred embodiments the antisense oligonucleotides are complementary to 5' sites, such as translation initiation, transcription initiation or promoter sites, that are upstream of the gene that is targeted for inhibition by the antisense oligonucleotides. In addition, 3'-untranslated regions may be targeted. Furthermore, 5' or 3' enhancers may be targeted. Targeting to mRNA splice sites has also been used in the art but may be less preferred if alternative mRNA splicing occurs. In at least some embodiments, the antisense is targeted, preferably, to sites in which mRNA secondary structure is not expected (see, e.g., Sainio et al., *Cell Mol. Neurobiol.*, (1994) 14(5):439-457) and at which proteins are not expected to bind. The selective binding of the antisense oligonucleotide to a mammalian target cell nucleic acid effectively decreases or eliminates the transcription or translation of the mammalian target cell nucleic acid molecule. Reduction in transcription or translation of the nucleic acid molecule is desirable in preparing an animal model for further defining the role played by the mammalian target cell nucleic acid in modulating an adverse medical condition.

The invention also includes the use of a "dominant negative UCP" polypeptide. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide as used herein in a cell is a reduction in function of active UCP. One of ordinary skill in the art can assess the potential for a dominant negative variant of a protein, and using standard mutagenesis techniques to create one or more dominant negative variant polypeptides. For example, one of ordinary skill in the art can modify the sequence of the UCP by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

In other aspects the invention includes transgenic animals and cells transfected with the IRM's. Additionally, complements of the IRM nucleic acids described above can be useful as anti-sense oligonucleotides, e.g., by delivering the anti-sense oligonucleotide to an animal to 110 induce a "knockout" phenotype. The administration of anti-sense RNA probes to block gene expression is discussed in Lichtenstein, C., *Nature* 333:801-802 (1988).

Alternatively, the IRM nucleic acids can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of IRM knockout and transgenic animals as models for the study of neurodegenerative disorders.

A variety of methods are available for the production of transgenic animals associated with this invention. DNA can be injected into the pronucieus of a fertilized egg before fusion of the male and female pronuclei, or injected into the nucleus of an embryonic cell (e.g., the nucleus of a two-cell embryo) following the initiation of cell division. See e.g., Brinster et al., *Proc. Nat. Acad. Sci. USA*, 82: 4438 (1985); Brinster et al., cell 27: 223 (1981); Costantini et al., *Nature* 294: 982 (1981); Harpers et al., *Nature* 293: 540 (1981); Wagner et al., *Proc. Nat. Acad. Sci. USA* 78:5016 (1981); Gordon et al., *Proc. Nat. Acad. Sci. USA* 73: 1260 (1976). The fertilized egg is then implanted into the uterus of the recipient female and allowed to develop into an animal.

An alternative method for producing transgenic animals involves the incorporation of the desired gene sequence into a virus which is capable of affecting the cells of a host animal. See e.g., Elbrecht et al., Molec. Cell. Biol. 7: 1276 (1987); Lacey et al., Nature 322: 609 (1986); Leopol et al., Cell 51: 885 (1987). Embryos can be infected with viruses, especially retroviruses, modified to carry the nucleotide sequences which encode IRM proteins or sequences which disrupt the native IRM gene to produce a knockout animal.

Another method for producing transgenic animals involves the injection of pluripotent embryonic stem cells into a blastocyst of a developing embryo. Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. See e.g., Robertson et al., Cold Spring Harbor Conference Cell Proliferation 10: 647 (1983); Bradley et al., Nature 309: 255 (1984); Wagner et al., Cold Spring Harbor Symposium Quantitative Biology 50: 691 (1985).

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47: 897-905 (1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell*, 63:1099-1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science*, 244: 1288-1292 (1989). Methods for positive selection of the recombination event (e.g., neo resistance) and dual positive-negative selection (e.g., neo resistance and gancyclovir resistance) and the subsequent identification of the desired clones by PCR have been described by Capecchi, supra and Joyner et al., *Nature*, 338: 153-156 (1989). The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

Procedures for the production of non-rodent mammals and other animals have been discussed by others. See Houdebine and Chourrout, supra; Pursel et al., *Science* 244: 1281-1288 (1989); and Simms et al., *Bio/Technology*, 6: 179-183 (1988).

Inactivation or replacement of the endogenous IRM genes can be achieved by a homologous recombination system using embryonic stem cells. The resultant transgenic non-human mammals having a knockout characteristic may be used as a model for neurodegenerative disorders. Nerve cells which do not express IRMs may be predisposed to apoptosis and unable to differentiate and thus, produce a neurodegenerative phenotype. A variety of therapeutic drugs can be administered to the phenotypically neurodegenerative animals to determine the affect of the therapeutic drugs on nerve cell differentiation. In this manner, therapeutic drugs which are useful for preventing or reducing neurodegenerative disorders can be identified. Such agents are useful for, e.g., treating spinal chord injuries or Parkinson's disease.

Additionally, a normal or mutant version of IRM can be inserted into the mouse germ line to produce transgenic animals which constitutively or inducible express the normal or mutant form of IRM. These animals are useful in studies to define the role and function of IRM in cells.

The metabolic modifying agent, apoptotic chemotherapeutic agent, MHC class II HLA-DR inducing agent, MHC class II HLA-DR ligand, B7 receptor blocking agent, B7 inducing agent, and B7 receptor inducing agent described herein are commercially available compounds, are derived from commercially available compounds or are synthesized de novo using routine chemical synthetic procedures known to those of ordinary skill in the art.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. As used herein, a composition of an metabolic modifying agent and an apoptotic chemotherapeutic agent means the compounds described above as well as salts thereof and a composition of an MHC class II HLA-DR inducing agent and an MHC class II HLA-DR ligand means the compounds described above as well as salts thereof.

The compositions of the invention may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the compositions of the invention, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the compositions of the invention into association with a carrier which constitutes one or more accessory ingredients. In general, the compositions are prepared by uniformly and intimately bringing the compositions of the invention into association with a liquid carrier, a finely divided solid carrier, or both, and then, if necessary, shaping the product.

Compositions suitable for oral administration may be presented as discrete units, such as capsules, tablets, lozenges, each containing a predetermined amount of the compositions of the invention. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S.

Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the compositions of the invention is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The following examples are provided to illustrate specific instances of the practice of the present invention and are not to be construed as limiting the present invention to these examples. As will be apparent to one of ordinary skill in the art, the present invention will find application in a variety of compositions and methods.

EXAMPLES

Example 1

Metabolic State of a Cell is Indicative of Cell Surface Fas Expression and Sensitivity/Resistance to Cell Death 1. Resistance to apoptosis is characterized by failure to express Fas: The cell lines utilized herein include L1210, a leukemic cell line; HL60, a human pro-myelocytic cell line; and PC12, a pheochromocytoma cell line which can be induced to differentiate into a neuronal cell line in the presence of NGF (Lindenboim, L, et al., *Cancer Res,* 1995, 55:1242-7). Each cell line was examined in parallel with apoptotic resistant sublines: L1210 DDP, HL60 MDR, and PC12Trk. L1210 DDP are resistant to cisplatin and methotrexate; HL60 MDR are resistant to adriamycin induced apoptosis; PC12 TrkA, which have been transfected with TrkA which results in constitutively expression the NGF receptors, are not susceptible to alcohol and NGF withdrawal as are the PC12 cells.

The apoptosis sensitive cells from each tissue origin were morphologically round, non-adherent, rapidly dividing cells, with the exception of the PC12 cell line. The apoptosis resistant cells from all tissue origins were morphologically large, adherent, and slowly dividing cells.

The recently characterized molecules, Fas (CD95) and Fas Ligand (CD95L), have been strongly implicated in the process of apoptotic death (Muller, M, et al., *J Clin Invest,* 1997, 99:403-413). We examined expression of Fas on the above-identified cell lines. Independent of tissue origin, all of the apoptosis resistant lines fail to express cell surface Fas both constitutively and in the presence of agents that induce apoptosis in the parental cell lines, as shown in FIG. 1A.

FIG. 1A shows a flow cytometric analysis of Fas expression. Isotype control (thick line) versus FITC-anti-Fas (Pharmingen) (thin lines), on (from top to bottom) L1210; PC12; and HL60 cells, left panels as indicated. Panels on the right are staining of resistant cell lines L1210DDP, PC12Trk; and HL60MDR. The histograms representing isotype control (thick) versus FITC-anti-Fas (thin lines) are completely overlapping on the right panels, indicating an absence of Fas expression. A Coulter Epics Elite flow cytometer with a single excitation wavelength (488 nm) and band filters for PE (575 nm), FITC (525 nm) and Red613 (613 nm) was used to analyze the stained cells. Each sample population was classified for cell size (forward scatter) and complexity (side scatter), gated on a population of interest and evaluated using 40,000 cells. Criteria for positive staining were established by comparison with the intensity of the isotype controls, thick lines.

Figure 1B:
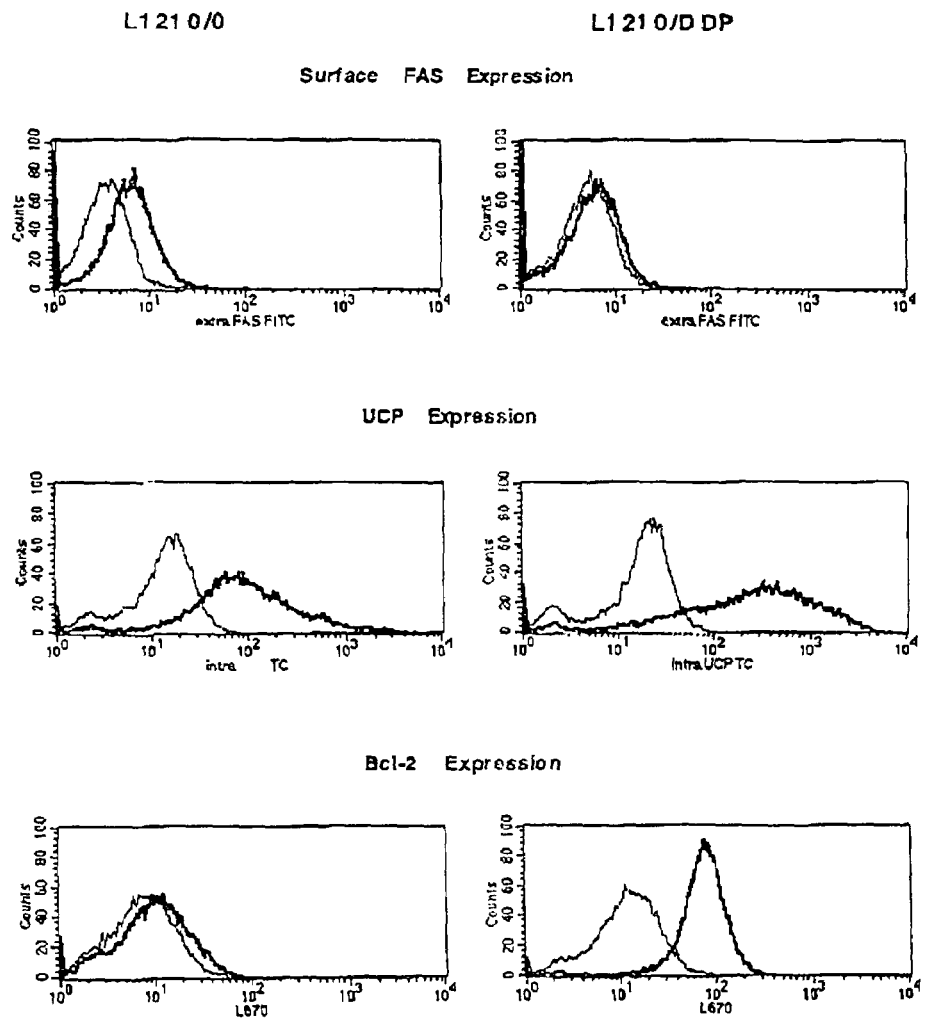

FIG. 1B is a flow cytometric analysis of extracellular Fas and intracellular UCP and bcl-2 expression. Isotype control (Thick line) versus FITC-anti-Fas (Pharmingen) (Thin lines), on L1210, left panels, and L1210DDP, right panels. The histograms represent Isotype control (thin) versus FITC-anti-Fas (thick lines). A coulter Epics Elite flow cytometer with a single excitation wavelength (488 nm) and band filters for PE (575 nm), FITC (525 nm) and Red613 (613 nm) was used to analyze the stained cells. Each sample population was classified for cell size (forward scatter) and complexity (side scatter), gated on a population of interest and evaluated using 40,000 cells. Criteria for positive staining were established by comparison with Isotype controls, thin lines to specific stain, thick lines.

2. Resistance to apoptosis is characterized by relatively high rates of glucose oxidation and utilization: We performed experiments to examine the correlation between cell surface Fas expression and glucose metabolism. As a prototype for the Fas positive and Fas negative cells we used the L1210 and the L1210DDP cell lines, as Fas positive and Fas negative, respectively. We directly measured the rates of glucose utilization and oxidation of L1210 and L1210DDP. Ratios were generated by using nanomolar values.

Rate of glucose utilization was measured by the method of Ashcroft et al. Briefly, cells were incubated 90 min at 37° C. in 100 µl KRB, glucose (5.5 mM), 1.3 µCi D-[5-$^3$H] glucose (Amersham, Arlington Heights, Ill.). The reaction was carried out in a 1 ml cup contained in a rubber stoppered 20 ml scintillation vial that had 500 µl of distilled water surrounding the cup. Glucose metabolism was stopped by injecting 100 µl 1 M Hcl through the stopper into the cup. An overnight incubation at 37° C. was carried out to allow equilibration of the [$^3$H]-$H_2O$ in the reaction cup and the distilled water, followed by liquid scintillation counting of the distilled water.

Rate of glucose oxidation was measured by incubating cells for 90 min at 37° C. in 100 ml of reaction buffer, glucose (2.8, 8.3, 27.7 mmol/l), 1.7 mCi (U-14C glucose). The reaction was carried out in a 1 ml cup in a 20 ml scintillation vial capped by a rubber stopper with a center well that contains filter paper. Metabolism was stopped and $CO_2$ liberated with 300 ml 1 mol/l HCl injected through the stopper into the cup containing the cells. $CO_2$ was trapped in the filter paper by injecting 10 ml 1 mol/l KOH into the center well, followed 2 hours later by liquid scintillation counting. Tubes containing $NaHCO_3$ and no cells were used to estimate the recovery of $^{14}CO_2$ in the filter paper, routinely close to 100%.

The results are presented in Table 1.

TABLE 1

Glucose Metabolism in L1210/0 and L1210/DDP

|  | L1210/0 | L1210/DDP |
|---|---|---|
| Glucose Utilization (pmol glucose/90 min/50,000 cells) | 1740 ± 920 | 3470 ± 460 |
| Glucose Oxidation (pmol glucose/90 min/50,000 cells) | 235 ± 7 | 428 ± 124 |
| Glucose Utilization/Oxidation | 7.4 | 8.1 |

Because the L1210 and L1210DDP cells are tumor cell lines and are likely to have increased ratios of glucose oxidation to utilization (Warburg, O, et al., *Klin Woch*, 1926, 5:829-832), we measured glucose utilization on normal lymphocytes. We isolated $10^6$ splenic lymphocytes from C57BL16 animals, Fas-deficient C57BL/6 (B6.lpr), and FasL defective C57BL/6 (B6.gld) animals. The rate of glucose utilization and oxidation of the Fas deficient and the FasL deficient lymphocytes are demonstrated in Table 2. The ratio of glucose utilization to oxidation is highest in lpr lymphocytes and lowest in wild type normal, quiescent lymphocytes.

TABLE 2

Glucose Metabolism in Lymphocytes from Normal, Fas Deficient and FasL Deficient Mice

|  | b6 | lpr | gld |
|---|---|---|---|
| GLUCOSE UTILIZATION (nmol glucose/90 mins/50,000 cells) | 0.04 | 0.36 | 0.22 |
| GLUCOSE OXIDATION (pmol glucose/90 mins/50,000 cells) | 73.24 | 164.51 | 122.82 |

|  | CELL TYPE | RATIO |
|---|---|---|
| GLUCOSE UTILIZATION/ GLUCOSE OXIDATION | b6 | 0.55 |
|  | lpr | 2.19 |
|  | gld | 1.79 |

These data (Table 1 & 2) demonstrate high rates of glucose utilization and oxidation of both tumor lines relative to the normal lymphocytes; and higher rates of glucose utilization and oxidation of the apoptotic resistant line relative to the wild type. There is an important difference in the ratio of glucose utilization to oxidation between normal and Fas or FasL deficient animals, with the ratio being higher for lymphocytes from both mutant strains of animals. The consequences of uncoupling are a decrease in mitochondrial membrane potential; use of fat as a carbon source increased rate of glycolysis, increased rate of electron transport, and energy dissipation, in a form other than ATP. These data suggest that there is an increase in proton leak in the cells with high rates of glucose oxidation and utilization relative to the normal cells, suggesting some degree of uncoupling may have occurred in these cells.

3. Fas Expression Increases as a Function of Glucose: We investigated the effect of increasing concentrations of glucose on cell surface Fas expression. L1210 and L1210/DDP cells were cultured in glucose free RPMI media or in media supplemented with insulin and glucose for 16 hours. Intra- and extracellular Fas expression was determined by labelling the cells with FITC-conjugated anti-Fas antibodies (Pharmingen), or FITC-conjugated isotype control, then subtracting the fluorescence intensity of the isotype staining from Fas staining for each treatment group.

Figure 2:
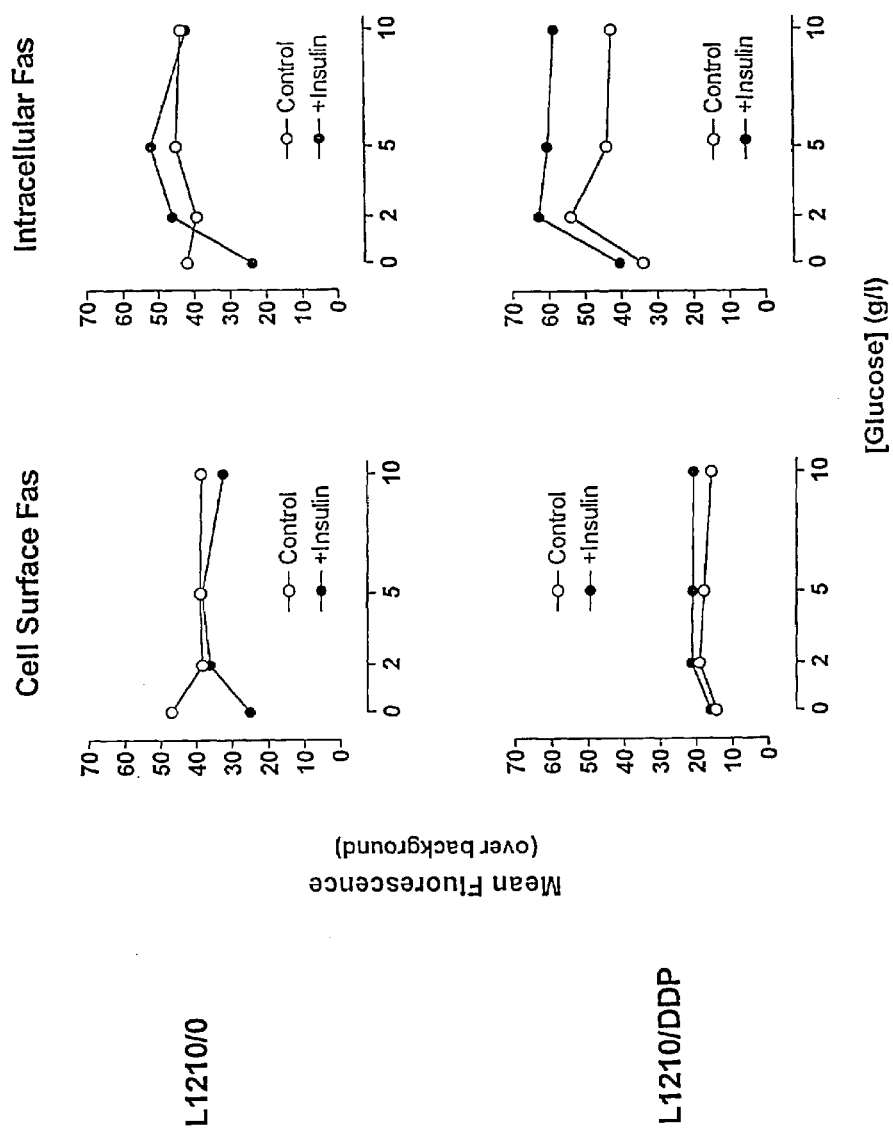
FIG. 2 shows Intracellular and surface Fas Expression on L1210, upper panels, and L1210/DDP cells, lower panels.

These data show that Fas expression increases as a function of glucose concentration, FIG. 2, and that as a result the cell surface Fas negative L1210/DDP begin to express cell surface Fas.

L1210, upper panels, and L1210/DDP cells, lower panels, were cultured in glucose free RPMI media, filled circles, or in media supplemented with insulin and glucose, squares, for 16 hours. Intra- and extracellular Fas expression was determined by labelling the cells with FITC-conjugated anti-Fas antibodies, or FITC-conjugated isotype control, then subtracting the fluorescence intensity of the isotype staining from Fas staining for each treatment group (FIG. 2). Results are presented as geometric mean fluorescence over background.

Figure 3:
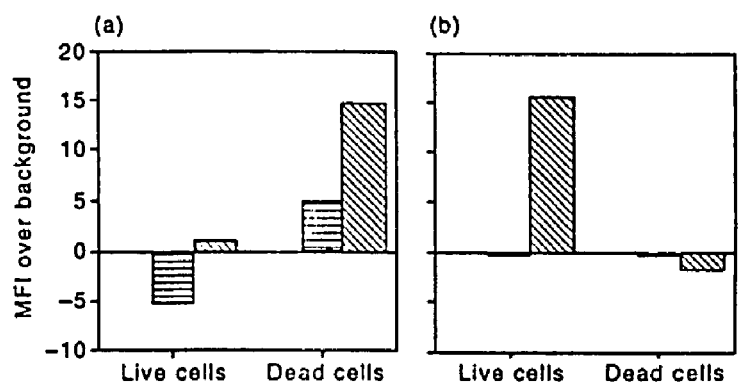
FIG. 3. Shows that treatment of L1210 DDP cells with staurosporin restores Fas expression and susceptibility to drug-induced apoptosis.

4. Treatment of L1210 DDP cells with staurosporin restores Fas expression and susceptibility to drug-induced apoptosis: L1210, but not L1210 DDP, undergo apoptotic cell death. We treated L1210 or L1210 DDP cells with the staurosporin, which inhibits protein kinase C and increases mitochondrial membrane potential, or an anti-cancer agent to which both cells are sensitive, adriamycin. Fas expression was increased or induced on both L1210 and L1210 DDP, respectively, in the presence of staurosporin or adriamycin (FIG. 3). The L1210 DDP changed morphologically and began to divide rapidly, changes which appeared to correspond with a reversion back to the phenotype of the L1210 cells. These results demonstrate that Fas expression results in parallel with altered metabolic activity.

FIG. 3 shows the treatment of L1210 DDP cells with staurosporin restores Fas expression and susceptibility to drug-induced apoptosis.

5. Confocal microscopy reveals that resistance to apoptosis is characterized by intra-(but not extra) cellular Fas expression: L1210 DDP cells express no cell surface Fas. To address the possibility that Fas is expressed, but has been targeted to a subcellular organelle, we permeabilized and stained L1210 and L1210DDP cells with fluorochrome conjugated anti-Fas antibody (J02.2, Pharmingen). The cells were examined by confocal microscopy. (This experiment was representative of four experiments).

Our data indicate that L1210 DDP cells express Fas in an intracellular, cytosolic compartment. Fluorochrome-conjugated isotype matched antibody was used as control. Additionally, these data also demonstrate that the Fas negative, apoptosis resistant cells, express intracellular Fas.

6. Fas-deficient (lpr) lymphocytes express intra-(but not extra-) cellular Fas molecules: We isolated lymphocytes from spleens of C57BL/6 mice and from C57BL6 transgenics having the lpr mutation (loss of Fas sensitivity). Cells were stained with fluorescein conjugated hamster anti-Fas and examined by confocal microscopy.

Results demonstrate that unstimulated, non-permeabilized splenocytes from C57BL/6 animals express Fas at low levels relative to isotype controls. Interestingly, significant levels of Fas expression were detected in permeabilized normal lymphocytes. As expected, non-permeabilized cells from C57BL6.lpr animals express no detectable cell surface Fas relative to isotype control. Interestingly, intracellular Fas staining of permeabilized splenocytes from C57Bl/6.lpr animals reveals intracellular expression of Fas. These results demonstrate that mutations affecting susceptibility to Fas-induced death prevent cell surface, but not intracellular expression of the Fas molecule.

7. Anti-cancer agents induce susceptibility to Fas-induced cell death: To determine if the anti-cancer agent methotrexate sensitizes L1210 or L1210/DDP cells to Fas induced cell death, we cultured L1210 cells in the presence or absence of $10^{-8}$ M methotrexate for 72 hours. Each group of cells was cultured on uncoated plates or plates coated with 10 g/ml anti-Fas (Jo.2.2, Pharmingen). We analyzed cell death using flow cytometry. Forward angle and 90 degree light scatter were used to distinguish between live and dead cells. Dead cells were gated as forward angle light scatter low/high ethidium bromide retaining cells. Percent death was calculated over the total number of cells acquired. In Table 3 below, values indicate % dead cells over background of untreated cells.

TABLE 3

| | Fas-induced cell death | |
|---|---|---|
| | L1210/0 | L1210/DDP |
| Control | 4.72 | 40.88 |
| anti-Fas Coated Plates | 79.98 | 46.60 |

Additionally, L1210 and L1210DDP cells were treated with 10–8 M methotrexate for 24 hours. Flow cytometric analysis revealed two populations based on forward side scatter. The forward scatter high populations did not take ethidium bromide and were therefore viable. The forward scatter low populations took up ethidium bromide differentially. The L1210 cells took up a moderate amount. Analysis of DNA fragments reveals that L1210 produced a ladder of nucleosome sized fragments indicative of apoptosis, whereas L1210/DDP cells did not. This latter phenotype—loss in forward scatter and membrane permeability with no "DNA laddering"—is the hall mark of oncosis.

8. Fas Deficient Lymphocytes are also drug resistant to methotrexate: We isolated splenic lymphocytes from aged-matched wild type C57BL/6 mice and C57BL6.lpr and C57BL.gld. Splenocytes from C57BL/6 lpr or gld animals were isolated, red cells depleted, and single cell suspensions prepared. Cells were cultured in the absence or presence of $5 \times 10^{-8}$ M methotrexate for 18 or 32 hours. Cells were harvested and viability was determined by flow cytometric analysis and confirmed with trypan blue exclusion.

The data demonstrate decreased susceptibility to methotrexate-induced apoptosis in Fas deficient lymphocytes. These data are consistent with the notion that Fas is required for drug susceptibility.

Figure 4:
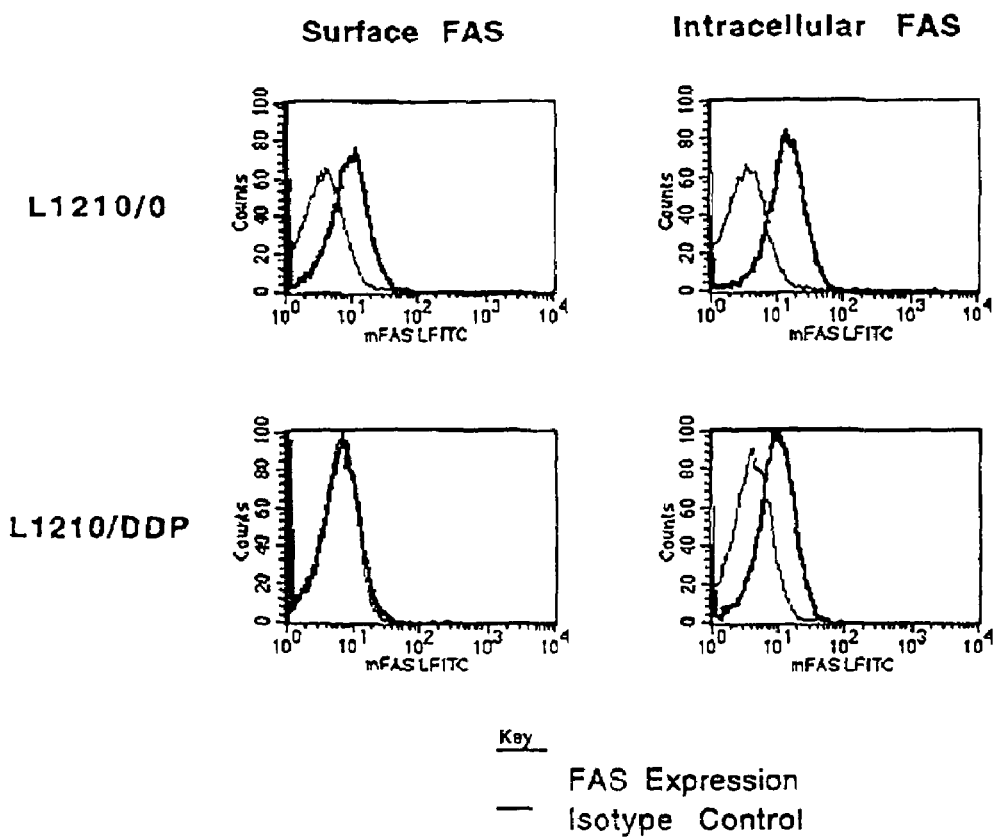
FIG. 4 is a graph showing wild type and/or drug resistant cells express intracellular and surface Fas.

9. Drug resistant cells express intracellular fas, UCP and bcl-2: We determined if wild type and/or drug resistant cells express intracellular and surface fas, UCP and bcl-2 (FIGS. 1A and 4). We stained non-permeabilized L1210 and L2120/DDP cells for cell surface or intracellular Fas. The data show that while there is no cell surface expression of Fas on the drug/apoptotic resistant cells, the drug resistant cells express high levels of intracellular Fas.

These data show that drug resistant cells are cell surface Fas negative and protected from death resulting from changes in mitochondrial membrane permeability transitions.

Example 2

Pancreatic B Cells Express UCP and have No Cell Surface Fas

1. Loss of antigen in β-cell tumors: Proliferation with two responder T cell clones, BDC-2.5 and BDC-6.9, was tested using NOD peritoneal cells as APC and as antigen, either freshly prepared NOD islet cells (control) or β tumor cells, or NIT-1, an established beta tumor cell line from the NOD-RIPTag mouse. Upon harvesting the islet tumors, the β-cells obtained are fully as antigenic as normal NOD islet cells. The NIT-1 line is also antigenic for these T cell clones, but only at low passage numbers; with continued culture, the line changes its morphology and growth kinetics and undergoes complete loss of antigen.

2. Response of pancreatic β-cells to glucose: The experiments described below were designed to test the hypothesis that β cell metabolism may be linked to immune recognition and destruction. Glucose utilization was measured as $[^3H]$ $H_2O$ production from 5-$[^3H]$glucose in normal rat islets. Glucose oxidation was measured as $[^{14}C]CO_2$ production from U-$[^{14}C]$glucose.

Figure 5:
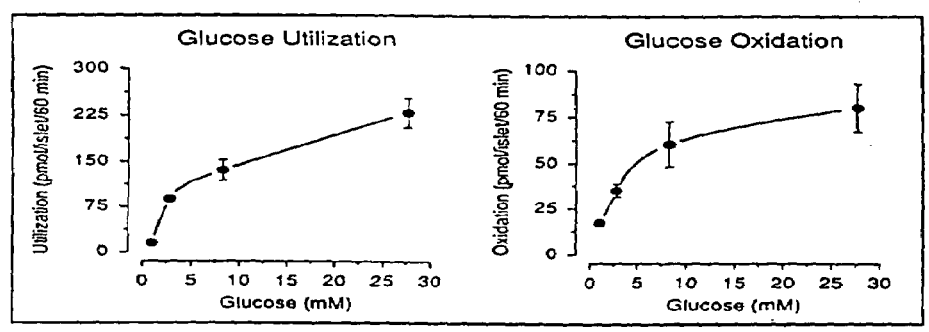
FIG. 5. Is a graph showing glucose utilization and oxidation in normal rat islets.

The data show increasing glucose utilization and oxidation in β-cells as a function of increasing glucose concentration. FIG. 5 depicts the measurements for glucose oxidation and utilization (representative of many experiments). The expected values of β-cells from normal animals is illustrated in FIG. 5.

FIG. 5 shows glucose utilization and oxidation in normal rat islets. Glucose utilization was measured as $[^3H]H_2O$ production from 5-$[^3H]$glucose. Glucose oxidation was measured as $[^{14}C]CO_2$ production from U-$[^{14}C]$glucose.

3. Normal β-cells Express Intracellular UCP2 and No Cell Surface Fas: Normal β-cells have a specialized glucose response which is based on the cell being responsive to physiologic glucose concentrations. The process that mediates the glucose responsiveness is the process involving flux through glycolysis. β-cell glucose usage is mediated through a relatively unique system that entails specialized high $K_m$ glucose transporter (GLUT2) and glucose phosphorylation isoforms (glucokinase). We isolated β-cells from C3H mice, stained the isolated cells with anti-Fas, and electronically gated viable cells. In parallel, cells were permeabilized and stained with an antibody to UCP2 (kindly provided by Drs. Jean Himms-Hagen and M. E. Harper).

The results show that normal β-cells express intracellular UCP2 and no cell surface Fas.

4. Fas Expression and Mitochondrial Membrane Potential are a Function of Glucose Concentration in Mouse β Cells.

The central question is whether Fas expression is altered by changes in physiological glucose concentrations in normal β cells and does the mitochondrial membrane potential increase, suggesting that cell has ATP synthesis resulting from increased rates of electron transport. Our data, FIG. 6, suggest that as glucose concentration, the large β cell subset of gated cells have increased Fas expression and concomitant increased mitochondrial membrane potential, while the smaller (possibly alpha, glucagon producing cells) do not.

Figure 6:
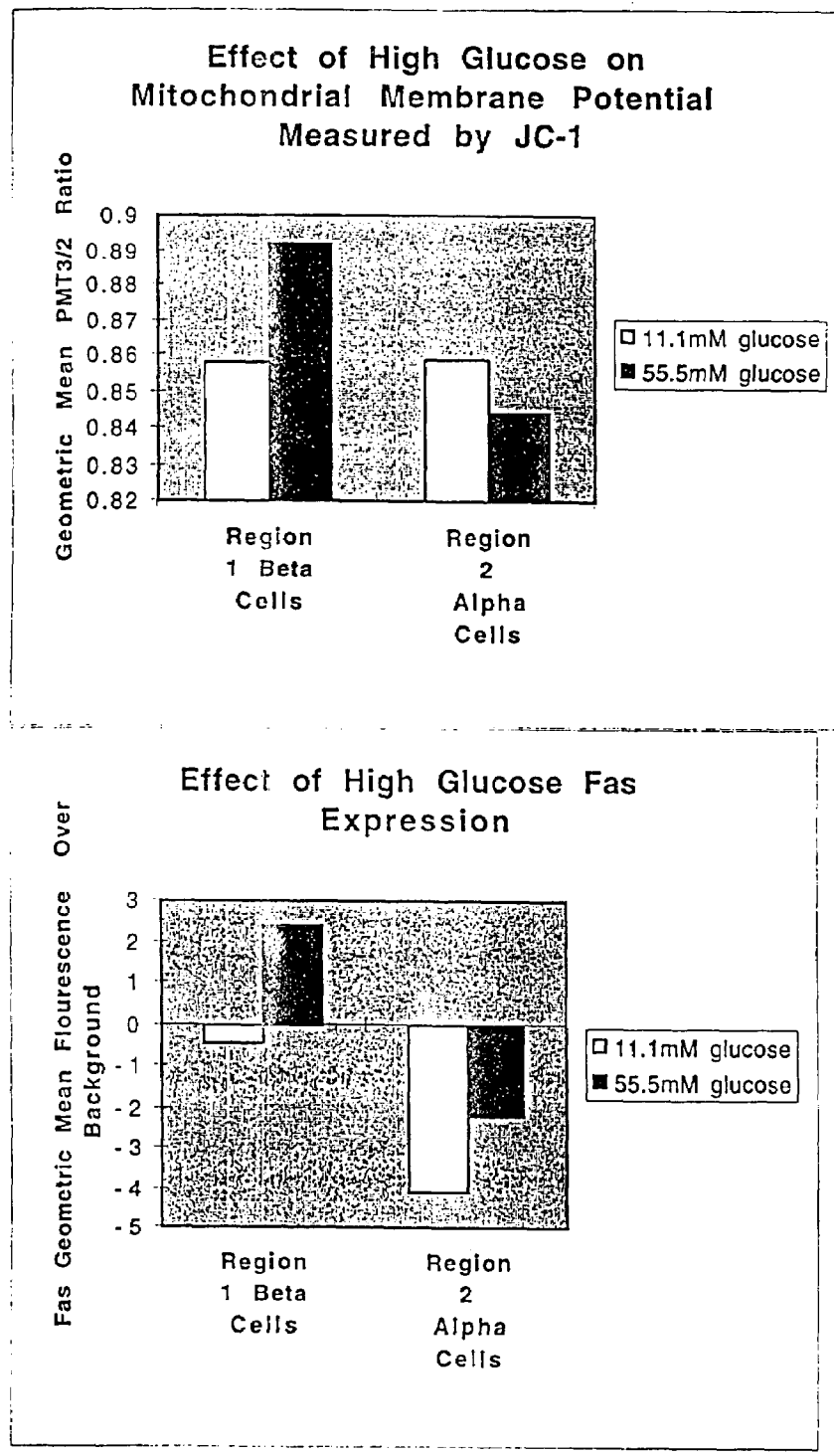
FIG. 6 is a graph showing that glucose concentration, the large β cell subset of gated cells have increased Fas expression and concomitant increased mitochondrial membrane potential, while the smaller (possibly alpha, glucagon producing cells) do not.

In FIG. 6 islets were isolated and dispersed with trypsin and a cell strainer. Debris and dead cells were removed and applying the cells to a 1.066 Percoll gradient. Electronic gating of the cells was used to segregate the populations of islets cells. The region with larger cells were gated β cells (13, 14) where the region with smaller cells were gated as alpha cells (13, 14). Other larger cells were excluded because they contained δ cells. The cells were treated overnight with either physiological 11.1 mM glucose or high glucose 55.5 mM glucose. Fas expression was determined by staining with a FITC conjugated antibody. Mean fluorescence of staining with isotype control antibody was subtracted. Measurement of mitochondrial membrane potential was measured using JC-1 as a fluorescence probe (15, 16). The relative membrane potential was read by taking the red mean fluorescence (aggregated JC-1 labeled) divided by mean green fluorescent (monomeric JC-1) labeled fluorescence (15, 16).

5. Determination of Mitochondrial Membrane Potential in β Cells Isolated from Four Strains of Animals.

Figure 7:
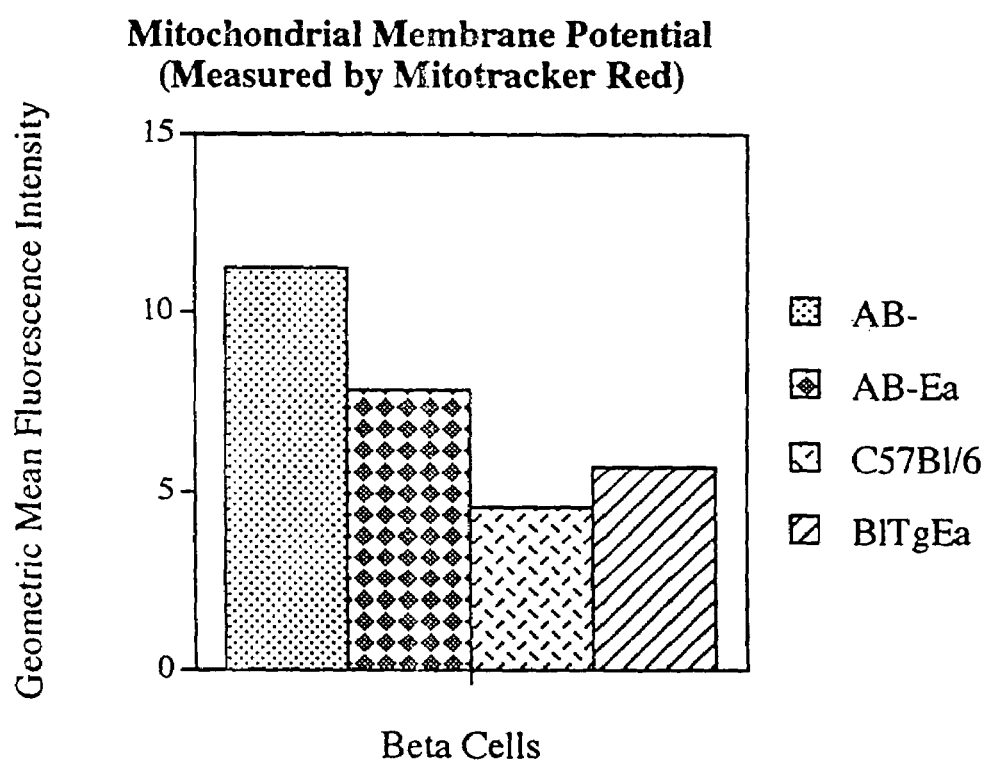
FIG. 7 shows mitochondrial membrane potential, assessed flow cytometrically using mitotracker red.

As shown in FIG. 7 mitochondrial membrane potential is assessed flow cytometrically using mitotracker red. The amount of membrane potential was measured in the four strains of animals AB-, AB-Ea, C57Bl/6, BITgEa, described in more detail below.

Example 3

Relationship Between the Metabolic State of a Cell and Expression of MHC Class II Molecules 1. Analysis of the Mechanisms of Signaling Through MHC class II Molecules i. Perturbation of Class II on Resting B Cells Results in the Generation of cAMP.

Figure 8:
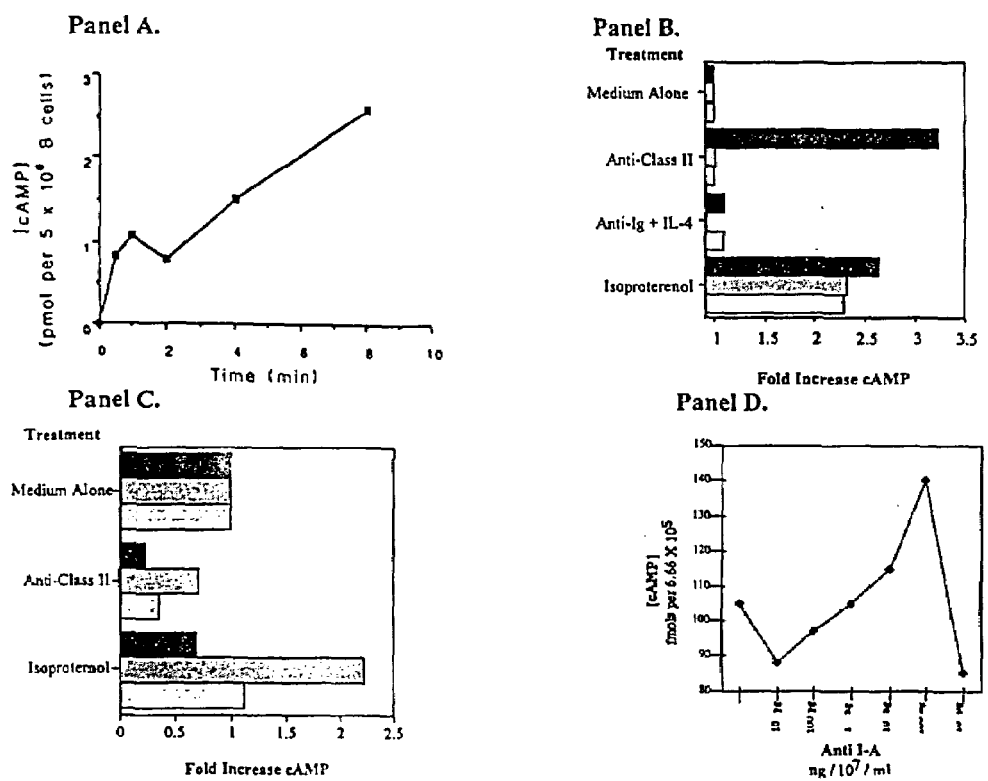
FIG. 8 shows a comparative analysis of alterations in levels of cAMP.

Early studies demonstrated that ligation of IE molecules on resting B cells resulted in the rapid generation of intracellular cAMP in those cells (Cambier, et al., Nature (1987). Based on this observation and on our more recent evidence that elevated levels of cAMP correlate with death in resting B cells, we have studied the generation of cAMP in more detail. These data are compiled in FIG. 8, panels A, B, C, and D. The data in this figure allow a comparative analysis of alterations in levels of cAMP as induced by antibodies to IE, FIG. 8, panels A and B; mAb to IA (From ATCC), FIG. 8, panels C and D. In FIG. 8B, cells were stimulated with antibodies to MHC class I (From ATCC), with anti-Ig (Jackson Immunochemicals) and IL-4 (Genzyme), or with isoproteronol (Sigma) as indicated. In panel C, we isolated B cells from C57BL (which express IA, but not IE molecules) wild type, lpr, or gld animals. The data in panel C show that the lpr, or gld mutation does not alter the signal delivered by MHC class II engagement at the dose of the anti-IA mAb that we have used.

FIG. 8 shows comparative analysis of alterations in levels of cAMP as induced by antibodies to IE, panels A and B; mAb to IA, panels C and D. In panel B, cells were stimulated with antibodies to MHC class I, with anti-Ig and IL-4, or with isoproteronol as indicated. In panel c, we isolated B cells from C57BL (which express IA, but not IE molecules) wild type, lpr, or gld animals. Dose titration of anti-IA stimulation on B cells from C57BL/6 animals, panel D.

These data show that under the conditions we have employed to stimulate the cells, the anti-IE antibodies are more effective at increasing intracellular cAMP. To investigate the possibility that the differences in the ability of IA and IE to alter levels of cAMP may be the consequence of dose dependent differences and to determine if anti-IA antibodies ever induce increase in cAMP, we performed a dose titration of anti-IA stimulation on B cells from C57BL/6 animals, (panel D). These data demonstrate an oscillation of cAMP levels, and reflect alteration in signaling by differences in aggregation state of MHC class II.

Figure 9:
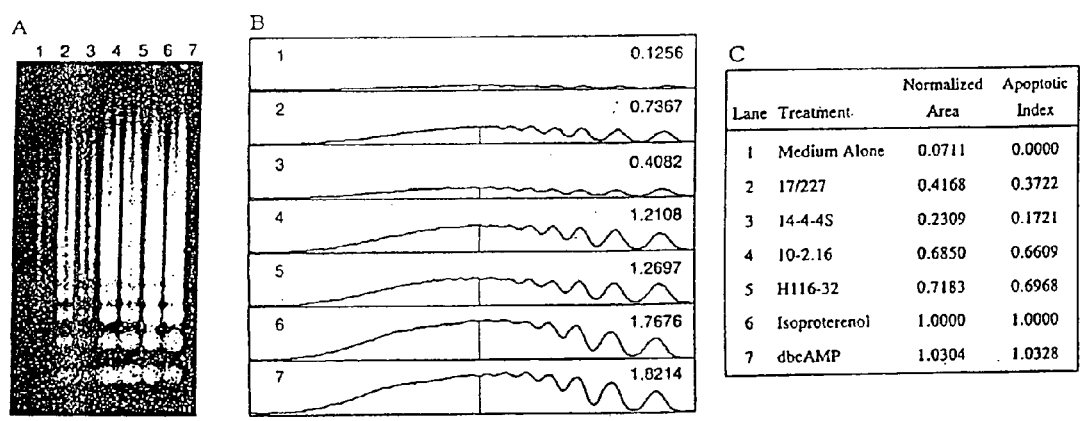
FIG. 9 shows an analysis of DNA fragmentation from resting B cells.

FIG. 9 shows an analysis of DNA fragmentation from resting B cells. A Cells were incubated with medium alone, with antib class II (IA), anti-class II (IA beta chain), anti-class II IE, isoproteronol, or dibutyryl cAMP, lanes 1 through 7 respectively, Panel A, and cultured overnight. Cells were harvested, nuclei separated, and fragmented (non-clear) DNA precipitated and the samples were electrophoresed on agarose gels. Bands were visualized using ethidium bromide and ultraviolet light detection. Bands were quantitated using scanning densitometry, panel B. Quantitated area is presented in panel C.

ii. Anti-Class II mAb Induce an Increase in Apoptotic Cell Death in Resting B Cells.

Our data demonstrate that treatment of resting B lymphocytes with anti-class II mAb results in B cell apoptosis, as measured by increases in nucleosome-sized DNA fragments. These are detected by agarose gel electrophoresis and quantitated densitometrically. Apoptotic indices are generated by comparison to maximum apoptotic death as stimulated by isoproterenol (FIG. 10).

Figure 10:
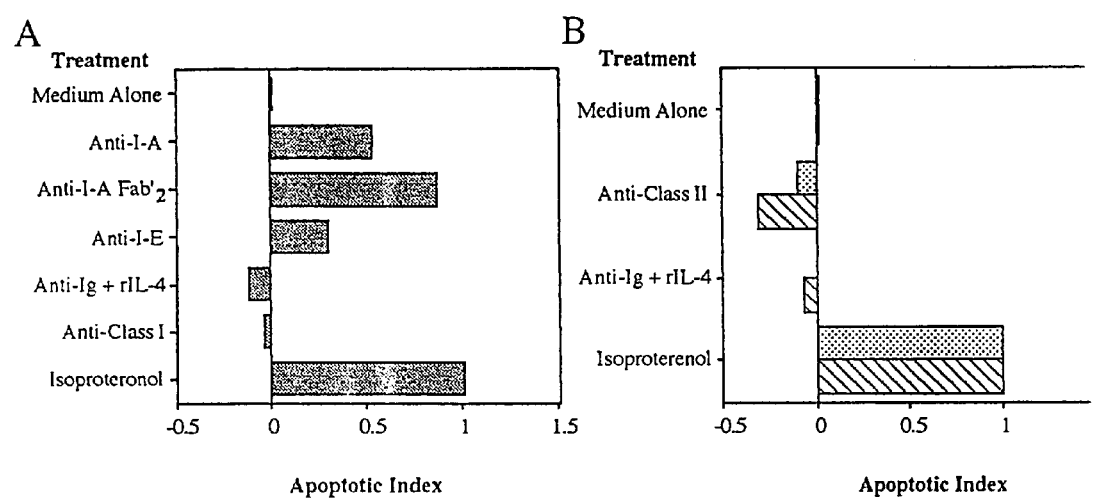
FIG. 10 shoes that treatment of resting B lymphocytes with anti-class II mAb results in B cell apoptosis, as measured by increases in nucleosome-sized DNA fragments.

FIG. 10 shows ligation of class II molecules on resting, but not activated B cells, results in apoptotic death. Resting B cells, (white bar, black dots); in vitro activated B cells [anti-Ig and recombinant IL-4], (parallel lines bar); or freshly ex vivo activated cells, (black bar, white dots); were treated with 10 μg/ml anti-I-$A^k$ mAb (17/227); anti-Ig and 16 units of recombinant IL-4, or 10 μM isoproteronol. B cells were treated with the stimuli indicated for 10 min at 37° C., cultured overnight, harvested and assayed. (The in vitro activated cells were not treated with additional anti-Ig plus rIL-4.) Fragmented DNA was isolated by centrifugation and run on agarose gels. The ethidium bromide stained gel was photographed and scanned. An Apoptotic Index was calculated by taking: [(experimental area−area with medium alone)/(area with isoproterenol−area with medium alone)]. Treatments that produce a score of 0 show background levels of apoptosis, whereas treatments that are protective produce scores <0. Data from four independent experiments are averaged for normal animals; means and standard errors are shown. Means of two independent experiments for the freshly ex vivo activated cells and a single experiment for the in vitro activated cells are shown.

iii. MHC Class II Induced Death in Resting B-Cells from Normal Mouse Strains, but not Mouse Strains Having the lpr and gld Mutations.

To test the hypothesis that the mechanism of IA-mediated death involves the receptor ligand pairs CD95/CD95L, we have used mouse strains that have the lpr mutation, or the gld mutation, which have defects in CD95 and CD95L, respectively (Watanabe-Fukunaga, R, et al., Nature (London), 1992, 356, 314-317; Suda, T et al., Cell, 1993, 75:1169-1178). Total splenic B-cells were isolated from C3H, AKR, C3H.lpr, and MRL.gld mice. All of these strains are H-$2^k$. The cells were cultured overnight, harvested, permeabilized in saponin, stained with propidium iodide (PI) which intercalates into DNA, and analyzed by flow cytometry. After a 15 hour culture, a significant percentage of cultured B-cells fragment their DNA, with no stimulation (Newell, M K, et al., *Proc Nat Acad Sci USA,* 1993, 90:10459-10463). Crosslinking MHC class II IA (HLA-DP/DQ in humans) on B-cells from the wild type animal cause an increase in apoptosis. Unlike the normal B-cells, there is no increase in less than 2×DNA after crosslinking MHC class II on B-cells from lpr or g/d mice.

2. Interaction of B-cells with T cells: The results of mAb binding to MHC class II does not, a priori, reflect the result of an interaction with a physiologically relevant ligand. To address the possibility that the physiological ligand for MHC class II is expressed on a CD4+ T cell, we examined the effect of class II signaling resulting from T cell:B cell interactions, Table 4. Resting splenic B-cells were isolated by T depletion and density gradient centrifugation (Percoll). The B-cells were then combined with either an autoreactive I-Ak-specific T cell hybridoma (Kal-68.4) or with a hen egg lysozyme (HEL) peptide-specific, I-Ak-restricted T cell hybridoma (A6.A2) either with or without a tryptic digest of lysozyme as the source of the required peptide. Cells were cultured overnight at 37° C. and then examined under a fluorescence microscope. Apoptotic cells were scored based on their morphology and on their uptake of Hoechst Dye 33342 at 5 µg/ml final concentration (Cohen, J. J, et al., *Ann Rev Immun,* 1992, 10, 267-293). B and T cells were distinguished by morphology.

TABLE 4

Induction of apoptosis in resting, but not activated, AKR B cells by interaction with T cells

| Culture Additions[a] | Resting B cells | | Activated B cells | |
|---|---|---|---|---|
| | % Apoptotic B cells | IL-2 Titer, U/ml | % Apoptotic B cells | IL-2 Titer, U/ml |
| Medium Alone | 14 | <20 | 25 | <20 |
| A6.A2[b] | 13 | <20 | 18 | <20 |
| A6.A2 + tryp-HEL[c] | 54 | 1280 | 25 | 1280 |
| Kal-68.4[d] | 30 | 160 | 22 | 320 |

[a]Equal numbers (5 × 10$^5$) of B-cells and T cells were incubated for 16 hr at 37° C. in a 24 well microtiter plate.
[b]A6.A2 is I-Ak-restricted T cell hybridoma specific for the hen egg lysozyme peptide HEL(aa34-45). IL-2 titers were determined using HT-2 cells as previously described (36).
[c]Tryptic digest of HEL, containing HEL(aa34-45), was used at 1 mg/ml.
[d]Kal-68.4 is an autoreactive I-Ak-specific T cell hybridoma.

3. Phenotypic characterization of apoptotic B-cells: We adapted the technique of using terminal deoxynucleotidyl-transferase (TdT) to add fluorochrome-conjugated deoxyribonucleotides to the free ends of DNA to flow cytometric analysis of apoptosis (Gold, R, et al., *J Histochem Cytochem,* 1993, 41:1023-1030). Because the fragmented DNA of apoptotic cells has significantly more free ends that DNA of non-apoptotic cells, the apoptotic cells stain bright green with dUTP-FITC (deoxyuridine triphosphate) whereas viable cells remain dull. After a 16 hr incubation with the Kal-68.4 autoreactive T cell hybridoma, resting B-cells from AKR mice showed 46-47% apoptotic cells, confirming the results using the two other methods. This method allows a counter-stain of cells with antibodies directed against various surface receptors expressed by the B-cells.

Figure 11:
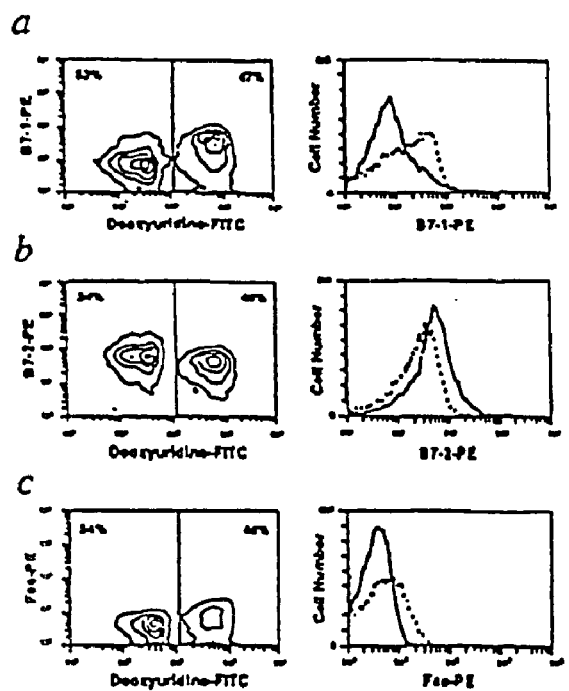
FIG. 11 shows a two-color flow cytometric analysis of apoptotic resting B-cells.

Relative to resting B-cells, B-cells cultured overnight with Kal-68.4 upregulated B7-1, B7-2 and Fas, with the upregulation of B7-1 being the most striking and giving rise to a bimodal distribution (left hand panels, FIG. 11). Two-color analysis reveals that the B-cells from these cultures may be divided into viable (deoxyuridine-FITC low) and apoptotic (deoxyuridine-FITC high) populations with apparent differential expression of the counter-stained receptors on the two populations. Histograms of fluorescence intensity of the stained receptors (right panels, FIG. 11) show that Fas (FIG. 11c) and especially B7-1 (FIG. 11a) are upregulated on the apoptotic population whereas B7-2 (FIG. 11b) is expressed at higher levels on the viable population.

FIG. 11 shows a two-color flow cytometric analysis of apoptotic resting B-cells. AKR resting B-cells and Kal-68.4 T hybridomas cells were incubated overnight. Cells were stained with biotin-conjugated mAb directed against B7-1 (a), B7-2 (b), or Fas (c) followed by PE-streptavidin, and apoptotic cells were detected using TdT/dUTP-FITC. The contour plots on the left of each section show labeling with dUTP-FITC (as a measure of apoptotic death) versus counter-staining with the indicated mAb for B-cells harvested from culture with T cells. The percentages indicate the relative number of cells in the viable (dUTP-FITC dull) and apoptotic (dUTP-FITC bright) populations. The histogram on the right of each section shows the relative staining levels with the indicated mAb of the viable (solid line) and the apoptotic (dashed line) populations as gated by dUTP-FITC fluorescence in the contour plots.

4. Class II-Mediated Signaling in (NZB×NZW)F1 and (NZB×SWR)F1 Mice i. Engagement of Class II on Resting B-Cells from Autoimmune Strains of Mice Does not Result in Increases in cAMP Over Background Levels.

Figure 12:
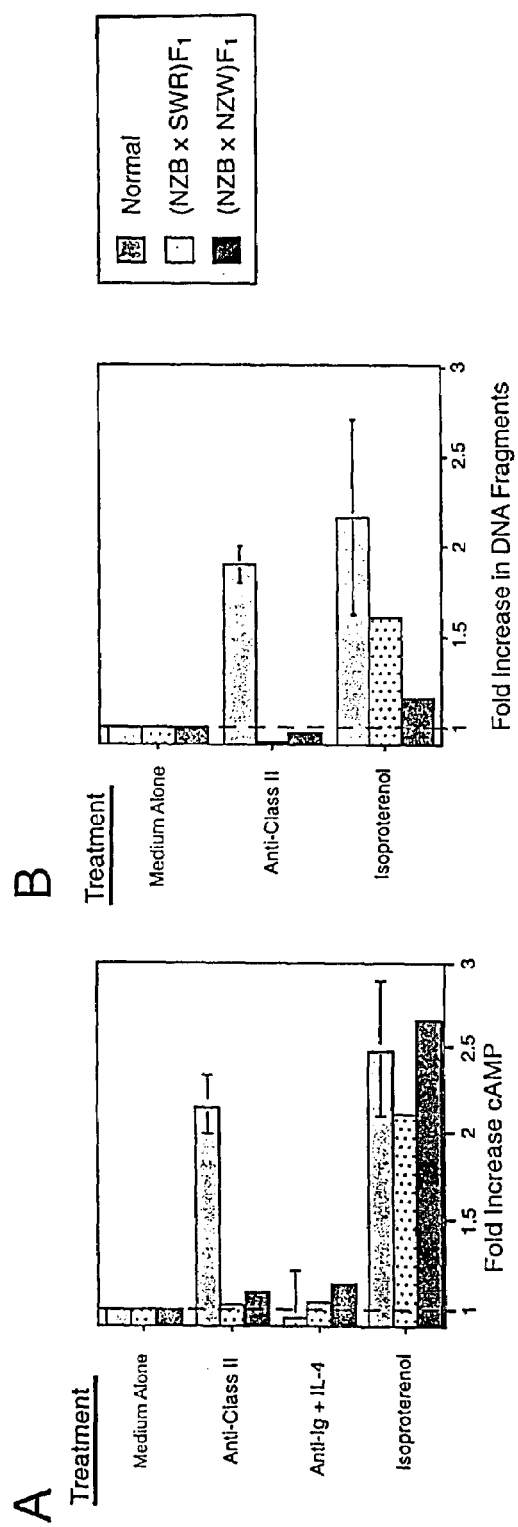
FIG. 12A demonstrates that in contrast to B-cells from normal mice, resting B-cells from (NZB×SWR)F1 and (NZB×NZW)F1 mice do not elevate intracellular cAMP in response to ligation of their class II molecules.
FIG. 12B shows a ligation of class II molecules on resting B-cells from (NZB×NZW)F1 and (NZB×SWR)F1 animals does not result in apoptotic death.

Experiments with B-cells from (NZB×NZW)F1 and (NZB×SWR)F1 mice suggested a potential link between class II-mediated B cell signaling and autoimmunity in these mice. Following the protocols as described in Newell, M K, et al. (*Proc Natl Acad Sci, USA,* 1993, 90:10459-10463) for resting B lymphocytes from normal mice, we isolated resting B-cells from spleens of (NZB×NZW)F1 and (NZB×SWR)F1 mice by Percoll gradient separation and treated the cells with antibodies to class II molecules, FIG. 12. Experiments utilized mice younger than 3 months of age. These mice do not have elevated serum levels of IgG autoantibodies to histone and DNA and do not demonstrate evidence of an immune-complex glomerulonephritis.

FIG. 12A demonstrates that in contrast to B-cells from normal mice, resting B-cells from (NZB×SWR)F1 and (NZB×NZW)F1 mice do not elevate intracellular cAMP in response to ligation of their class II molecules. In contrast, the response to isoproterenol is normal. It should be noted that there are no significant differences between resting cells in normal versus (NZB×SWR)F1 mice, as defined by surface MHC class II expression and by density (Julius, M and Haughn, L, *Eur J Immun,* 1992, 22, 2323-2329).

FIG. 12A shows class II ligation of resting B-cells from (NZB×NZW)F1 and (NZB×SWR)F1 animals does not result in increases in cAMP. Resting (1.079<r<1.085) B-cells from normal, (NZB×SWR)F1, or (NZB×SWR)F1, animals were treated for 10 min at 37° C. with stimuli indicated. Levels of cAMP were determined as described in FIG. 1. Means (and standard errors) from three experiments are shown for normal animals. The means from two experiments are shown for each of the F1 hybrid animals.

ii. Class II-Mediated Apoptosis Does not Occur in Resting B Lymphocytes from Autoimmune Mice.

We stimulated both resting and activated B-cells from (NZB×NZW)F1 and (NZB×SWR)F1 mice with antibodies to class II molecules. Young animals, prior to the development of lupus-like autoantibody and renal disease, were used in these studies.

Data demonstrates that in contrast to normal B-cells, resting B-cells from (NZB×NZW) F1 and (NZB×SWR) F1 mice are refractory to MHC class II-mediated apoptosis. FIG. 12B also shows that despite normal cAMP generation after isoproterenol, this treatment induced minimal evidence of apoptosis in (NZB×NZW)F1 B-cells. An intermediate level of isoproterenol-induced apoptosis was apparent in B-cells from (NZB×SWR)F1 mice. Thus, the collective results demonstrate that, while resting B-cells from both autoimmune strains are defective in coupling the ligation of class II molecules to the generation of cAMP, cells from (NZB×NZW) F1 animals also appear to have a second lesion in the apoptotic pathway that is downstream from the generation of cAMP.

FIG. 12B shows a ligation of class II molecules on resting B-cells from (NZB×NZW)F1 and (NZB×SWR)F1 animals does not result in apoptotic death. Agarose gel electrophoresis of DNA fragments from high density resting B-cells (1.079<r<1.085) was carried out as described in FIG. 2. Normalized areas produced by scanning densitometry on the gels shown above for normal, (NZB×SWR)F1, or (NZB×NZW)F1, animals. The data were normalized to background levels rather than calculating an Apoptotic Index since (NZB×NZW)F1 cells did not show a significant increase in apoptosis when treated with isoproterenol. For normal animals, the mean and standard error of four experiments are shown. For the (NZB×NZW)F1 animals, representative data from one of two experiments is shown and for (NZB×SWR) F1 animals, a single experiment is shown. Because experiments were performed on different days it is impossible to compare background levels of apoptosis between strains; however, it should be noted that there is significant variability in background levels of apoptosis, with those for the (NZB×NZW)F1 animals apparently tending to be higher than for the other strains.

iii. Phenotypic Characterization of Apoptotic B-Cells from Autoimmune Prone Mice Our results show that when using B-cells from (NZB×NZW)F1 animals resting B-cells from these animals are refractory to class II-induced apoptosis. This indicates that a failure of class II mediated apoptosis provides a mechanism for polyclonal hyper-agammaglobulinemia, characteristic of autoimmune disease. Resting B-cells are able to present sufficient self peptides to allow their interaction with the "autoreactive" T cells and that the failure to obtain class II-mediated apoptosis in resting B-cells may drive polyclonal hyper-agammaglobulinemia.

Figure 13A:
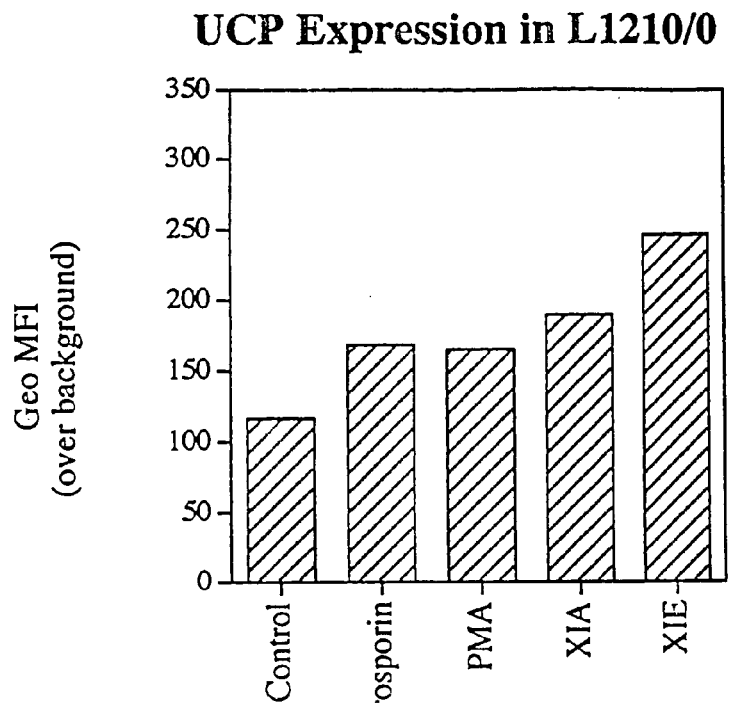
FIG. 13 shows UCP expression in L1210 and L1210/DDP cells in response to staurosporin and PMA.
Figure 13B:
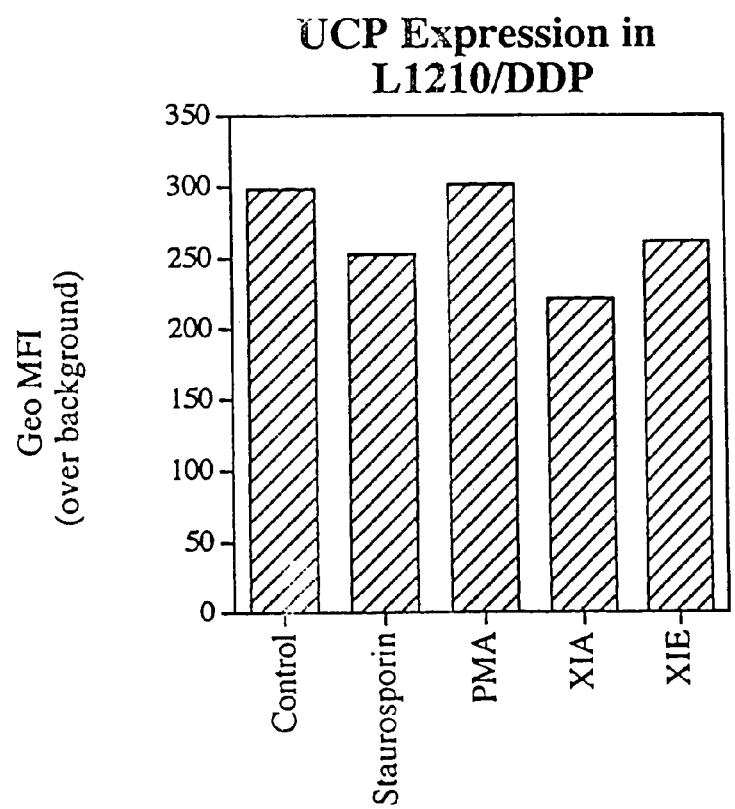

5. Structural Features and Cell Surface Expression of MHC IA and IE Molecules Associated with Cell Death FIG. 13 shows UCP expression in L1210 and L2120/DDP cells in response to staurosporin and PMA.

Sequence of MHC IA and MHC IE Molecules

Comparison of the transmembrane (TM) and cytoplasmic (Cy) domain sequences of the beta and alpha chains of $IA^k$ and $IE^k$ reveals both conserved and unique sequences. The differences between IA and IE and the human equivalents are generally shared. The beta chains of $IA^k$ and $IE^k$ have 18 of 22 amino acids that are conserved in the TM domain. These changes are basically conserved, whereas the Cy domains differ in length and composition. The Cy domains of $IA^k$ has more two more prolines and an extra two positive chargres (R, H) at the proximal end of the Cy domain next to the inner leaflet. The area (RH<u>RSQKGP</u>) (SEQ ID NO. 13) of the Cy domain of $IA^k$ that has been mapped by Wade et al (*Int Immunol*, 1994, 6:1457-1465) as being required for PKC translocation and cAMP, respectively, is different from the sequence seen in IE, but the residues QKG are the same. This sequence similarities may explain the observation that ligation of IA or IE can signal increases in intracellular cAMP. The lack of the RH or PP residues in IE could explain the lack of Fas induction, due to either the loss of a binding site defined by the positive charges of the kinks introduced in the Cy domain by the multiple P residues.

6. Correlation between surface expression and type of cell death. Cell Surface Phenotype of MHC Class II+ Cells. Much of our work is based upon the use of model cell lines which have been transfected with wild type or mutated MHC class II molecules and which exhibit each of the prototypic signalling phenotypes, M12.C3 and K46J, representing cAMP and Ca++ generating responses, respectively (Wade, W F et al., *Int Immunol*, 1994 6:1457-1465). The results of flow cytometric analysis to phenotype the cell surface marker expression on each of these lines is combined with a summary of what we know about the way cells die in Table 5. These data were generated either flow cytometrically by assessing changes in forward and side scatter with uptake of ethidium bromide, or by morphological assessment and trypan blue exclusion.

TABLE 5

Summary of Cell Surface Expression and Cell Death Phenotype

| | Cell Surface Phenotype | | | | Type of class II induced death (if any) | |
|---|---|---|---|---|---|---|
| | Fas | IE | B72 | B7-1 | Apoptotic | Osmotic Rupture |
| M12.C3 wt/wt | ++ | -- | -- | + | -- | ++++ |
| M12.C3 411-12/-18 | -- | -- | -- | + | -- | -- |
| M12.C3 7D3-12/wt | + | -- | -- | + | -- | + |
| K46J wt/wt | ++ | +++ | ++ | + | ++ | ++ |
| K46J-12/-18 | + | + | -- | + | ?? | ?? |

Example 4

Involvement of IA Versus IE in Resistance and Susceptibility to Immune-Mediated Cardiovascular Disease Coxsackievirus-Mediated Myocarditis To evaluate the role of MHC class II antigens in immune-mediated myocarditis susceptibility, transgenic mice were graciously provided by Dr. Chella David of Mayo Clinic. Dr. David supplied the following strains: 1) $AB^o$ mice lack MHC class II IA and IE molecules (class II knockout (KO) mice); 2) $AB^o$ $Ea^b$ are MHC class II KO mice which have a functional transgenic IE chain, so that the animal express IE but not IA; 3) Bl.Tg.$Ea^b$ mice express the wild type IA molecules as well as the IE molecules; and 4) wild type C57Bl6 express IA only.

Male mice, 4-5 weeks of age were injected ip with 100 μg GL3-3A (anti-γδ) monoclonal antibody in 0.5 ml PBS, or PBS alone on days -2 and +2 relative to virus. Animals received $10^4$ PFU CVB3 on day 0 and surviving animals were euthanized on day 7. Hearts were removed from animals between days 5 and 7 for analysis. Hearts were divided and the apex was formalin fixed, sectioned and evaluated by image analysis for percent of the myocardium affected. The remaining tissue was titered by plaque forming assay for virus. Groups consisted of 4 mice each. The results are summarized in Table 6 below.

TABLE 6

Effect of Depleting γδ+ T Cells on CVB3-Induced Myocarditis

| STRAIN | ANTIBODY | MORTALITY | VIRUS TITER | MYOCARDITIS |
|---|---|---|---|---|
| C57BL/6 | | 0 | 5.1 ± 0.7 | 0.5 ± 0.3 |
| | Anti-γδ TcR | 0 | 5.5 ± 0.9 | 0 ± 0 |
| $AB^o$ | | 0 | 6.5 ± 1.4 | 0 ± 0 |
| | Anti-γδ TcR | 0 | 7.1 ± 0.8 | 1.3 ± 0.8 |
| $AB^o$ Eαk | | 100 | 6.2 ± 0.9 | 5.1 ± 2.0 |
| | Anti-γδ TcR | 25 | 6.5 ± 0.7 | 1.8 ± 1.1* |
| Bl Tg Eαk | | 50 | 4.3 ± 0.5 | 8.3 ± 1.6 |
| | Anti-γδ TcR | 0 | 5.3 ± 0.4* | 1.7 ± 0.5* |

*Significantly different than non-antibody-treated mice at $P \leq 0.05$.

Mice expressing either no class II MHC antigen or IA only were myocarditis resistant having little or no cardiac inflammation and no animal mortality. In contrast, IE-bearing mice showed increased mortality accompanied by substantial myocardial necrosis. AB° Eα mice, expressing IE only, began dying earlier (day 3 post-infection) and had more extensive coaggulative myocardial necrosis with limited cardiac inflammation compared to Bl.Tg.Eα mice (both IA+ and IE+). Cardiac lesions in Bl.Tg.Eα mice were confined to regions of mononuclear cell infiltration and were characterized by extensive myocyte dropout. Viral titers also differed between mouse strains with the highest titers occurring in AB° and AB° Eα mice. This suggests that IA expression is important in virus clearance. Also, the elevated viral titers in AB° Ea mice must not be directly responsible for the necrotic heart lesions in this strain since AB° mice also have elevated virus concentrations but no histological evidence of cardiac injury. Thus, by either animal mortality or histology, the presence of IE in C57BL/6 mice aggravated CVB3-induced disease. Treating the BL tg Eα$^k$ strain with antibodies to deplete γδ T cells conferred resistance to myocarditis. We measured cytokine profiles from total splenocytes of the animals before and after infection. We observed increased γ-interferon in all strains and higher levels of IL4 in the Bl.Tg.Eα$^k$ animals. Depletion of γδ T cells resulted in an increased percentage of cells producing IL4 post infection (not shown). This result demonstrates that the cytokine bias is important in the development of myocarditic lesions.

Example 5

MHC Class II IE Molecules Confer Protection from Early Atherosclerotic Fatty Lesions Several studies suggest that CD4$^+$ T lymphocytes contribute to the pathogenesis of fat-induced atherosclerotic lesions (Emeson, E E, et al., *Am J Path*, 1996, 149:675-685). We addressed the possibility that expression of IA and/or IE impacted the development of lesions which result from a high fat diet.

C57BL/6 transgenic mice differing in MHC class II antigen expression were kindly supplied by Dr. Chella David (Mayo Clinic). Between 4 and 10 mice of each strain were placed on high-fat, high-cholesterol diet (Teklad #96354;20% total fat, 1.5% cholesterol, 0.5% sodium cholate) at three weeks of age and were killed 15 weeks later for evaluation of the aorta and splenocytes. An additional group of 7 C57BL/6 mice were placed on high-fat diet as above, but were injected ip every two weeks with 100 μg monoclonal rat anti-CD4 antibody (clone GK1.5; American Type Tissue Collection, Bethesda, Md.). This protocol has been used previously to maintain CD4+ T cell-deficient mice for extended periods in the experimental allergic encephalomyelitis (EAE) model. The heart and ascending aorta including the aortic arch were removed and evaluated for atherosclerotic lesions according to the method of Plump et al. using oil red-0 stained serial sections. Briefly, hearts were fixed in 10% buffered formalin, embedded in 25% gelatin, grossly cut through the ventricles parallel to the atria, frozen in OCT and sectioned by cryostat. Ten micron thick sections were placed on 5% gelatin coated slides, stained with 0.24% oil Red-0 (neutral lipids) and counterstained with 2.4% hematoxylin (nuclei and basophilic tissue) and 0.25% light green (remaining tissue). Lesions were quantified by area morphometry using a compound light microscope.

TABLE 7

MHC class II IE molecules confer protection from early atherosclerotic fatty lesions

| Strain | IA | IE | Treatment | Heart | Liver | Cholesterol |
|---|---|---|---|---|---|---|
| C57BL/6 | + | − | No Treatment | ++ | − (++ Lymph) | Not Significant |
| C57BL/6 | + | − | Anti-CD4 | + | − | Not Significant |
| AB° | − | − | No Treatment | +/± | +++ | Not Significant |
| AB°Eαk | − | + | No Treatment | −/± | +++ | Not Significant |
| BlTgEαk | + | + | No Treatment | −/± | − (++ Lymph) | Not Significant |

Our data demonstrate that the presence of MHC class II IA correlated with susceptibility to fatty lesions in the hearts of the C57BL/6 animals and that the presence of IE molecules conferred protection from the fatty lesions. The role of CD4 cells in this process was confirmed by the finding that removal of CD4 cells from the susceptible C57BL/6 abrogated the pathology in the heart. Note the correlation between expression of IE, increased production of IL-4, and protection from fatty lesions resulting from a high fat diet. The results in Table 7 demonstrate that CD4+ T cells contribute to early fat deposition in the aortic sinus and that IE molecules suppress lesions. MHC class II molecules, IA or IE, regulate susceptibility to development of early atherosclerotic plaques, and that cytokine profiles are altered (not shown).

Example 6

NGF and EGF-Dependent Changes in Fas (CD95), B7.1 (CD80) and B7.2 (CD86) Expression on PC12, TrkA, and v-Crk Neuronal Cell Surface Materials and Methods Cell Culture: Rat pheochromocytoma cell lines, including PC12, Trk and v-Crk cells were a kind gift from Dr. Raymond Birge. They were maintained in complete RPMI 1640 (GIBCO) supplemented with 7% heat inactivated fetal calf serum and 3% heat inactivated horse serum at 37° C. in a humidified incubator with 5% CO2. The PC12 transfectants were generated as described previously (Glassman et al., 1997, Hempstead et al., 1994). Cells were plated in 6 well culture plates at a concentration ranging from 2-8×10$^6$ cells/well, according to the cell type's growth kinetics, and 5 ml complete medium. NGF-7S from mouse submaxillary glands (Sigma Chemical Co.) or EGF, kindly provided by Dr. Raymond Birge, was added at a concentration of 50 ng/ml culture medium and the cells were incubated for 24 or 48 hours.

Cytofluorometric Analysis: Cells were harvested after a 10 minute incubation period on ice in order to diminish their adherence to the plastic culture flask. They were spun at 1210 rpm, for 7 minutes, resuspended in medium and counted after trypan blue staining. Equal numbers of cells were placed in 12×75 mm flow tubes (range: 0.1-1×106 cells/tube), washed in PBS and 5% FBS and stained at 4° C. The following stains were used: a) fluorescein isothiocyanate (FITC) hamster IgG isotype standard, b) FITC anti-mouse Fas, c) FITC anti-mouse CD80 (B7.1), d) phycoerythrin (PE) mouse IgG2b K isotype standard and e) PE anti-mouse CD86 (B7.2). All antibodies were obtained from Pharmingen.

After incubation on ice for 20 minutes, cells were washed, resuspended in PBS and 5% FCS and analyzed by flow cytometry (Becton Dickinson). Histogram plots were derived from dot plots gated on the live cell population according to the forward versus side scatter ratio (Cell Quest Program). The absolute Fas, B7.1 and B7.2 values presented on the graphs were obtained by subtracting the geometric mean fluorescence of the specific antibody from the mean geometric fluorescence of the corresponding isotype. Values were considered subjectively positive (+) if the difference was statistically significant (p<0.001) according to the applied Kilmogorov-Smirnov statistical analysis.

Results

Fas cell surface expression after NGF stimulation: As shown in FIG. 25 (panels A, D, G) Fas is constitutively expressed on the surface of PC12 and TrkA cells. NGF stimulation abrogates Fas expression on PC12 cells and paradoxically increases its expression on Trk cells at 24 hours. Fas levels tend to return to basal values on PC12 cells and are maintained constant on TrkA cells after 48 hours of NGF stimulation. V-Crk constitutive cell surface Fas expression is minimal but statistically significant, and it totally abrogated after NGF stimulation at 48 hours.

Fas cell surface expression after EGF stimulation: EGF stimulation at 24 and 48 hours also downregulates Fas expression on PC12 and Trk cells; EGF stimulation at 48 hours totally abrogates Fas expression on both cell types. On the other hand, EGF stimulation at 24 hours significantly up-regulates Fas expression on v-Crk cells, but it is again down-regulated and abrogated by EGF stimulation at 48 hours.

B7.1 cell surface expression after NGF stimulation. B7.1 is constitutively highly expressed on the surface of unstimulated PC12 and Trk cells (FIG. 25, panels B and E). Its expression is minimal on unstimulated v-Crk cells (FIG. 25, panel H). NGF stimulation initially downregulates B7.1 expression on PC12 cells at 24 hours, but it tends to return to basal values at 48 hours. NGF stimulation has no effect on B7.1 expression on the surface of Trk cells and v-crk cells.

B7.1 cell surface expression after EGF stimulation: EGF stimulation at 24 hours significantly lowers the detection of high B7.1 levels on the surface of PC12 cells; EGF stimulation at 48 hours reestablishes the basal values. As in $PCl_2$ cells, B7.1 expression is lowered after EGF stimulation of Trk cells at 24 hours and reestablished at the 48 hour time point. EGF stimulation significantly increases B7.1 expression on v-Crk cells after 24 and 48 hours of culture.

B7.2 cell surface expression after NGF stimulation: B7.2 cell surface expression is minimal on unstimulated PC12 cells (FIG. 25, panel C,F,I). NGF stimulation at 24 hours has no effect on its expression but stimulation at 48 hours completely abrogates its expression. Trk B7.2 cell surface expression is also minimal on unstimulated cells, it is slightly down-regulated by NGF stimulation at 24 hours and abrogated by NGF withdrawal. There is no B7.2 cell surface expression on v-Crk cells nor is it induced by NGF stimulation.

B7.2 cell surface expression after EGF stimulation: EGF stimulation at 48 hours up-regulates B7.2 expression on PC12 but this is most significant on the surface of Trk and v-crk cells. EGF stimulating at 48 hours is the only instance whereby there is significant induction of the constitutively absent B7.2 molecule on v-Crk cells. EGF withdrawal totally rescinds this effect and B7.2 levels are again undetectable.

In PC12 cells and its mutant variants, NGF induces proteins required for the acquisition of a sympathetic neuronal phenotype, potentiating cellular differentiation as reflected by an increase in the size and flattening of the neuronal soma and particularly by inducing neurite outgrowth (Ray Paper, J. Bio Chem 1995). By contrast, EGF stimulation of these cells induces their entry into the cell cycle and thus, cellular proliferation, by binding to another receptor also belonging to the tyrosine kinase receptor family (Hempstead et al., 1994; Siegel et al., 1994). The NGF and EGF receptor pathways appear to be very similar since they both activate the receptor-type tyrosine kineses, the Erk2/MAPK pathway and involve the Ras proteins (Chao, 1992; Ray, Id Menendez Iglesias et al., 1997) It has been found, according to the invention, however, that the effects of these molecules are quite different on the induction and abrogation of Fas, B7.1 and B7.2 expression on the neuronal cell surface suggesting that the induction of these molecules by growth factors NGF and EGF is mediated by a different intra-cellular signaling pathways albeit dependent on tyrosine kinase activation.

As described above Fas B7.1 and B7.2 are constitutively expressed on PC12 and TrkA cells maintained in culture. Fas expression on PC12 cells is significantly decreased by NGF stimulation (NGFS). Early NGFS of TrkA cells induces an increase in Fas expression over basal levels. Microglia constitutively express Fas ligand (Bonetti and Raine, 1997; Menendez Iglesias et al., 1997) and perhaps direct cell-cell contact between the neurons and microglia is required for the interaction of Fas and Fas ligand and the development of apoptosis or a co-stimulatory mitotic signal. In TrkA cells that overexpress the Trk receptor, NGF-induced Fas expression can promote cell division as NGF stimulates mitosis at that time period and synchronously play a role in the differentiation process and the development of filopodia. On TrkA cells, the higher induction of Fas expression correlates with the increased numbers of tyrosine kinase A surface receptors and thus, the development of a sustained increased stimulus for the mRNA translation of the Fas protein and its secondary expression on the cell surface.

EGF stimulation (EGFS) significantly diminishes and even abrogates Fas expression on PC12 and TrkA cells. However, its expression increases three-fold in v-Crk cells transiently after EGFS at 24 hours and disappears after EGFS at 48 hours. It has been shown that EGFS induces the development of neurite processes on the PC12 v-crk mutant not on native PC12 cells (Hempstead et al., 1994) and this clearly correlates with the induction of Fas on the v-Crk membrane cell surface, but does not explain the down-regulation of Fas observed in Trk and PC12 cells. EGF receptors are also expressed on cortical neurons, the cerebellum and hippocampus, and appear to act on mitotic cells and postmitotic neurons (Yamada et al., 1997).

NGFS and NGFW condition a minor upregulation of B7.1 on PC12, TrkA and v-Crk cells; however, NGFW at 48 hours does diminish B7.1 expression by 60% on v-Crk cells. In contrast, we consider that the effect of NGF on B7.2 on all three cell types is negligible. However, EGFS at 48 hours, significantly increases B7.1 expression on all cell variants but its expression clearly decreases after EGFW. EGFS at 48 hours also significantly increase B7.2 expression on PC12 and Trk cells and induces its expression on v-Crk cells. EGFW at 24 and 48 hours correlates with B7.2 down-regulation in PC12 and TrkA cells and paradoxically increases B7.2 expression no v-Crk cells at 24 hours; it is immediately down-regulated after EGFW at 48 hours. Therefore, Fas expression on v-Crk cells and B7.1-B7.2 expression on all cell types, but particularly on v-Crk cells, appear to be EGF-dependent. V-Crk cells are characterized by the presence of a fusion protein with viral gag sequences fused to the cellular sequences of the Src homology regions 2 and 3 (SH2 and SH3) (Hempstead et al., 1994). C-src also possesses tyrosine kinase activity (Vaingankar and Martins-Green, 1998) and perhaps these modifications in its sequence allow it to act similarly to the EGF receptor per se and increase the signal intensity for the expression of these cell surface molecules. Withdrawal of the stimulus (EGFW) reverts the expression of these molecules towards basal levels.

Identification of Immune Recognition Molecules on Treated Versus Non-Treated Ganglia.

Ganglia, are removed from Po (one-day old mice) brain and plated into cultures. The sensory neurons do not have to be separated away from Schwann cells. Isolated ganglia are cultured for at least 72 hours under the following conditions:
1) No Treatment
2) In the presence of nerve growth factor (NGF) for 56 hours
3) followed by harvest, wash, and replating in the presence of antibodies to NGF. Cells are harvested by cell scraping and dispersed into single cell suspensions. Cells are stained for cell surface B7-1, B7-2, CDR8, and Trk A (NGF receptor) using monoclonal antibodies to these molecules.

The cells are cultured as described above but in the presence of CTLA-4-HuIg to inhibit cell interactions (synapses) which will protect Group I from death. This shows that B7-bearing cells cause the CD28+ or CTLA4+ cell to release NGF and promote innervation. Additionally histological sections are stained by immunofluorescence (using the anti B7 and TrkA antibodies) immediately ex vivo intact mouse brain.

Example 7 UCP is Present in a Panel of Tumor Cells

Figure 14:
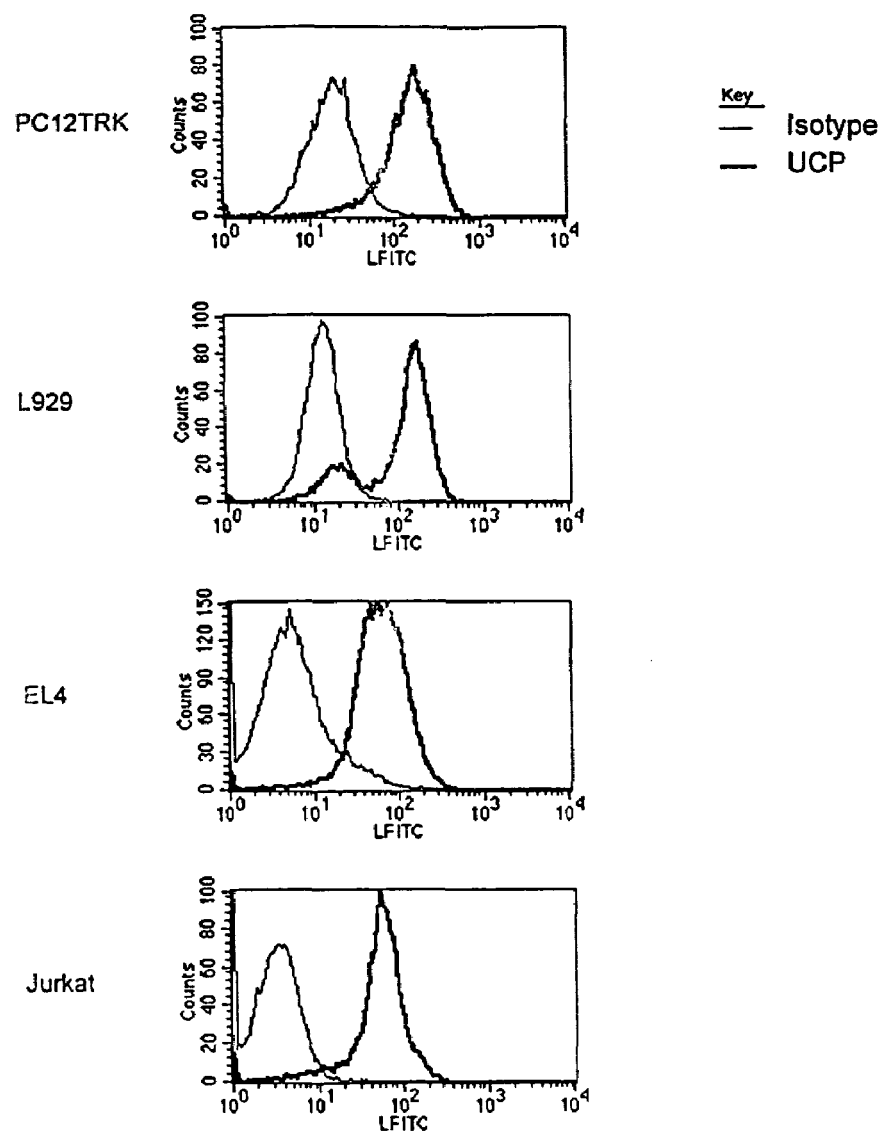
FIG. 14 demonstrates that UCP is expressed in a panel of Tumor Cells.

We extended our analysis of intracellular expression of UCP to other tumor cells (FIG. 14). All of the tumor cells lines examined express UCP intracellularly. These data are consistent with the possibility that expression of UCP in tumor cells is generalizable to all tumor cells, and likely results from the well documented shift in subcellular production of ATP from mitochondria to cytosol as cells divide. Importantly, these data also demonstrate that expression of UCP2 is not specific to lymphoid tumors. The L929 cells are fibroblasts and the PC12 Trk cells which are derived from pheochromocytoma cell lines, respectively. The EL4 cells are a mouse thymoma cell line and Jurkat are human T cell tumor cells.

Flow cytometric analysis of intracellular UCP. Isotype control (thin lines) versus anti-UCP (thick lines), on cells which had been permeabilized anf stained as indicated. The histograms represent FITC isotype control (thin) versus stained with Rabbit anti-UCP (a kind gift of Mary Ellen Harper) FITC-anti-Rabbit outerstep (thick lines). A Coulter Epics Elite flow cytometer with a single excitation wavelength (488 nm) and band filters for PE (575 nm), FITC (525 nm) and Red613 (613 nm) was used to analyze the stained cells. Each sample population was classified for cell size (forward scatter) and complexity (side scatter), gated on a population of interest and evaluated using 40,000 cells. Criteria for positive staining were established by comparison with isotype controls, thin lines to specific stain, thick lines.

Figure 15:
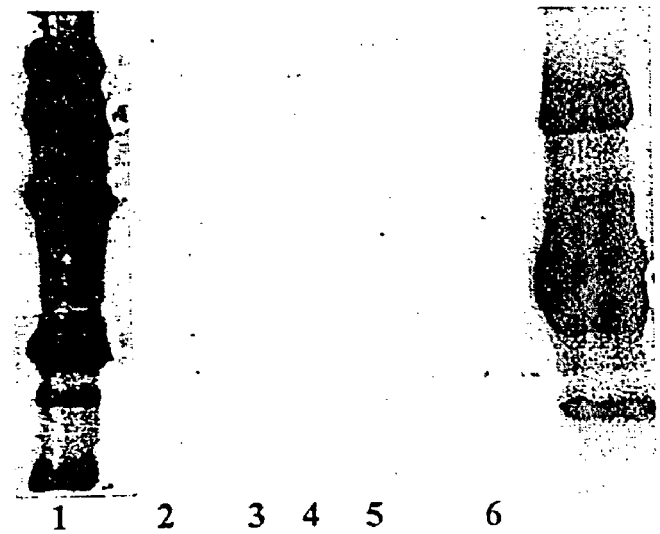
FIG. 15 shows that flow cytometrically detected UCP expression was mitochondrial using isolated mitochondria from L1210 and L1210 DDP, and Western Blot analysis blotting with rabbit anti-UCP antibodies.

To confirm that flow cytometrically detected UCP expression was mitochondrial, we isolated mitochondria from L1210 and L1210 DDP, and performed Western Blot analysis blotting with rabbit anti-UCP antibodies, FIG. 15. This representative blot shows greater levels of mitochondrial UCP in the drug resistant L1210/DDP than in L1210/0. The detected mitochondria protein has an approximate molecular weight of 30 kDa, close to the predicted molecular weight of UCP2 (33 kDa).

Representative Western blot of protein isolated from purified mitochondrial fractions of L1210/0 and L1210/DDP cells. Mitochondria were isolated using differential centrifugation as adapted from REF, REF (Reinhart, P H, Taylor, W M and Bygrave F L (1982) A procedure for the rapid preparation of mitochondria from rat liver. Biochem. J. 204: 731-735. and Sims N R (1990) Rapid isolation of metabolically active mitochondria from rat brain and subregions using Percoll density gradient centrifugation. J. Neurochem. 55:698-707.) Lane 1: Molecular weight markers (BIORAD Biotinylated SDS-PAGE standards. After transfer of proteins to nitrocellulose, this lane is cut off and detection of standards is performed using Avidin-HRP). Lanes 2 and 3: L1210/0 mitochondrial protein (40 µg) from two distinct mitochondrial preparations. Lanes 4 and 5: L1210/DDP mitochondrial protein (40 µg) from two distinct mitochondrial preparations. Lane 6: uncoupling protein standard (0.75 µg) from rat brown adipose tissue (which expresses UCPs 1-3). Rabbit anti-hamster UCP was used at a dilution of 16,000. The secondary antibody: goat anti-rabbit IgG conjugated to HRP at 1:10,000. Chemiluminescent detection: Amersham ECL kit.

Figure 16:
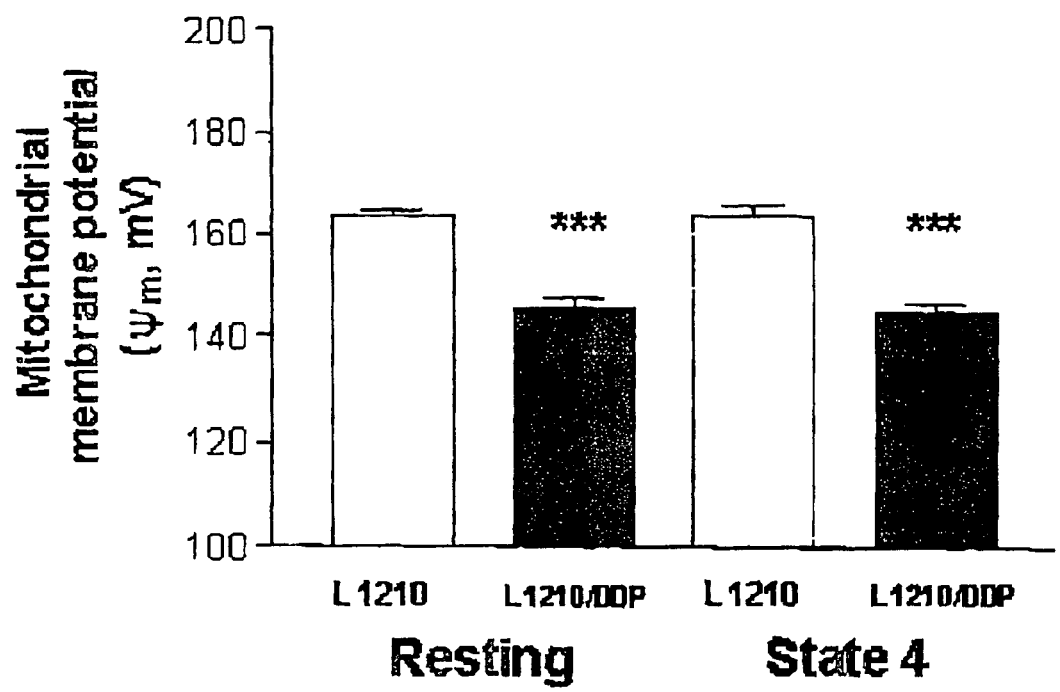
FIG. 16 shows that increased UCP corresponds to increased mitochondrial proton leak and a lower mitochondrial membrane potential (ΔΨm).

To determine whether increased UCP corresponded to increased mitochondrial proton leak and a lower mitochondrial membrane potential ($\Delta\Psi m$) we assessed characteristics of non-phosphorylating respiration in intact L1210 wild type and L1210 DDP cells (FIG. 16). State 4 $\Delta\Psi m$ in DDP cells, x mV, was significantly lower than in wild type cells, y mV ($p<0.001$), and state 4 oxygen consumption in DDP cells is significantly higher than in wild type cells, indicating increased mitochondrial proton leak.

Example 8

Figure 17A:
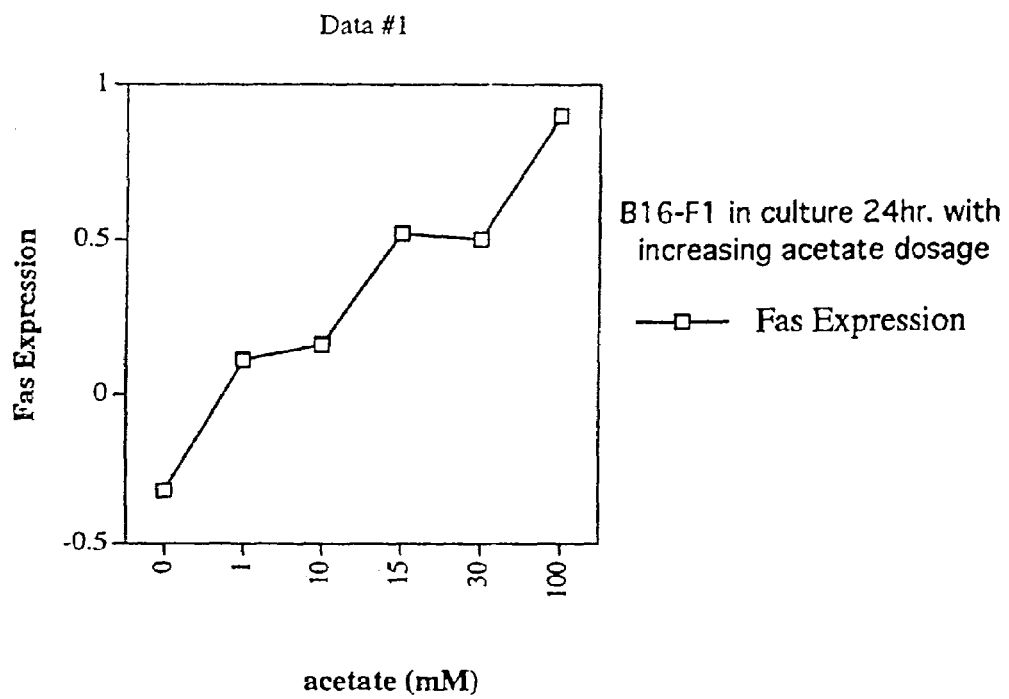
FIG. 17 depicts the level of cell surface Fas expression on non-permeabilized (panel A) and intracellular Fas expression in permeabilized (Panel B) B16 melanoma cells.
Figure 17B:
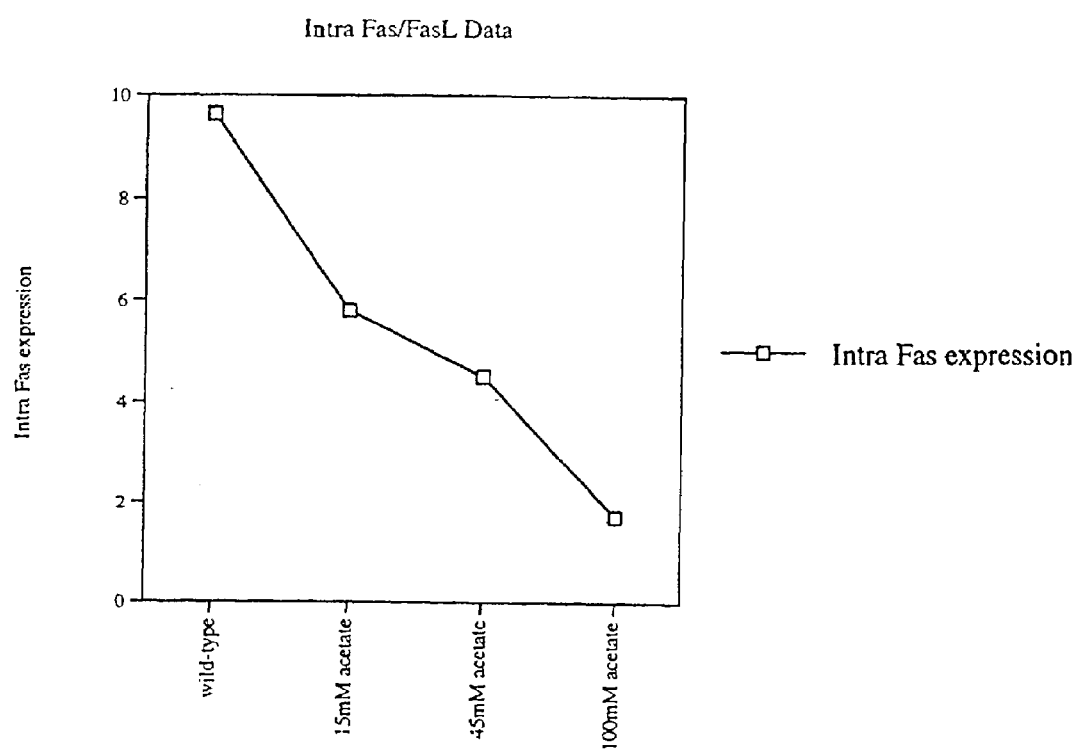

Rates of Glucose Utilization, Oxidation and Cell Surface and Intracellular Fas Levels in Melanoma Cells FIG. 17 depicts the level of cell surface Fas expression on non-permeabilized (panel A) and intracellular Fas expression in permeabilized (Panel B) B16 melanoma cells. B16 cells were cultured in the in the presence of different concentrations of sodium acetate and Fas expression was measured. With increasing concentrations of sodium acetate, the levels of intracellular Fas declined and the levels of cell surface Fas increased, demonstrating a translocation of Fas from intracellular stores to the surface.

Figure 18:
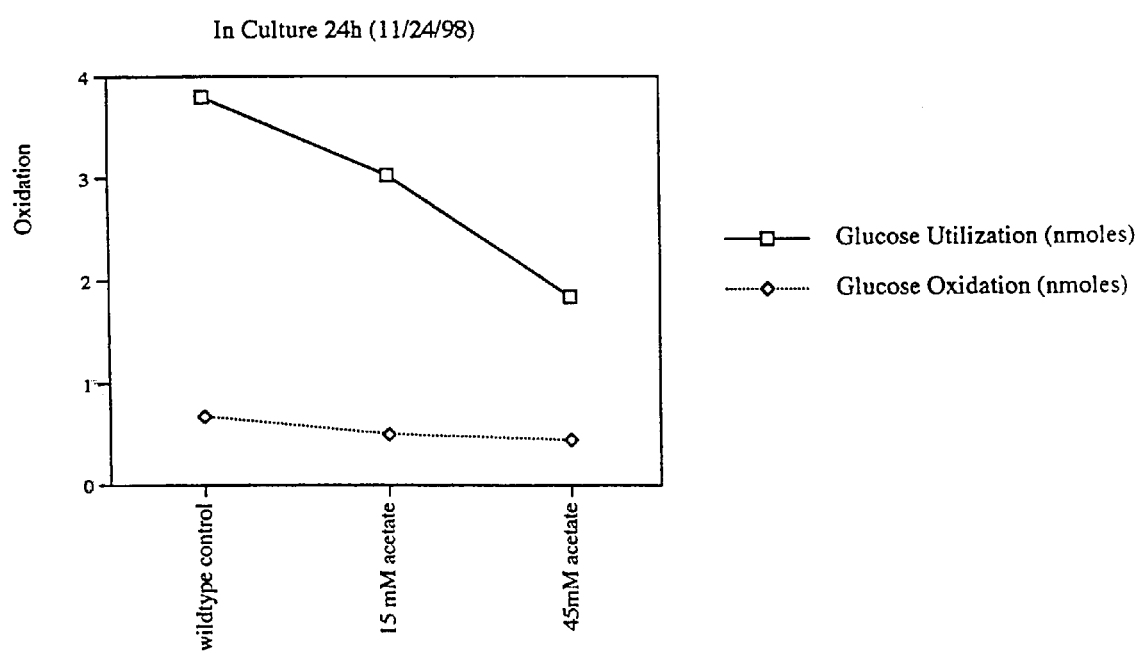
FIG. 18 depicts the rates of glucose utilization and oxidation in B16 melanoma cells.

FIG. 18 depicts the rates of glucose utilization and oxidation in B16 melanoma cells. Again cells were cultured in the presence of varying concentration of sodium acetate. Both glucose utilization and glucose oxidation (measured in nmoles) decreased with increasing concentrations of sodium acetate, demonstrating a correlation with expression of cell surface Fas in the same cells.

Example 9

Normal Mouse T Cells Express IE

Figure 19:
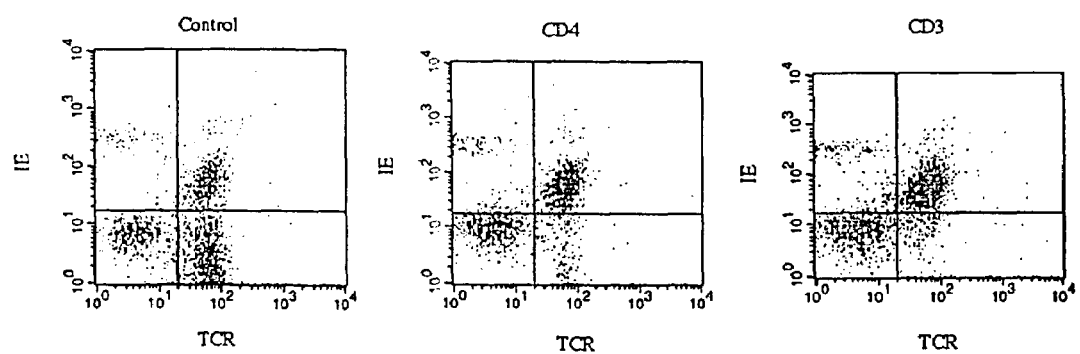
FIG. 19 shows that possibility that normal mouse T cells express IE.

Previous work with human T cells indicates that activation of the T cells by antigens or engagement of CD4 results in expression of HLA DR on the T cell surface. Expression of MHC class II on mouse T cells is controversial. Reports indicate both positive and negative results. The studies to date did not distinguish between failure to express IA versus IE. To address the possibility that normal mouse T cells express IE we isolated lymph nodes or spleens as indicated from strains of animals which express IE, Balb/c, CBA, and AKR mice, spleens or nodes were taken from 4 week old mice, minced to single cell suspension, and red blood cells were removed via Gey's treatment. Splenocytes were then passed over Cellect Columns (Cytovax, Edmonton, Canada) to purify CD4$^+$ T cells. CD4$^+$ T cells were collected, found to be 98.5% pure, and contaminants were identified as NK and γδ T cells flow cytometrically. The CD4 T cells were treated with antibody to CD4 (GK1.5) at 10 μg/ml/10$^7$ cells. washed and treated with rabbit anti-rat antibody for 45 minutes at 37° C., followed by washing. The cells were cultured overnight and stained with FITC conjugated anti-IE antibody (14-4.4 S), FIG. 19, or 14-4.4S and counterstained with anti-TCR as indicated in FIG. 19 b.

Figure 20:

For the PCR experiment below, FIG. 20 purified CD4$^+$ T cells, 5×10$^6$/ml, were incubated for 8 hrs. with biotinylated antibodies for CD4 (GK1.5), CD28, CD3 (145.2C11) alone, CD4 and CD28, CD3 and CD28, or no treatment. Experimental setup included wells of purified T cells and percoll isolated B cells added to control for potential MHC Class II$^+$ contaminants. B cells, 5×10$^5$ cells, which is 5% of purified T cells (far greater than the 1.5% contaminants seen following Cellect Column purification) were added to T cell wells. Cells were then washed, collected and total RNA was isolated using an RNA isolation kit, RNEasy (Qiagen, Chatsworth Calif.). Single strand DNA was generated from 2 μg of RNA using SuperScript II reverse transcriptase (GIBCo/BRL Gaithersburg, Md.). PCR was done using MHC Class II, (1-E, exon 3 5'-TAGCTGAGCCCAAGGT-GACT and 5' TCACCAGGGTCTGGTAGGTC) primers. PCR protocol was: 1 min at 94° C., 1 min at 60° C., and 2 min. at 72° C. for 35 cycles. Following PCR, samples were loaded onto 1% agarose gels, stained with ethidium bromide and visualized with UV light.

Example 10

Use of Fatty Acids as a Mitochondrial Carbon Source

Figure 21:
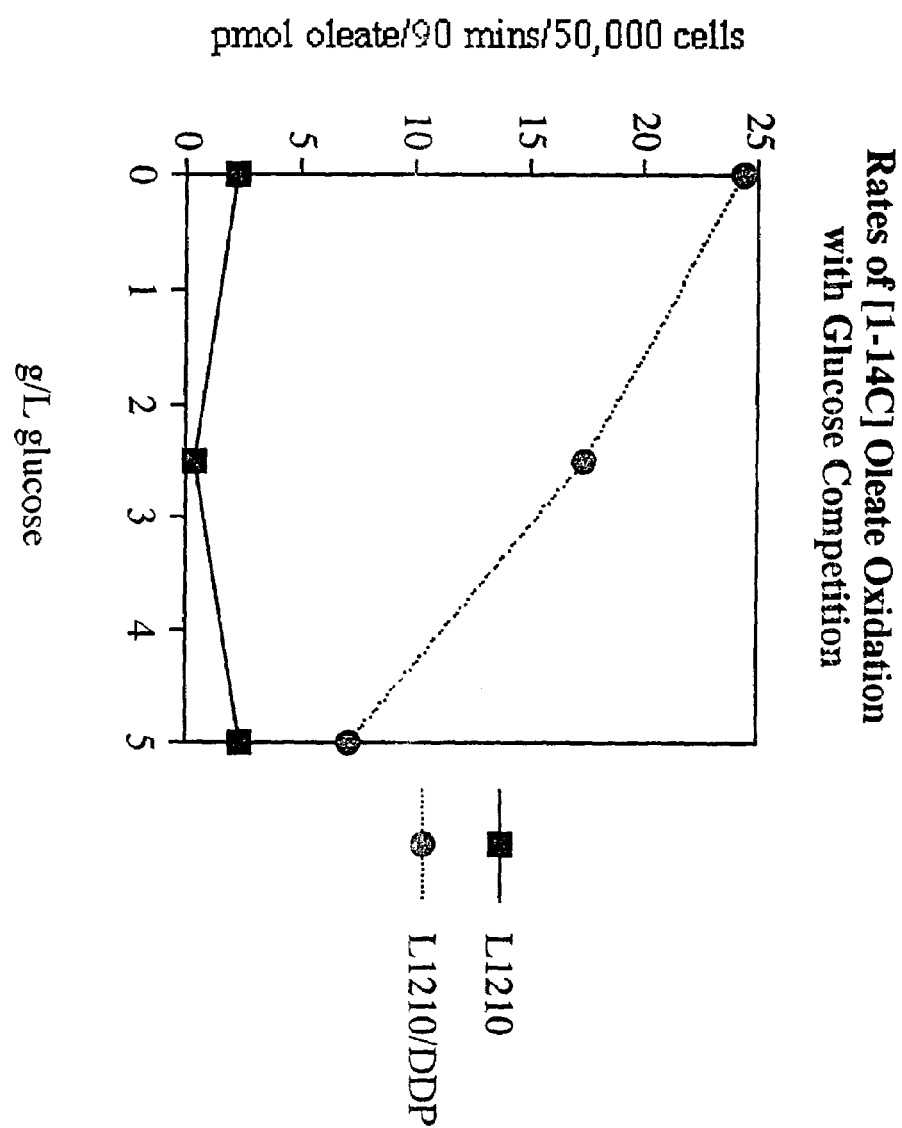
FIG. 21 shows the results of fatty acid (Oleic Acid) as a mitochondrial carbon source.

FIG. 21 shows the results of fatty acid (Oleic Acid) as a mitochondrial carbon source. Rate of oleate oxidation was measured by incubating cells for 90 min at 37° C. in 100 μl of reaction buffer, glucose (2.8, 8.3, 27.7 mmol/l), 1.7 mCi (U-14C oleaic acid). The reaction was carried out in a 1 ml cup in a 20 ml scintillation vial capped by a rubber stopper with a center well that contains filter paper. Metabolism was stopped and CO$_2$ liberated with 300 μl 1 mol/l HCl injected through the stopper into the cup containing the cells. CO$_2$ was trapped in the filter paper by injecting 10 ml 1 mol/l KOH into the center well, followed 2 hours later by liquid scintillation counting. Tubes containing NaHCO$_3$ and no cells were used to estimate the recovery of $^{14}$CO$_2$ in the filter paper, routinely close to 100%. Values indicate the rate of CO2 production by L1210DDP cells (round symbols) or L1210 cells (square symbols). The L1210 DDP use oleic acid at much higher rates than the L1210 cells.

Example 11 cAMP Levels in L1210 and L1210DDP

Figure 22:
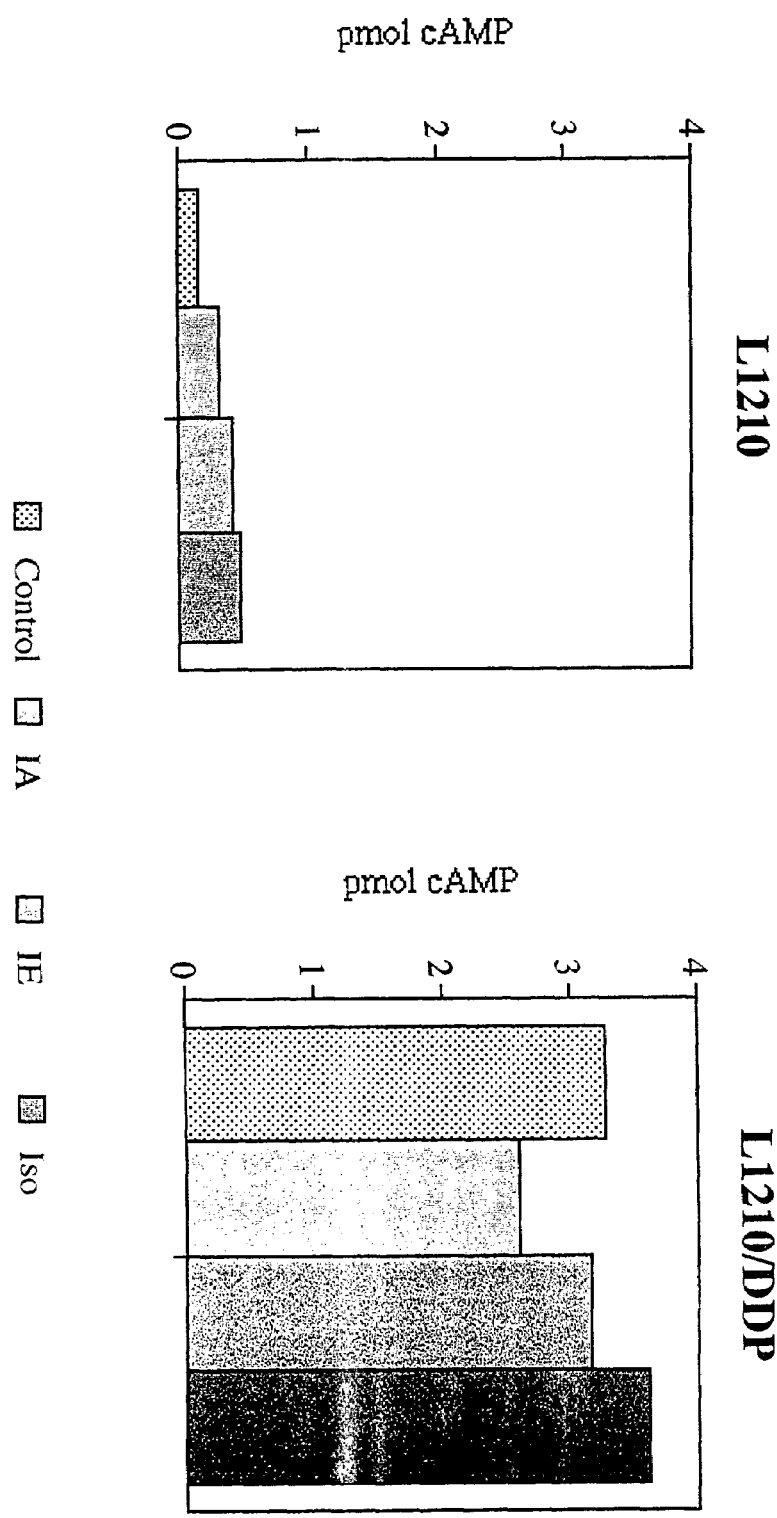
FIG. 22 shows levels of cAMP in L1210, left panel versus L1210DDP, right panel.

FIG. 22 shows levels of cAMP in L1210, left panel versus L1210DDP, right panel. Increasing intracellular levels of cAMP are necessary for the activity of uncoupling proteins. We have shown that class II engagement results in increased cAMP and we have determined that the mitochondrial membrane potential of L1210DDP cells is lower than L1210 cells. Thus, we used a radioimmunoassay to determine the levels of cAMP in L1210, left panel versus L1210DDP, right panel. Cells were treated for 10 minutes with nothing, antibodies to IA, IE, or with a beta adrenergic agonist, isoproterenol (10 microMolar). Cells were harvested and cAMP was extracted from the cells and cAMP levels determined using 125 I labeled cAMP in competitive inhibition in the presence of antibodies to cAMP, radioimmunoassay.

Example 12

Sodium Acetate as a Mitochondrial Modifying Agent

Figure 23:
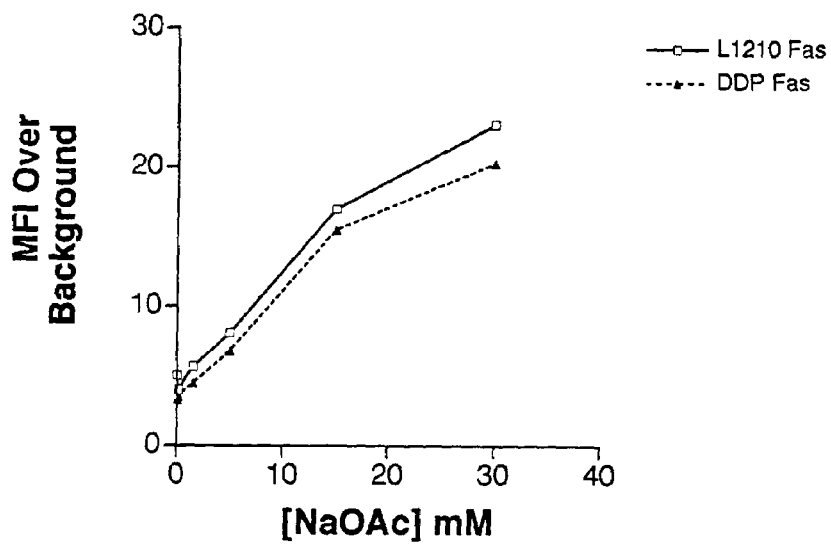
FIG. 23 is a graph depicting Sodium Acetate as a mitochondrial modifying agent.
Figure 23:
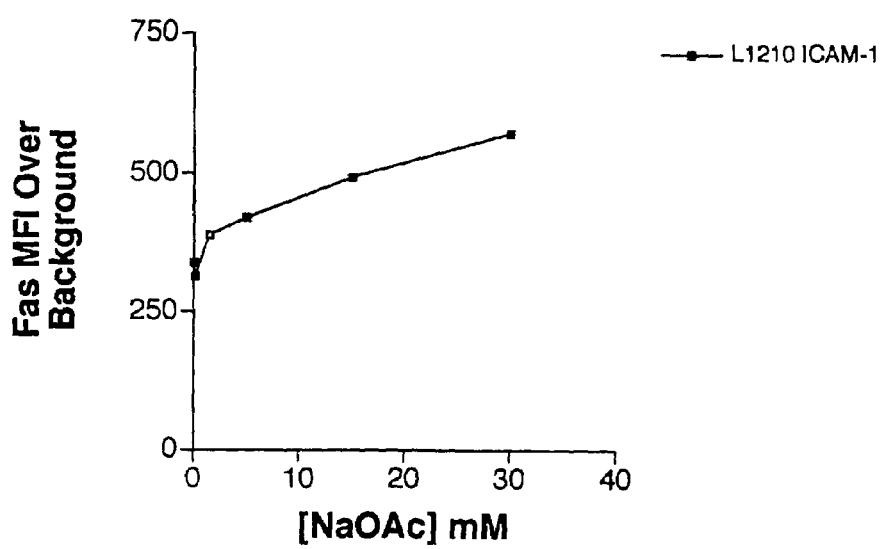

FIG. 23 is a graph depicting Sodium Acetate as a mitochondrial modifying agent. L1210 or L1210DDP cells were cultured in the presence of graded concentrations of sodium acetate in the medium. Cells were stained with Jo2.2, a fluorescein conjugated anti-Fas antibody, or an isotype control. Cell surface staining was measured flow cytometrically. The Percentage of mean fluorescence intensity over the isotype control was plotted. The data indicate that the presence of acetate increases cell surface Fas expression in both cell lines.

Figure 24:
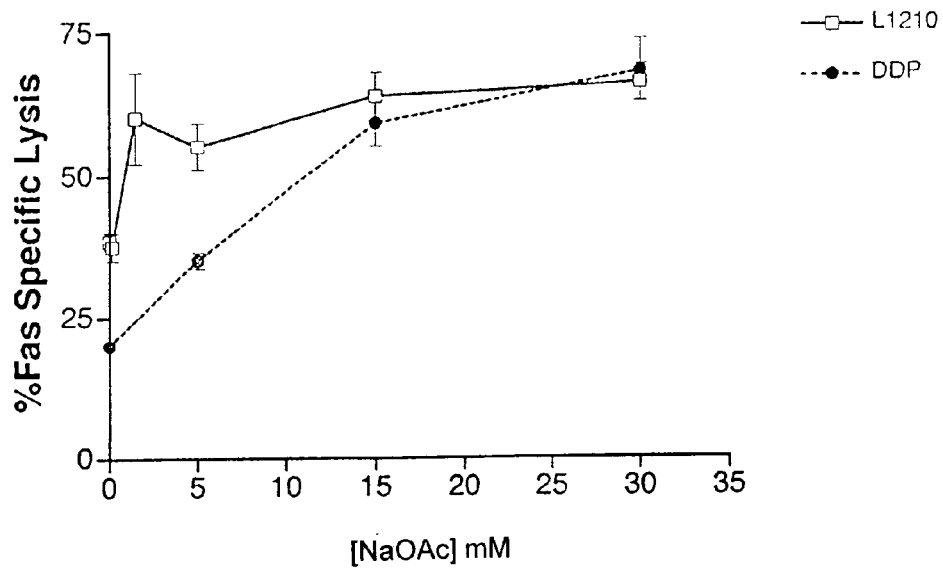
FIG. 24 is a graph depicting the effects of acetate on susceptibility to Fas-dependent cell death.
Figure 24:
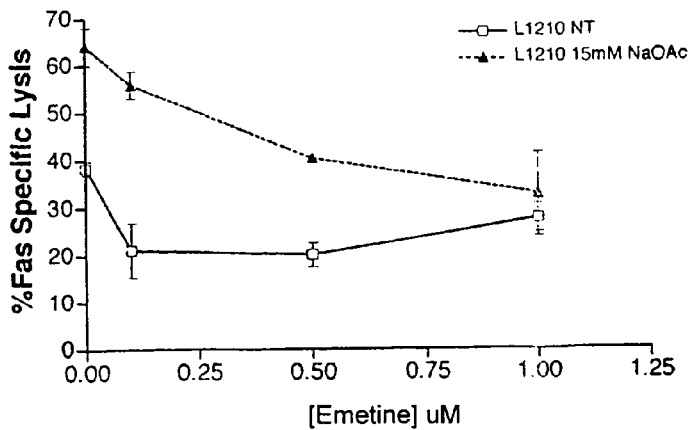

FIG. 24 is a graph depicting the effects of acetate on susceptibility to Fas-dependent cell death. Cells cultured with acetate were loaded with 51 Cr and plated onto FasL bearing or mock transfected fibroblast to determine sensitivity to Fas-induced cell death. Results are reported as percent chromium release from cells in the presence of FasL bearing cells over mock-transfectants. The data indicate that in a dose dependent manner, culture of both cell types with acetate results in susceptibility to Fas-dependent cell death.

Each of the foregoing patents, patent applications and references is hereby incorporated by reference, including U.S. Provisional Application Ser. No. 60/082,250 filed Apr. 17, 1998, U.S. Provisional Application Ser. No. 60/101,580 filed Sep. 24, 1998 and U.S. Provisional Application Ser. No. 60/094,519 filed Jul. 24, 1998, from which this application claims priority under 35 USC §119(e). While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

I claim:

1. A method for decreasing mitochondrial membrane potential in a tumor cell, comprising contacting the tumor cell with an amount of an MHC class II HLA-DR inducing agent effective to induce the expression of MHC class II HLA-DR on the surface of the tumor cell, wherein the MHC class II HLA-DR inducing agent is a UCP expression vector or a TCRαβ binding molecule and administering an MHC class II HLA-DR ligand that is a MHC class II HLA-DR binding peptide or is an anti-MHC class II HLA-DR antibody or antigen-binding fragment thereof to the tumor cell to selectively bind MHC class II HLA-DR on the surface of the cell in an amount effective to decrease mitochondrial membrane potential in the tumor cell.

2. The method of claim 1, wherein the MHC class II HLA-DR ligand is administered to the tumor cell in vivo in an amount effective for causing cell lysis of the tumor cell.

3. The method of claim 1, wherein the MHC class II HLA-DR ligand is an anti-MHC class II HLA-DR antibody or antigen binding fragment thereof.

4. The method of claim 1, wherein the MHC class II HLA-DR inducing agent and the MHC class II HLA-DR ligand are administered simultaneously.

5. The method of claim 1, wherein the MHC class II HLA-DR inducing agent and the MHC class II HLA-DR ligand are administered orally.

6. The method of claim 1, wherein the MHC class II HLA-DR inducing agent and the MHC class II HLA-DR ligand are administered locally.

7. A method for decreasing mitochondrial membrane potential in a human cell, comprising contacting the human cell with an amount of an MHC class II HLA-DR inducing agent effective to induce the expression of MHC class II HLA-DR on the surface of the human cell, wherein the human cell is not an antigen presenting cell and administering an MHC class II HLA-DR ligand that is a MHC class II HLA-DR binding peptide to the human cell to selectively bind MHC class II HLA-DR on the surface of the cell in an amount effective to decrease mitochondrial membrane potential in the human cell.

8. A method for decreasing mitochondrial membrane potential in a tumor cell, expressing MHC class II HLA-DR on the surface, of a subject, comprising administering to the subject an amount of an MHC class II HLA-DR inducing agent effective to induce the expression of MHC class II HLA-DR on the surface of the tumor cell, wherein the MHC class II HLA-DR inducing agent is a UCP expression vector or a TCRαβ binding molecule and administering an MHC class II HLA-DR ligand that is a MHC class II HLA-DR binding peptide to the subject to selectively bind MHC class II HLA-DR on the surface of the tumor cell in an amount effective to decrease mitochondrial membrane potential in the tumor cell.

9. The method of claim 8, wherein the method is performed in vivo.

10. The method of claim 8, wherein the method is performed ex vivo.

* * * * *